(12) United States Patent
Valenta et al.

(10) Patent No.: US 11,771,760 B2
(45) Date of Patent: Oct. 3, 2023

(54) TREATMENT AND PREVENTION OF HOUSE DUST MITE ALLERGIES

(71) Applicant: Worg Pharmaceuticals (Zhejiang) Co., Ltd., Huzhou (CN)

(72) Inventors: Rudolf Valenta, Theresienfeld (AT); Mirela Curin, Vienna (AT); Kuan-Wei Chen, Vienna (AT); Susanne Vrtala, Vienna (AT)

(73) Assignee: WORG PHARMACEUTICALS (ZHEJIANG) CO., LTD., Huzhou (CN)

( * ) Notice: Subject to any disclaimer, the term of this patent is extended or adjusted under 35 U.S.C. 154(b) by 0 days.

(21) Appl. No.: 17/055,817

(22) PCT Filed: May 17, 2019

(86) PCT No.: PCT/EP2019/062800
§ 371 (c)(1),
(2) Date: Nov. 16, 2020

(87) PCT Pub. No.: WO2019/219907
PCT Pub. Date: Nov. 21, 2019

(65) Prior Publication Data
US 2021/0128718 A1 May 6, 2021

(30) Foreign Application Priority Data
May 18, 2018 (EP) .................................... 18173258

(51) Int. Cl.
| | |
|---|---|
| *C07K 14/005* | (2006.01) |
| *A61K 39/385* | (2006.01) |
| *A61P 37/08* | (2006.01) |
| *A61K 39/35* | (2006.01) |
| *C07K 14/435* | (2006.01) |
| *A61K 39/00* | (2006.01) |

(52) U.S. Cl.
CPC .............. *A61K 39/35* (2013.01); *A61K 39/385* (2013.01); *A61P 37/08* (2018.01); *C07K 14/005* (2013.01); *C07K 14/43531* (2013.01); *A61K 2039/6075* (2013.01); *C07K 2319/00* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS
9,844,591 B2 * 12/2017 Niespodziana ...... A61K 39/292
2016/0257722 A1 * 9/2016 Valenta .................. A61K 39/35

FOREIGN PATENT DOCUMENTS

| EP | 1908776 A1 | 4/2008 |
|---|---|---|
| EP | 2727934 A1 | 5/2014 |
| WO | 0050044 A1 | 8/2000 |
| WO | 2009118642 A2 | 10/2009 |
| WO | WO 2012/168487 * | 2/2012 |
| WO | 2012168487 A1 | 12/2012 |
| WO | 2015070925 A1 | 5/2015 |
| WO | 2017140913 A2 | 8/2017 |

OTHER PUBLICATIONS

Accession No. AFC06206, (2010).*
International Search Report from Appl. No.: PCT/EP2019/062800, dated Jul. 23, 2019.
Banerjee et al., Conversion of Der P 23, a New Major House Dust Mite Allergen, into a Hypoallergenic Vaccine, The Journal of Immunology, (2014) 192:4867-4875.
Curin et al., Similar localization of conformational IgE epitopes on the house dust mite allergens Der p 5 and Der p 21 despite limited IgE cross-reactivity, Allergy, (2018) 73:1653-1661.
Huang et al., Towards a non-allergenic peptide mix containing the T cell epitopes of the clinically most relevant house dust mite allergens for tolerance induction, The Journal of Immunology, (2016) 196: No. suppl 1 192.5 XP002786218.
Bussières et al., Recombinant Fusion Proteins Assembling Der p 1 and Der p 2, Allergens from Dermatophagoides pteronyssinus. International Archives of Allergy and Immunol, (2010) 153:141-151.
Chen et al., Reduction of the in vivo allergenicity of Der p 2, the major house-dust mite allergen, by genetic engineering, Molecular Immunology, (2008) 45:2486-2498.
Casset et al., Varying Allergen Composition and Content Affects the in vivo Allergenic Activity of Commercial Dermatophagoides pteronyssinus Extracts, Int Arch Allergy Immunol (2012) 159:253-262.
Chen et al., Carrier-bound nonallergenic Der p 2 peptides induce IgG antibodies blocking allergen-induced basophil activation in allergic patients, Allergy, (2012), 67:609-621.
Curin et al., Engineering and characterization of recombinant fusion proteins comprising the clinically relevant house dust mite allergens for allergen-specific immunotherapy, Elsevier science publishers, (2018) Database accession No. EMB-623867572 abstract.
Martinez et al., An Engineered Hybrid Protein from Dermatophagoides pteronyssinus Allergens Shows Hypoallergenicity, International Journal of Molecular Sciences, (2019) 20:1-17.
An et al., Dermatophagoides farinae Allergens Diversity Identification by Proteomics, Molecular & Cellular Proteomics, (2013), 12:1818-1828.

(Continued)

Primary Examiner — Agnieszka Boesen
(74) Attorney, Agent, or Firm — NEVRIVY PATENT LAW GROUP P.L.L.C.

(57) ABSTRACT

The present invention relates to a fusion protein having formula (I)

$$X_1-Y-X_2 \qquad (I),$$

wherein $X_1$ and $X_2$ comprise each four to six allergen fragments or variants thereof fused to each other, wherein said allergen fragments are derived from at least two allergens of the genus *Dermatophagoides*, and wherein Y is a carrier protein.

22 Claims, 18 Drawing Sheets
Specification includes a Sequence Listing.

(56) References Cited

OTHER PUBLICATIONS

Focke-Tejkl et al., Development and characterization of a recombinat, hypoallergenic, peptide-based vaccine for grass pollen allergy, Journal of allergy and clinical Immunology, (2015) 135:1207-1217.
Curin et al., 1675 Engineering and characterization of recombinant fusion proteins comprising the clinically relevant house dust mite allergens for allergen-specific immunotherapy, Allergy: European Journal of Allergy and Clinical Immunology, abstracts (2018), p. 340. XP-002786220.

* cited by examiner

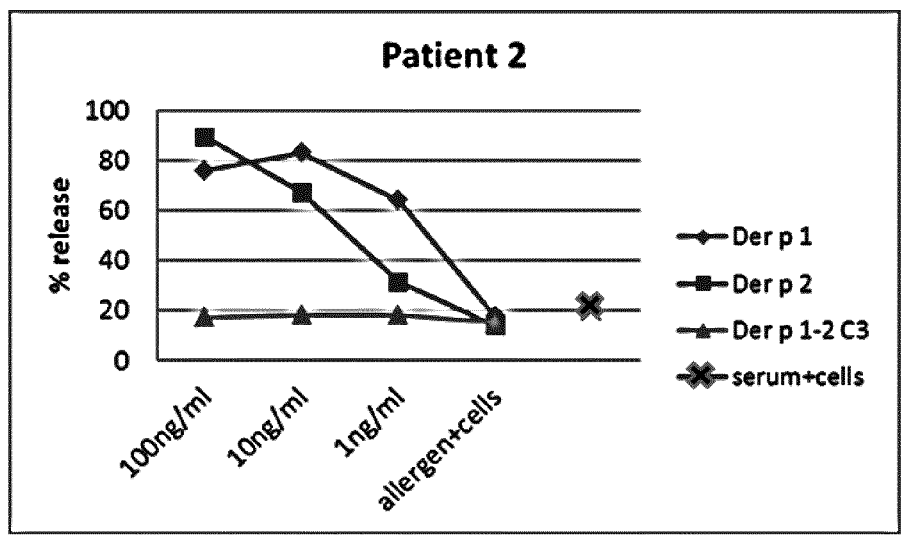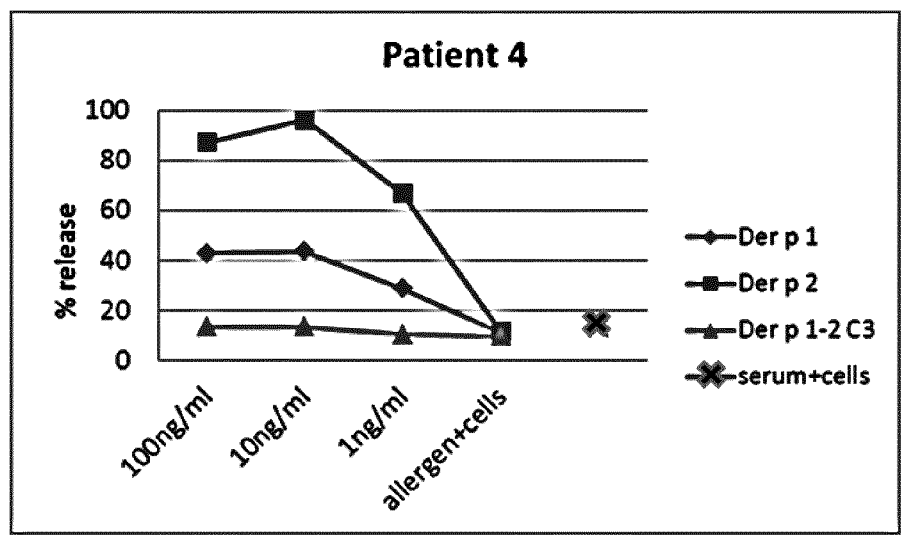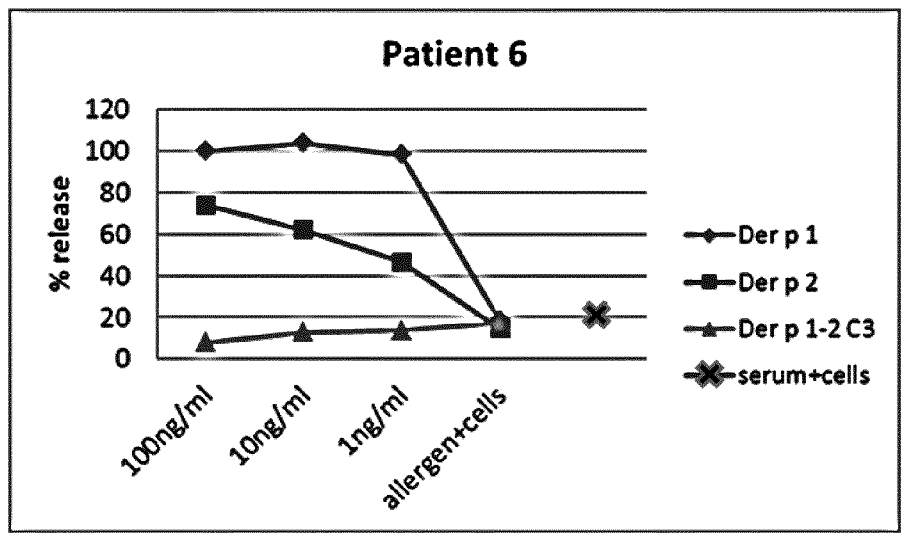
Fig. 4 (continued)

Fig. 6 nDer p 1 coated

| patient | 1 | 2 | 3 | 4 | 5 | 6 | 7 | 8 | 9 | 10 | mean |
|---|---|---|---|---|---|---|---|---|---|---|---|
| a-C3#1 Alum | 58 | 66 | 69 | 55 | 32 | 60 | 57 | 56 | 64 | 61 | 58 |
| a-C3#2 Alum | 52 | 60 | 63 | 53 | 25 | 56 | 55 | 50 | 60 | 56 | 53 |
| a-nDer p 1 Alum | 78 | 89 | 90 | 63 | 48 | 86 | 70 | 80 | 98 | 79 | 78 | rDer p 2 coated

| patient | 1 | 2 | 3 | 4 | 5 | 6 | 7 | 8 | 9 | 10 | mean |
|---|---|---|---|---|---|---|---|---|---|---|---|
| a-C3#1 Alum | 89 | 96 | 91 | 89 | 56 | 93 | 88 | 93 | 91 | 94 | 89 |
| a-C3#2 Alum | 84 | 93 | 90 | 85 | 54 | 91 | 83 | 88 | 88 | 91 | 85 |
| a-rDer p 2 Alum | 84 | 96 | 85 | 80 | 50 | 91 | 86 | 93 | 90 | 92 | 84 |

Der p 5 coated

| | Patient | 1 | 2 | 3 | 4 | mean |
|---|---|---|---|---|---|---|
| α- Der p 5 7 21 23_P6 #1 Alum | | 77 | 68 | 80 | 80 | 76 |
| α- Der p 5 7 21 23_P6 #2 Alum | | 91 | 87 | 83 | 79 | 85 |
| α- Der p 5 Alum | | 90 | 92 | 85 | 84 | 88 |

Der p 7 coated

| | Patient | 1 | 2 | 3 | 4 | mean |
|---|---|---|---|---|---|---|
| α- Der p 5 7 21 23_P6 #1 Alum | | 89 | 77 | 89 | 40 | 74 |
| α- Der p 5 7 21 23_P6 #2 Alum | | 92 | 74 | 88 | 42 | 74 |
| α- Der p 7 Alum | | 76 | 54 | 81 | 22 | 58 |

Der p 21 coated

| | Patient | 1 | 2 | 3 | 4 | mean |
|---|---|---|---|---|---|---|
| α- Der p 5 7 21 23_P6 #1 Alum | | 53 | 55 | 60 | 64 | 58 |
| α- Der p 5 7 21 23_P6 #2 Alum | | 46 | 50 | 64 | 72 | 58 |
| α- Der p 21 Alum | | 87 | 88 | 80 | 94 | 87 |

Der p 23 coated

| | Patient | 1 | 2 | 3 | 4 | 5 | 6 | mean |
|---|---|---|---|---|---|---|---|---|
| α- Der p 5 7 21 23_P6 #1 Alum | | 29 | 34 | 40 | 31 | 41 | 44 | 37 |
| α- Der p 5 7 21 23_P6 #2 Alum | | 37 | 39 | 43 | 35 | 45 | 54 | 42 |
| α- Der p 23 Alum | | 6 | 1 | 1 | 10 | 10 | 15 | 7 |

Fig. 7

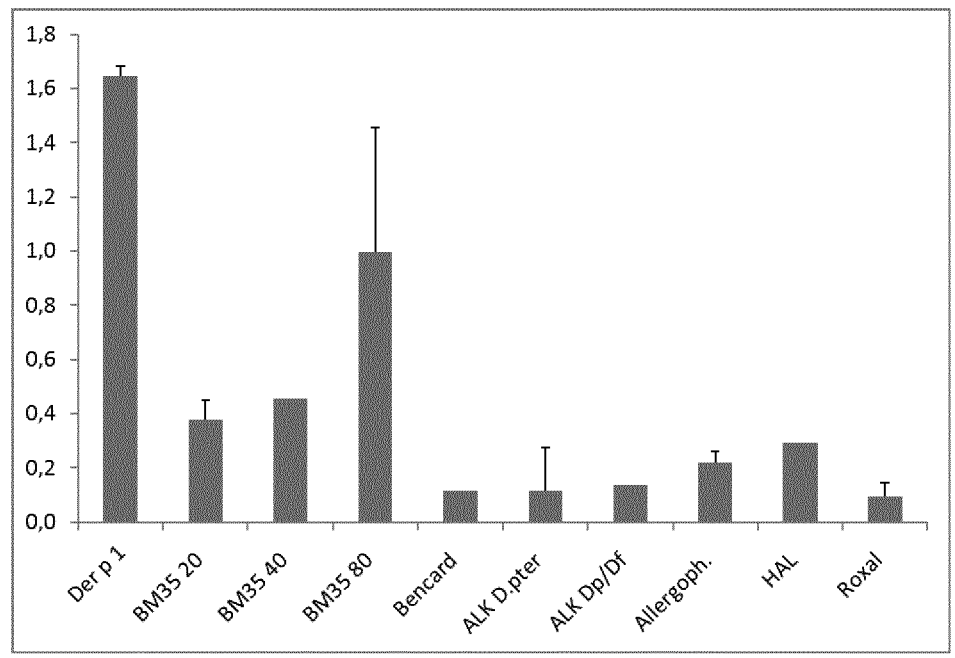
IgG titers after 38 days
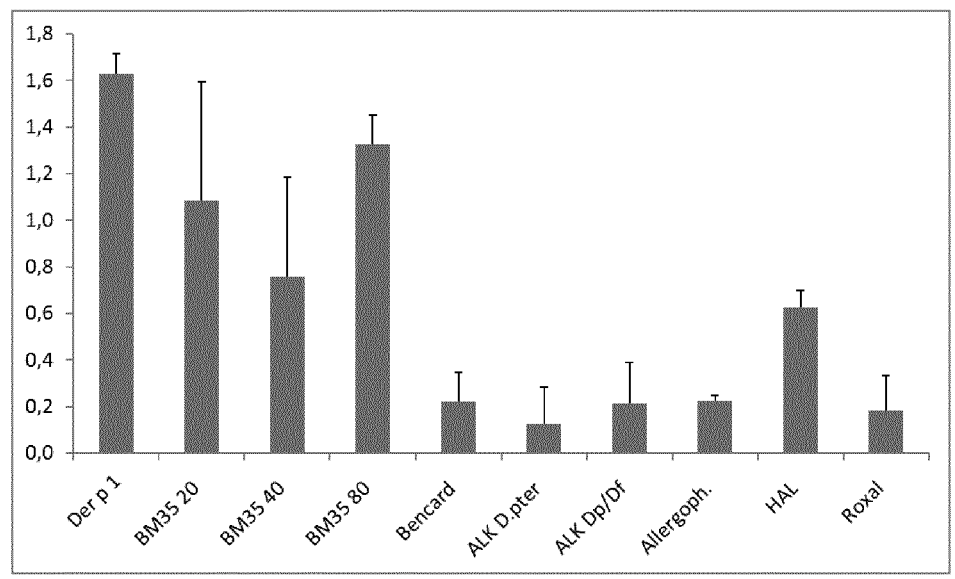
IgG titers after 66 days
Fig. 8A

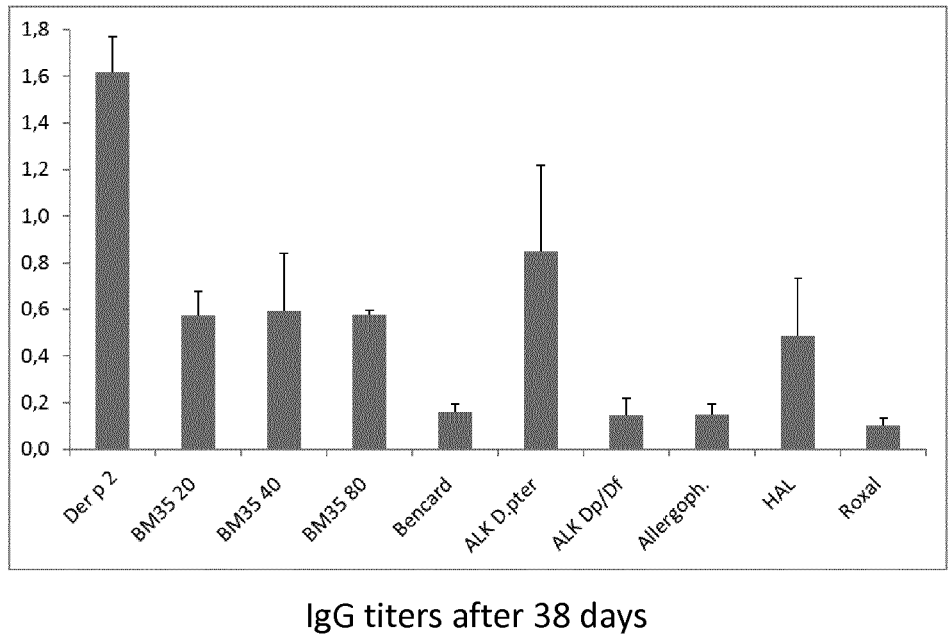
IgG titers after 38 days
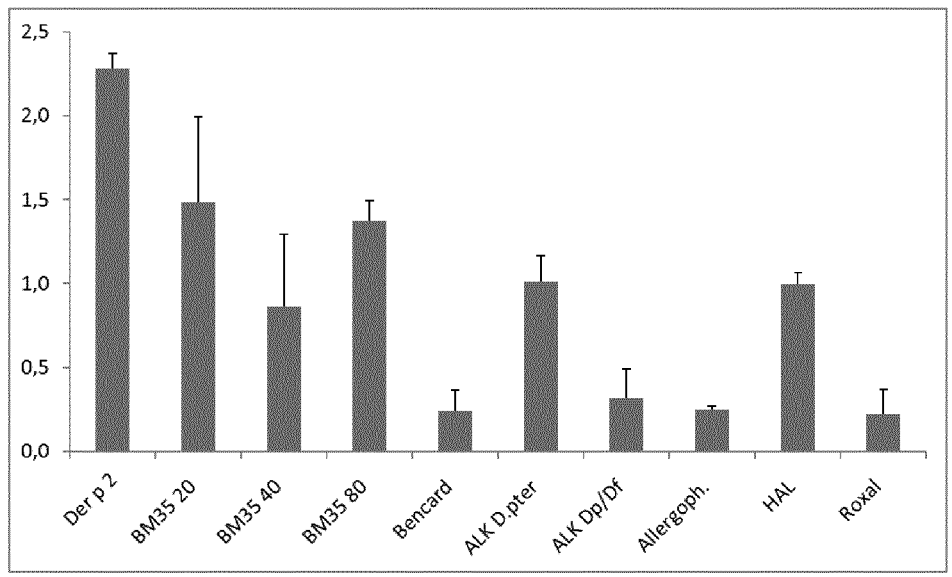
IgG titers after 66 days
Fig. 8B

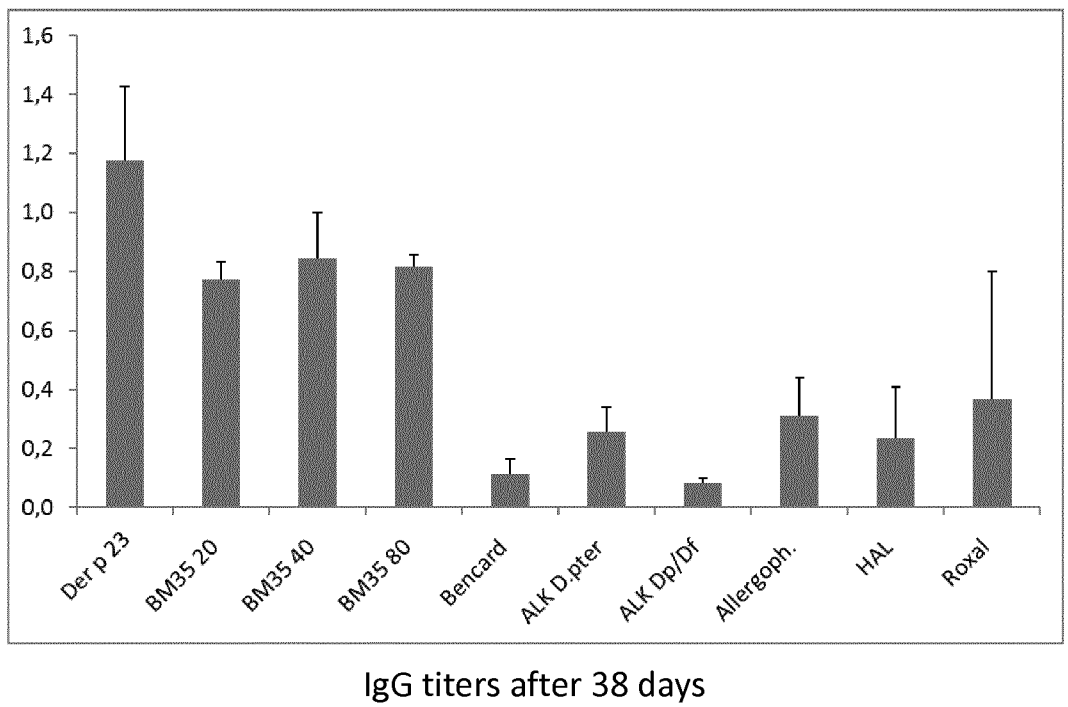
IgG titers after 38 days
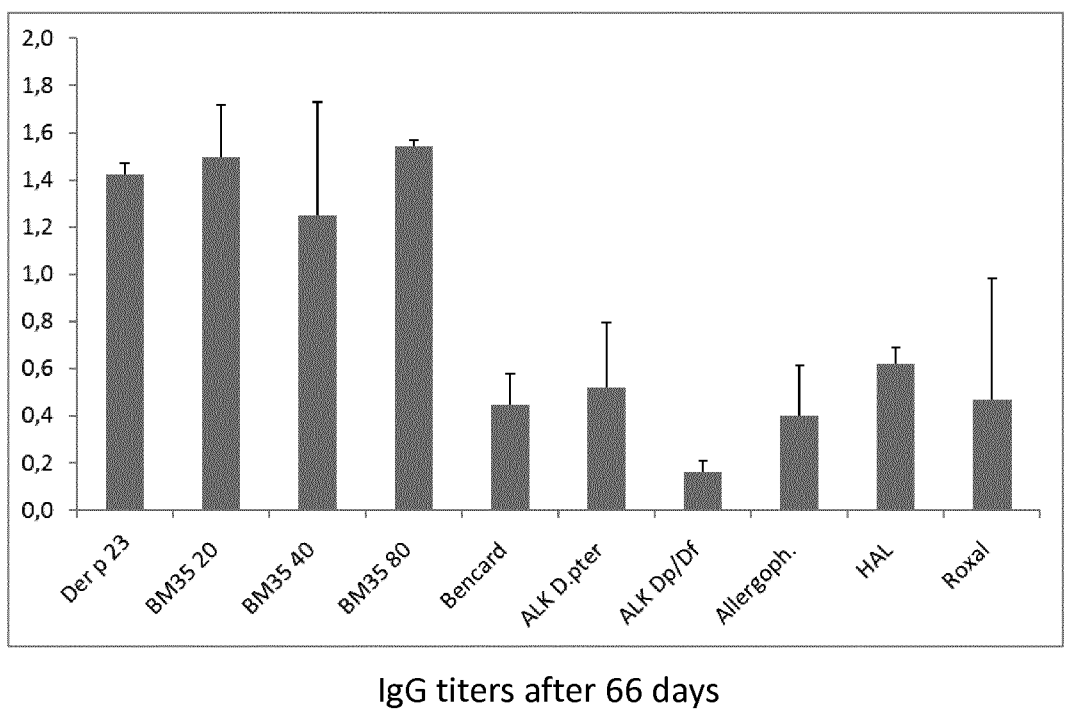
IgG titers after 66 days
Fig. 8C

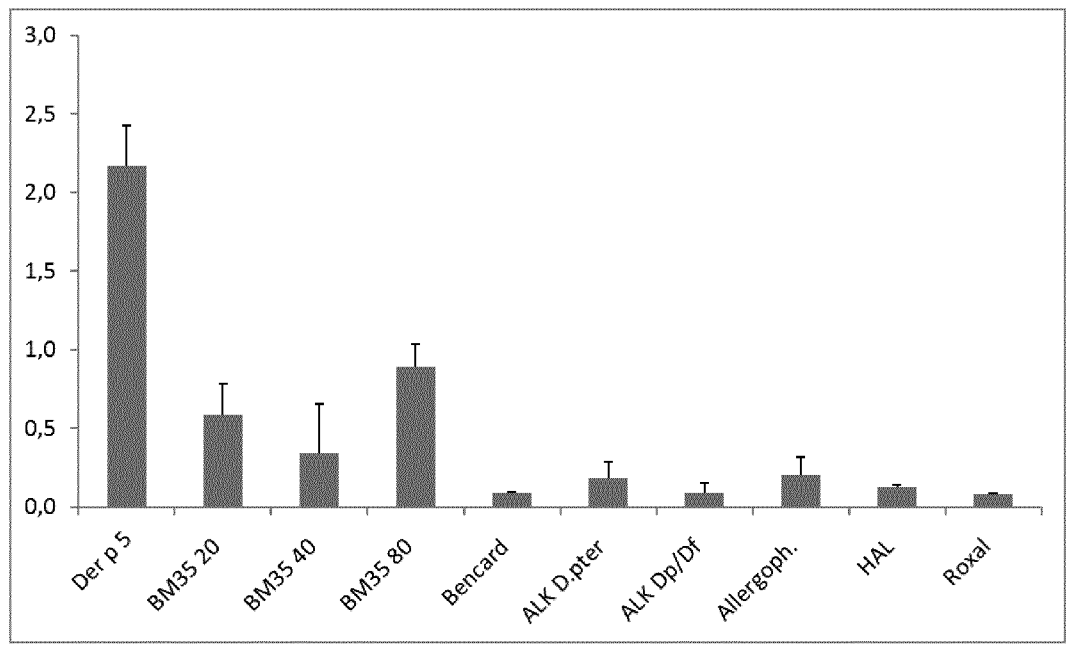
IgG titers after 38 days
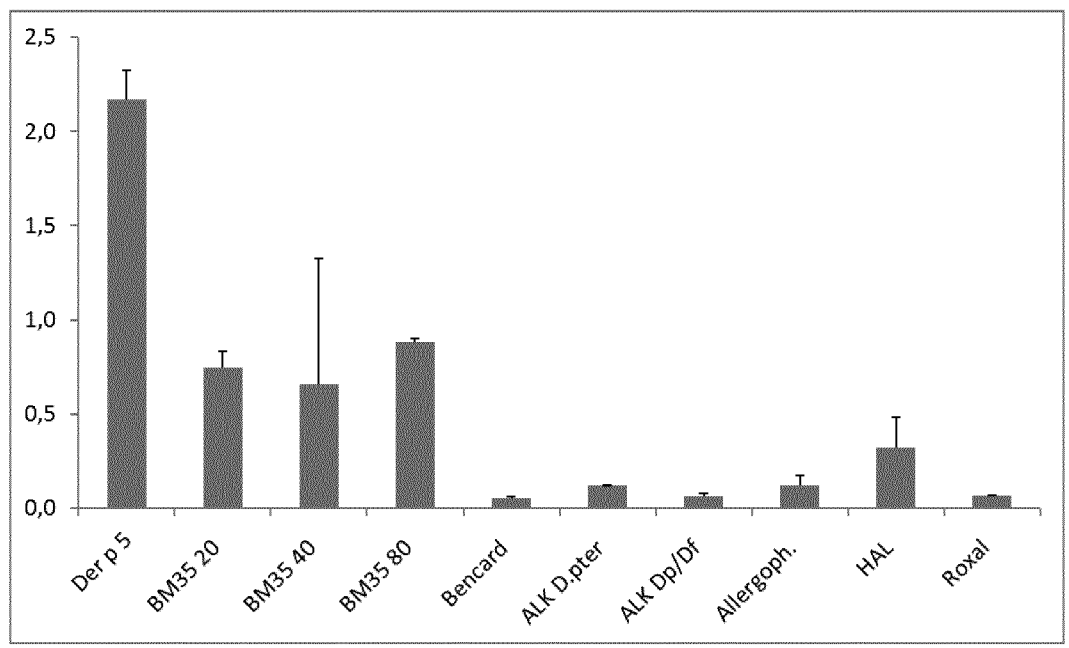
IgG titers after 66 days
Fig. 8D

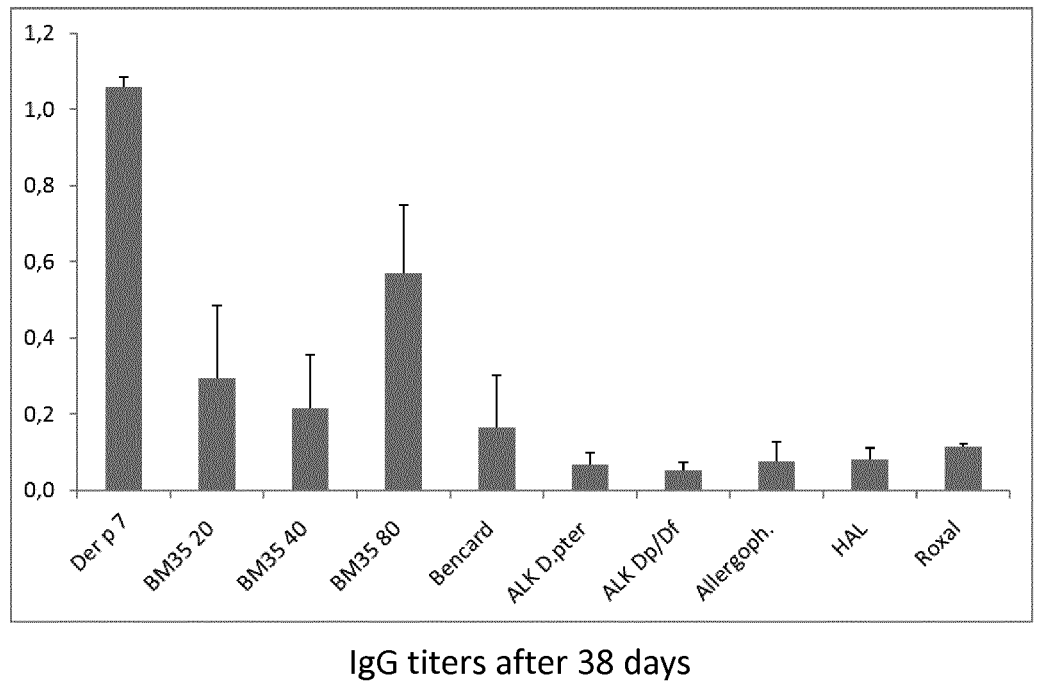
IgG titers after 38 days
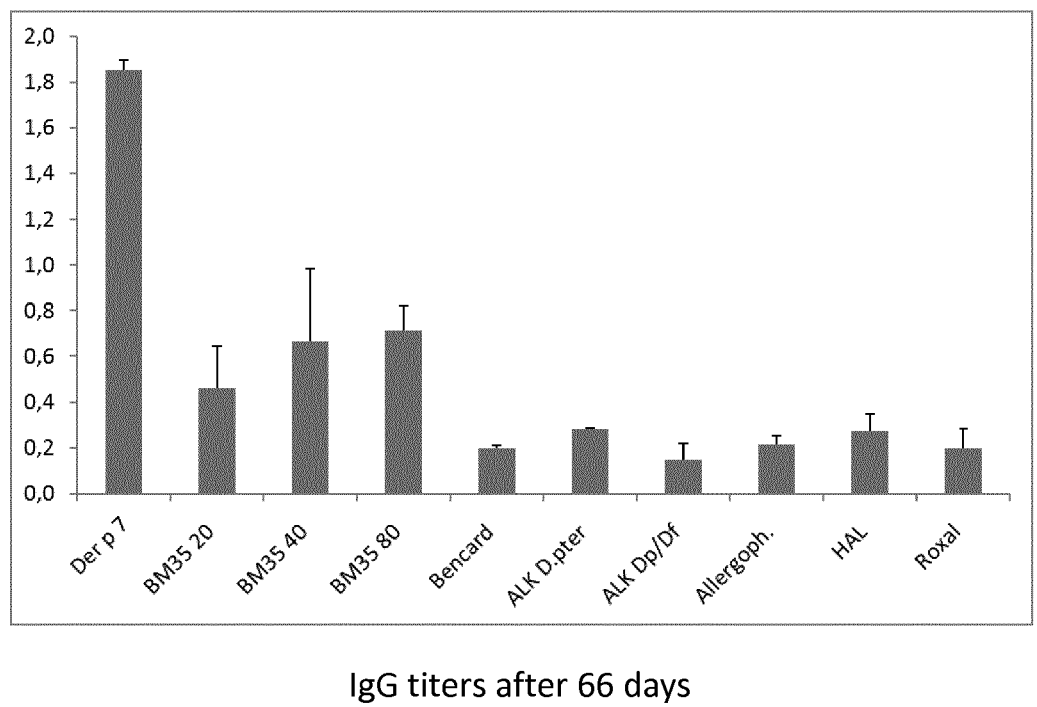
IgG titers after 66 days
Fig. 8E

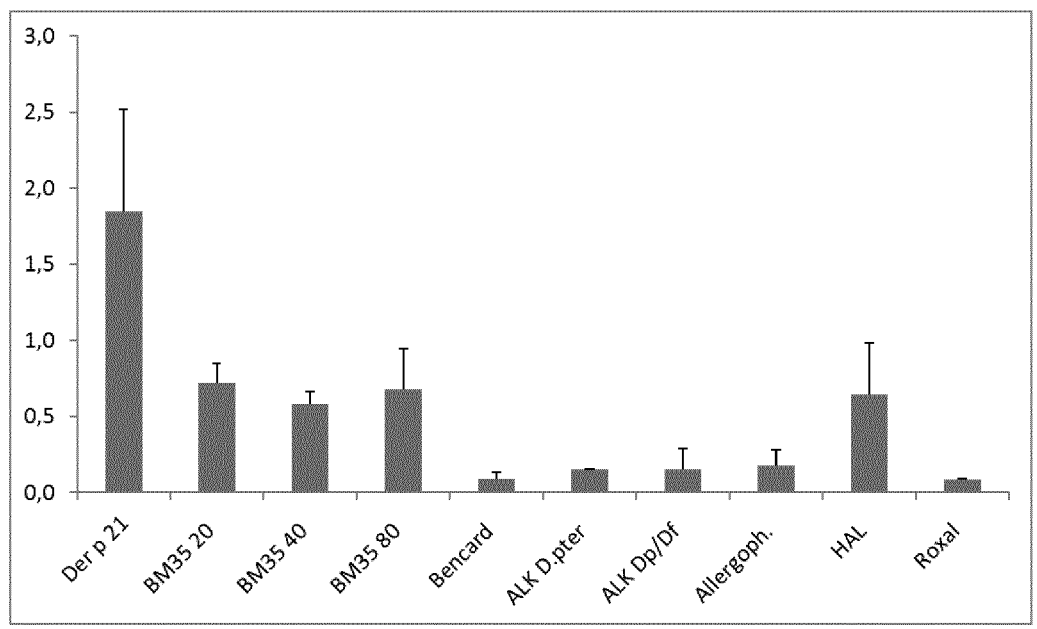
IgG titers after 38 days
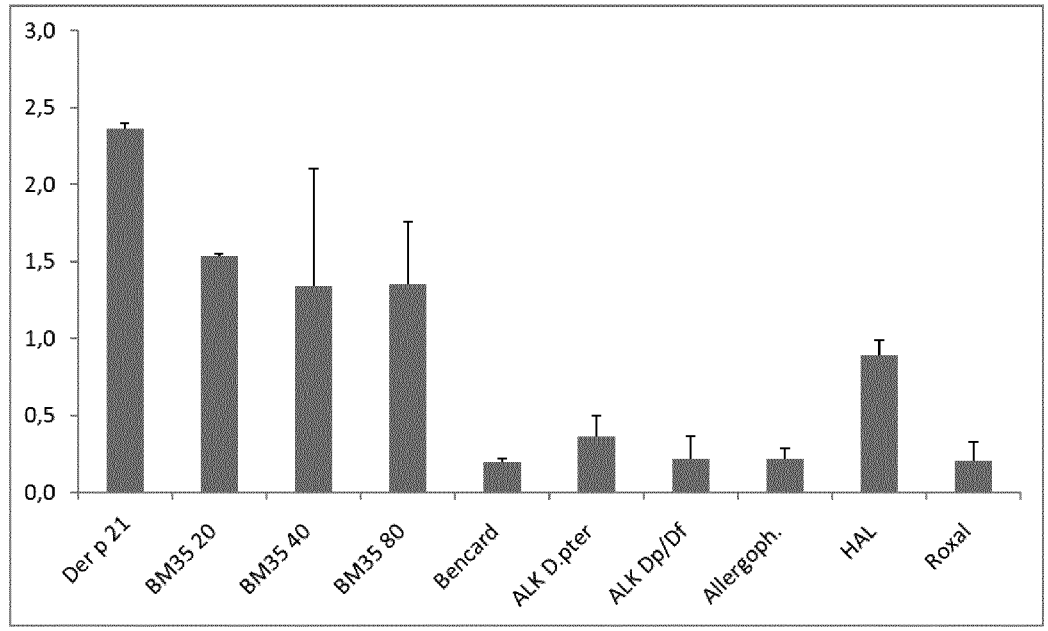
IgG titers after 66 days
Fig. 8F

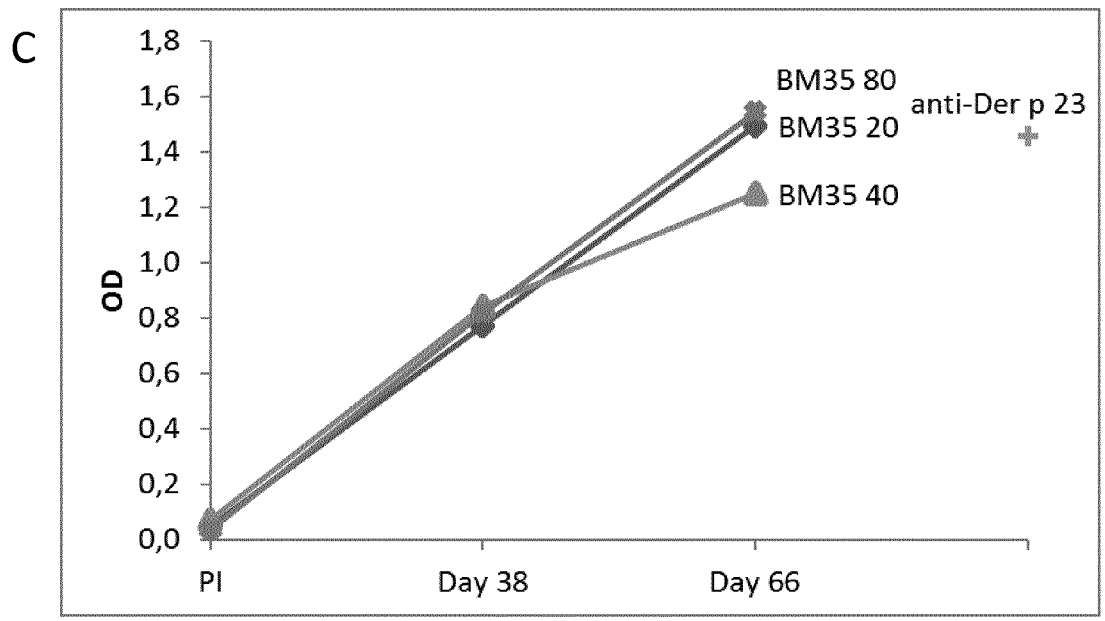
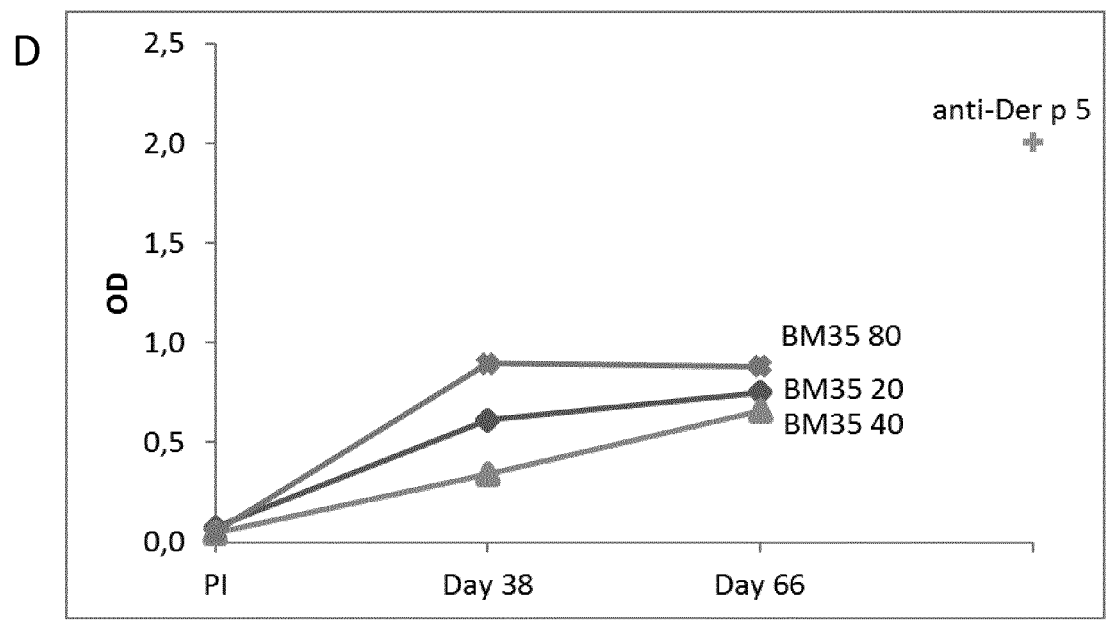
Fig. 9 (continued)

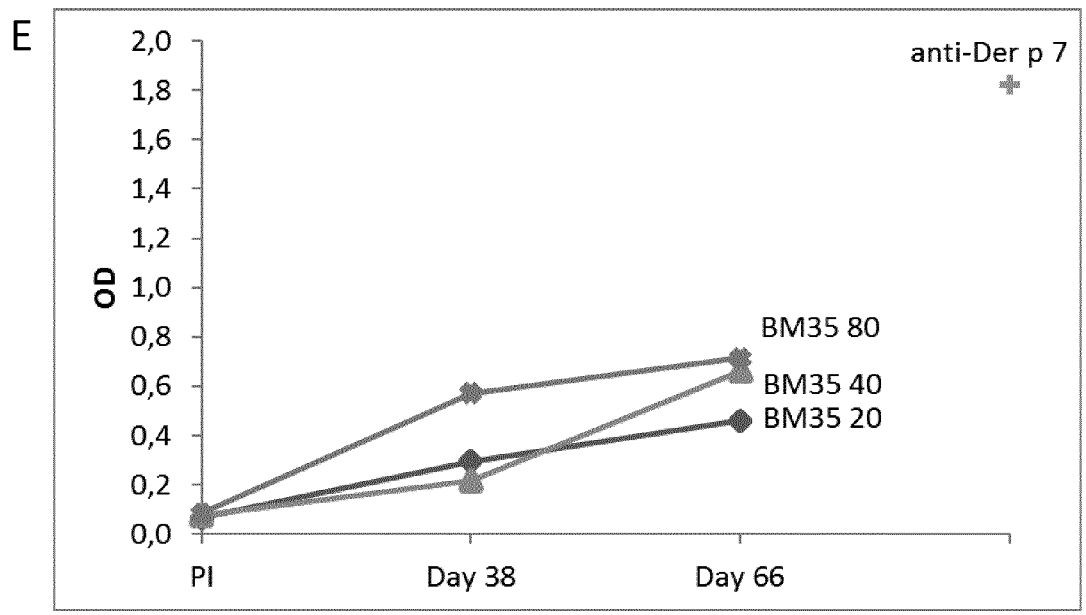
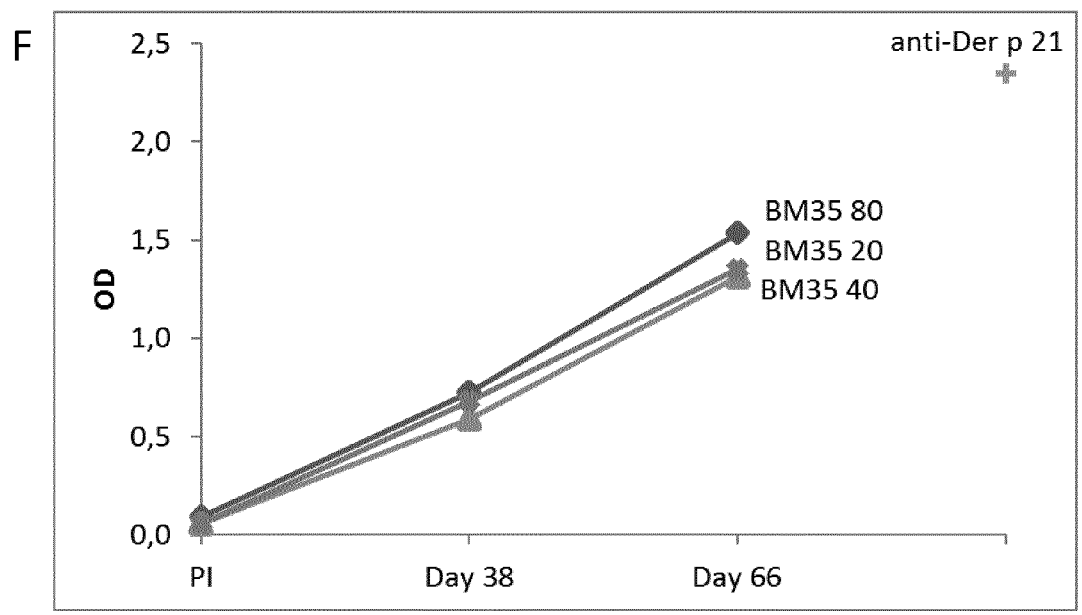
Fig. 9 (continued)

SEQUENCE LISTING

```
<160> NUMBER OF SEQ ID NOS: 81

<210> SEQ ID NO 1
<211> LENGTH: 41
<212> TYPE: PRT
<213> ORGANISM: Artificial Sequence
<220> FEATURE:
<223> OTHER INFORMATION: allergen fragment

<400> SEQUENCE: 1

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala
        35                  40

<210> SEQ ID NO 2
<211> LENGTH: 43
<212> TYPE: PRT
<213> ORGANISM: Artificial Sequence
<220> FEATURE:
<223> OTHER INFORMATION: allergen fragment

<400> SEQUENCE: 2

Ala Thr Glu Ser Ala Tyr Leu Ala Tyr Arg Asn Gln Ser Leu Asp Leu
```

```
                1               5                  10                 15
Ala Glu Gln Glu Leu Val Asp Cys Ala Ser Gln His Gly Cys His Gly
                20                      25                  30

Asp Thr Ile Pro Arg Gly Ile Glu Tyr Ile Gln
            35                      40

<210> SEQ ID NO 3
<211> LENGTH: 31
<212> TYPE: PRT
<213> ORGANISM: Artificial Sequence
<220> FEATURE:
<223> OTHER INFORMATION: allergen fragment

<400> SEQUENCE: 3

His Asn Gly Val Val Gln Glu Ser Tyr Tyr Arg Tyr Val Ala Arg Glu
1               5                  10                  15

Gln Ser Cys Arg Arg Pro Asn Ala Gln Arg Phe Gly Ile Ser Asn
                20                      25                  30

<210> SEQ ID NO 4
<211> LENGTH: 35
<212> TYPE: PRT
<213> ORGANISM: Artificial Sequence
<220> FEATURE:
<223> OTHER INFORMATION: allergen fragment

<400> SEQUENCE: 4

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Tyr Pro Tyr Val
                20                      25                  30

Val Ile Leu
        35

<210> SEQ ID NO 5
<211> LENGTH: 41
<212> TYPE: PRT
<213> ORGANISM: Artificial Sequence
<220> FEATURE:
<223> OTHER INFORMATION: allergen fragment

<400> SEQUENCE: 5

Thr Asn Ala Ser Ser Ile Asn Gly Asn Ala Pro Ala Glu Ile Asp Leu
1               5                   10                  15

Arg Gln Met Arg Thr Val Thr Pro Ile Arg Met Gln Gly Gly Ser Gly
                20                      25                  30

Ser Ser Trp Ala Phe Ser Gly Val Ala
            35                      40

<210> SEQ ID NO 6
<211> LENGTH: 43
<212> TYPE: PRT
<213> ORGANISM: Artificial Sequence
<220> FEATURE:
<223> OTHER INFORMATION: allergen fragment

<400> SEQUENCE: 6

Ala Thr Glu Ser Ala Tyr Leu Ala Tyr Arg Asn Gln Ser Leu Asp Leu
1               5                   10                  15

Ala Glu Gln Glu Leu Val Asp Ser Ala Ser Gln His Gly Ser His Gly
                20                      25                  30

Asp Thr Ile Pro Arg Gly Ile Glu Tyr Ile Gln
```

<210> SEQ ID NO 7
<211> LENGTH: 31
<212> TYPE: PRT
<213> ORGANISM: Artificial Sequence
<220> FEATURE:
<223> OTHER INFORMATION: allergen fragment

<400> SEQUENCE: 7

His Asn Gly Val Val Gln Glu Ser Tyr Tyr Arg Tyr Val Ala Arg Glu
1               5                   10                  15

Gln Ser Ser Arg Arg Pro Asn Ala Gln Arg Phe Gly Ile Ser Asn
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: allergen fragment

<400> SEQUENCE: 8

Cys His Gly Ser Glu Pro Cys Ile Ile His Arg Gly Lys Pro Phe Gln
1               5                   10                  15

Leu Glu Ala Val Phe Glu Ala Asn Gln Asn Ser Lys Thr Ala Lys
            20                  25                  30

<210> SEQ ID NO 9
<211> LENGTH: 42
<212> TYPE: PRT
<213> ORGANISM: Artificial Sequence
<220> FEATURE:
<223> OTHER INFORMATION: allergen fragment

<400> SEQUENCE: 9

Glu Val Asp Val Pro Gly Ile Asp Pro Asn Ala Cys His Tyr Met Lys
1               5                   10                  15

Cys Pro Leu Val Lys Gly Gln Gln Tyr Asp Ile Lys Tyr Thr Trp Ile
            20                  25                  30

Val Pro Lys Ile Ala Pro Lys Ser Glu Asn
            35                  40

<210> SEQ ID NO 10
<211> LENGTH: 30
<212> TYPE: PRT
<213> ORGANISM: Artificial Sequence
<220> FEATURE:
<223> OTHER INFORMATION: allergen fragment

<400> SEQUENCE: 10

His Gly Ser Glu Pro Ser Ile Ile His Arg Gly Lys Pro Phe Gln Leu
1               5                   10                  15

Glu Ala Val Phe Glu Ala Asn Gln Asn Ser Lys Thr Ala Lys
            20                  25                  30

<210> SEQ ID NO 11
<211> LENGTH: 42
<212> TYPE: PRT
<213> ORGANISM: Artificial Sequence
<220> FEATURE:
<223> OTHER INFORMATION: allergen fragment

<400> SEQUENCE: 11

```
Glu Val Asp Val Pro Gly Ile Asp Pro Asn Ala Ser His Tyr Met Lys
1               5                   10                  15

Ser Pro Leu Val Lys Gly Gln Gln Tyr Asp Ile Lys Tyr Thr Trp Ile
            20                  25                  30

Val Pro Lys Ile Ala Pro Lys Ser Glu Asn
        35                  40
```

<210> SEQ ID NO 12
<211> LENGTH: 29
<212> TYPE: PRT
<213> ORGANISM: Artificial Sequence
<220> FEATURE:
<223> OTHER INFORMATION: allergen fragment

<400> SEQUENCE: 12

```
Asp Tyr Gln Asn Glu Phe Asp Phe Leu Leu Met Glu Arg Ile His Glu
1               5                   10                  15

Gln Ile Lys Lys Gly Glu Leu Ala Leu Phe Tyr Leu Gln
            20                  25
```

<210> SEQ ID NO 13
<211> LENGTH: 31
<212> TYPE: PRT
<213> ORGANISM: Artificial Sequence
<220> FEATURE:
<223> OTHER INFORMATION: allergen fragment

<400> SEQUENCE: 13

```
Glu Gln Tyr Asn Leu Glu Met Ala Lys Lys Ser Gly Asp Ile Leu Glu
1               5                   10                  15

Arg Asp Leu Lys Lys Glu Glu Ala Arg Val Lys Lys Ile Glu Val
            20                  25                  30
```

<210> SEQ ID NO 14
<211> LENGTH: 30
<212> TYPE: PRT
<213> ORGANISM: Artificial Sequence
<220> FEATURE:
<223> OTHER INFORMATION: allergen fragment

<400> SEQUENCE: 14

```
Asp Pro Ile His Tyr Asp Lys Ile Thr Glu Glu Ile Asn Lys Ala Val
1               5                   10                  15

Asp Glu Ala Val Ala Ala Ile Glu Lys Ser Glu Thr Phe Asp
            20                  25                  30
```

<210> SEQ ID NO 15
<211> LENGTH: 33
<212> TYPE: PRT
<213> ORGANISM: Artificial Sequence
<220> FEATURE:
<223> OTHER INFORMATION: allergen fragment

<400> SEQUENCE: 15

```
Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr
```

<210> SEQ ID NO 16
<211> LENGTH: 39
<212> TYPE: PRT

<213> ORGANISM: Artificial Sequence
<220> FEATURE:
<223> OTHER INFORMATION: allergen fragment

<400> SEQUENCE: 16

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Arg Trp Asn
            20                  25                  30

Glu Asp Glu Glu Thr Cys Thr
        35

<210> SEQ ID NO 17
<211> LENGTH: 39
<212> TYPE: PRT
<213> ORGANISM: Artificial Sequence
<220> FEATURE:
<223> OTHER INFORMATION: allergen fragment

<400> SEQUENCE: 17

Gly Tyr Phe Ala Asp Pro Lys Asp Pro His Lys Phe Tyr Ile Ser Ser
1               5                   10                  15

Asn Trp Glu Ala Val His Lys Asp Ser Pro Gly Asn Thr Arg Trp Asn
            20                  25                  30

Glu Asp Glu Glu Thr Ser Thr
        35

<210> SEQ ID NO 18
<211> LENGTH: 192
<212> TYPE: PRT
<213> ORGANISM: Artificial Sequence
<220> FEATURE:
<223> OTHER INFORMATION: fusion protein

<400> SEQUENCE: 18

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
            20                  25                  30

Val Ile Leu His Asn Gly Val Val Gln Glu Ser Tyr Tyr Arg Tyr Val
        35                  40                  45

Ala Arg Glu Gln Ser Ser Arg Arg Pro Asn Ala Gln Arg Phe Gly Ile
    50                  55                  60

Ser Asn His Gly Ser Glu Pro Ser Ile Ile His Arg Gly Lys Pro Phe
65                  70                  75                  80

Gln Leu Glu Ala Val Phe Glu Ala Asn Gln Asn Ser Lys Thr Ala Lys
                85                  90                  95

His Gly Ser Glu Pro Ser Ile Ile His Arg Gly Lys Pro Phe Gln Leu
            100                 105                 110

Glu Ala Val Phe Glu Ala Asn Gln Asn Ser Lys Thr Ala Lys Val Arg
        115                 120                 125

Asn Ser Trp Asp Thr Asn Trp Gly Asp Asn Gly Tyr Gly Tyr Phe Ala
    130                 135                 140

Ala Asn Ile Asp Leu Met Met Ile Glu Glu Tyr Pro Tyr Val Val Ile
145                 150                 155                 160

Leu His Asn Gly Val Val Gln Glu Ser Tyr Tyr Arg Tyr Val Ala Arg
                165                 170                 175

Glu Gln Ser Ser Arg Arg Pro Asn Ala Gln Arg Phe Gly Ile Ser Asn
            180                 185                 190

<210> SEQ ID NO 19
<211> LENGTH: 250
<212> TYPE: PRT
<213> ORGANISM: Artificial Sequence
<220> FEATURE:
<223> OTHER INFORMATION: fusion protein

<400> SEQUENCE: 19

```
Glu Val Asp Val Pro Gly Ile Asp Pro Asn Ala Ser His Tyr Met Lys
1               5                   10                  15

Ser Pro Leu Val Lys Gly Gln Gln Tyr Asp Ile Lys Tyr Thr Trp Ile
            20                  25                  30

Val Pro Lys Ile Ala Pro Lys Ser Glu Asn Glu Val Asp Val Pro Gly
        35                  40                  45

Ile Asp Pro Asn Ala Ser His Tyr Met Lys Ser Pro Leu Val Lys Gly
    50                  55                  60

Gln Gln Tyr Asp Ile Lys Tyr Thr Trp Ile Val Pro Lys Ile Ala Pro
65                  70                  75                  80

Lys Ser Glu Asn Ala Thr Glu Ser Ala Tyr Leu Ala Tyr Arg Asn Gln
                85                  90                  95

Ser Leu Asp Leu Ala Glu Gln Glu Leu Val Asp Ser Ala Ser Gln His
            100                 105                 110

Gly Ser His Gly Asp Thr Ile Pro Arg Gly Ile Glu Tyr Ile Gln Thr
        115                 120                 125

Asn Ala Ser Ser Ile Asn Gly Asn Ala Pro Ala Glu Ile Asp Leu Arg
    130                 135                 140

Gln Met Arg Thr Val Thr Pro Ile Arg Met Gln Gly Gly Ser Gly Ser
145                 150                 155                 160

Ser Trp Ala Phe Ser Gly Val Ala Ala Thr Glu Ser Ala Tyr Leu Ala
                165                 170                 175

Tyr Arg Asn Gln Ser Leu Asp Leu Ala Glu Gln Glu Leu Val Asp Ser
            180                 185                 190

Ala Ser Gln His Gly Ser His Gly Asp Thr Ile Pro Arg Gly Ile Glu
        195                 200                 205

Tyr Ile Gln Thr Asn Ala Ser Ser Ile Asn Gly Asn Ala Pro Ala Glu
    210                 215                 220

Ile Asp Leu Arg Gln Met Arg Thr Val Thr Pro Ile Arg Met Gln Gly
225                 230                 235                 240

Gly Ser Gly Ser Ser Trp Ala Phe Ser Gly
                245                 250
```

<210> SEQ ID NO 20
<211> LENGTH: 216
<212> TYPE: PRT
<213> ORGANISM: Artificial Sequence
<220> FEATURE:
<223> OTHER INFORMATION: fusion protein

<400> SEQUENCE: 20

```
Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr Tyr Asn Tyr Glu Phe Ala Leu Glu Ser Ile Lys Leu Leu Ile Lys
        35                  40                  45

Lys Leu Asp Glu Leu Ala Lys Lys Val Lys Ala Val Asn Pro Asp Glu
```

```
                50                  55                  60
Tyr Tyr Tyr Asn Tyr Glu Phe Ala Leu Glu Ser Ile Lys Leu Leu Ile
 65                  70                  75                  80

Lys Lys Leu Asp Glu Leu Ala Lys Lys Val Lys Ala Val Asn Pro Asp
                 85                  90                  95

Glu Tyr Tyr Gly Tyr Phe Ala Asp Pro Lys Asp Pro His Lys Phe Tyr
                100                 105                 110

Ile Ser Ser Asn Trp Glu Ala Val His Lys Asp Ser Pro Gly Asn Thr
                115                 120                 125

Arg Trp Asn Glu Asp Glu Glu Thr Ser Thr Gly Tyr Phe Ala Asp Pro
130                 135                 140

Lys Asp Pro His Lys Phe Tyr Ile Ser Ser Asn Trp Glu Ala Val His
145                 150                 155                 160

Lys Asp Ser Pro Gly Asn Thr Arg Trp Asn Glu Asp Glu Glu Thr Ser
                165                 170                 175

Thr Gly Tyr Phe Ala Asp Pro Lys Asp Pro His Lys Phe Tyr Ile Ser
                180                 185                 190

Ser Asn Trp Glu Ala Val His Lys Asp Ser Pro Gly Asn Thr Arg Trp
                195                 200                 205

Asn Glu Asp Glu Glu Thr Ser Thr
210                 215

<210> SEQ ID NO 21
<211> LENGTH: 180
<212> TYPE: PRT
<213> ORGANISM: Artificial Sequence
<220> FEATURE:
<223> OTHER INFORMATION: fusion protein

<400> SEQUENCE: 21

Asp Tyr Gln Asn Glu Phe Asp Phe Leu Leu Met Glu Arg Ile His Glu
 1               5                  10                  15

Gln Ile Lys Lys Gly Glu Leu Ala Leu Phe Tyr Leu Gln Asp Tyr Gln
                 20                  25                  30

Asn Glu Phe Asp Phe Leu Leu Met Glu Arg Ile His Glu Gln Ile Lys
                 35                  40                  45

Lys Gly Glu Leu Ala Leu Phe Tyr Leu Gln Asp Pro Ile His Tyr Asp
 50                  55                  60

Lys Ile Thr Glu Glu Ile Asn Lys Ala Val Asp Glu Ala Val Ala Ala
 65                  70                  75                  80

Ile Glu Lys Ser Glu Thr Phe Asp Asp Pro Ile His Tyr Asp Lys Ile
                 85                  90                  95

Thr Glu Glu Ile Asn Lys Ala Val Asp Glu Ala Val Ala Ala Ile Glu
                100                 105                 110

Lys Ser Glu Thr Phe Asp Glu Gln Tyr Asn Leu Glu Met Ala Lys Lys
                115                 120                 125

Ser Gly Asp Ile Leu Glu Arg Asp Leu Lys Lys Glu Ala Arg Val
                130                 135                 140

Lys Lys Ile Glu Val Glu Gln Tyr Asn Leu Glu Met Ala Lys Lys Ser
145                 150                 155                 160

Gly Asp Ile Leu Glu Arg Asp Leu Lys Lys Glu Ala Arg Val Lys
                165                 170                 175

Lys Ile Glu Val
                180
```

<210> SEQ ID NO 22
<211> LENGTH: 192
<212> TYPE: PRT
<213> ORGANISM: Artificial Sequence
<220> FEATURE:
<223> OTHER INFORMATION: fusion protein

<400> SEQUENCE: 22

```
Val Arg Asn Ser Trp Asp Thr Thr Trp Gly Asp Ser Gly Tyr Gly Tyr
1               5                   10                  15

Phe Gln Ala Gly Asn Asn Leu Met Met Ile Glu Gln Tyr Pro Tyr Val
            20                  25                  30

Val Ile Met Gln Asn Gly Val Val Glu Glu Arg Ser Tyr Pro Tyr Val
        35                  40                  45

Ala Arg Glu Gln Gln Cys Arg Arg Pro Asn Ser Gln His Tyr Gly Ile
    50                  55                  60

Ser Asn His Gly Ser Asp Pro Cys Ile Ile His Arg Gly Lys Pro Phe
65                  70                  75                  80

Asn Leu Glu Ala Ile Phe Asp Ala Asn Gln Asn Thr Lys Thr Ala Lys
                85                  90                  95

His Gly Ser Asp Pro Cys Ile Ile His Arg Gly Lys Pro Phe Asn Leu
            100                 105                 110

Glu Ala Ile Phe Asp Ala Asn Gln Asn Thr Lys Thr Ala Lys Val Arg
        115                 120                 125

Asn Ser Trp Asp Thr Thr Trp Gly Asp Ser Gly Tyr Gly Tyr Phe Gln
    130                 135                 140

Ala Gly Asn Asn Leu Met Met Ile Glu Gln Tyr Pro Tyr Val Val Ile
145                 150                 155                 160

Met Gln Asn Gly Val Val Glu Glu Arg Ser Tyr Pro Tyr Val Ala Arg
                165                 170                 175

Glu Gln Gln Cys Arg Arg Pro Asn Ser Gln His Tyr Gly Ile Ser Asn
            180                 185                 190
```

<210> SEQ ID NO 23
<211> LENGTH: 254
<212> TYPE: PRT
<213> ORGANISM: Artificial Sequence
<220> FEATURE:
<223> OTHER INFORMATION: fusion protein

<400> SEQUENCE: 23

```
Glu Val Asp Val Pro Gly Ile Asp Thr Asn Ala Cys His Tyr Ile Lys
1               5                   10                  15

Cys Pro Leu Val Lys Gly Gln Gln Tyr Asp Ala Lys Tyr Thr Trp Asn
            20                  25                  30

Val Pro Lys Ile Ala Pro Lys Ser Glu Asn Glu Val Asp Val Pro Gly
        35                  40                  45

Ile Asp Thr Asn Ala Cys His Tyr Ile Lys Cys Pro Leu Val Lys Gly
    50                  55                  60

Gln Gln Tyr Asp Ala Lys Tyr Thr Trp Asn Val Pro Lys Ile Ala Pro
65                  70                  75                  80

Lys Ser Glu Asn Ala Thr Glu Ser Ala Tyr Leu Ala Tyr Arg Asn Thr
                85                  90                  95

Ser Leu Asp Leu Ser Glu Gln Glu Leu Val Asp Cys Ala Ser Gln His
            100                 105                 110

Gly Cys His Gly Asp Thr Ile Pro Arg Gly Ile Glu Tyr Ile Gln Thr
        115                 120                 125
```

```
Ser Ala Cys Arg Ile Asn Ser Val Asn Val Pro Ser Glu Leu Asp Leu
130                 135                 140

Arg Ser Leu Arg Thr Val Thr Pro Ile Arg Met Gln Gly Gly Cys Gly
145                 150                 155                 160

Ser Cys Trp Ala Phe Ser Gly Val Ala Ala Thr Glu Ser Ala Tyr Leu
                165                 170                 175

Ala Tyr Arg Asn Thr Ser Leu Asp Leu Ser Glu Gln Glu Leu Val Asp
            180                 185                 190

Cys Ala Ser Gln His Gly Cys His Gly Asp Thr Ile Pro Arg Gly Ile
        195                 200                 205

Glu Tyr Ile Gln Thr Ser Ala Cys Arg Ile Asn Ser Val Asn Val Pro
210                 215                 220

Ser Glu Leu Asp Leu Arg Ser Leu Arg Thr Val Thr Pro Ile Arg Met
225                 230                 235                 240

Gln Gly Gly Cys Gly Ser Cys Trp Ala Phe Ser Gly Val Ala
                245                 250
```

<210> SEQ ID NO 24
<211> LENGTH: 210
<212> TYPE: PRT
<213> ORGANISM: Artificial Sequence
<220> FEATURE:
<223> OTHER INFORMATION: fusion protein

<400> SEQUENCE: 24

```
Tyr Asn Phe Glu Thr Ala Val Ser Thr Ile Glu Ile Leu Val Lys Asp
1               5                   10                  15

Leu Ala Glu Leu Ala Lys Lys Val Lys Ala Val Lys Ser Asp Asp Tyr
            20                  25                  30

Asn Phe Glu Thr Ala Val Ser Thr Ile Glu Ile Leu Val Lys Asp Leu
        35                  40                  45

Ala Glu Leu Ala Lys Lys Val Lys Ala Val Lys Ser Asp Asp Tyr Asn
    50                  55                  60

Phe Glu Thr Ala Val Ser Thr Ile Glu Ile Leu Val Lys Asp Leu Ala
65                  70                  75                  80

Glu Leu Ala Lys Lys Val Lys Ala Val Lys Ser Asp Asp Gly Tyr Phe
                85                  90                  95

Ala Asp Pro Lys Asp Pro Cys Lys Phe Tyr Ile Cys Ser Asn Trp Glu
            100                 105                 110

Ala Ile His Lys Ser Cys Pro Gly Asn Thr Arg Trp Asn Glu Lys Glu
        115                 120                 125

Leu Thr Cys Thr Gly Tyr Phe Ala Asp Pro Lys Asp Pro Cys Lys Phe
    130                 135                 140

Tyr Ile Cys Ser Asn Trp Glu Ala Ile His Lys Ser Cys Pro Gly Asn
145                 150                 155                 160

Thr Arg Trp Asn Glu Lys Glu Leu Thr Cys Thr Gly Tyr Phe Ala Asp
                165                 170                 175

Pro Lys Asp Pro Cys Lys Phe Tyr Ile Cys Ser Asn Trp Glu Ala Ile
            180                 185                 190

His Lys Ser Cys Pro Gly Asn Thr Arg Trp Asn Glu Lys Glu Leu Thr
        195                 200                 205

Cys Thr
    210
```

<210> SEQ ID NO 25
<211> LENGTH: 180

```
<212> TYPE: PRT
<213> ORGANISM: Artificial Sequence
<220> FEATURE:
<223> OTHER INFORMATION: fusion protein

<400> SEQUENCE: 25

Asp Tyr Gln Asn Glu Phe Asp Phe Leu Leu Met Gln Arg Ile His Glu
1               5                   10                  15

Gln Met Arg Lys Gly Glu Glu Ala Leu Leu His Leu Gln Asp Tyr Gln
                20                  25                  30

Asn Glu Phe Asp Phe Leu Leu Met Gln Arg Ile His Glu Gln Met Arg
            35                  40                  45

Lys Gly Glu Glu Ala Leu Leu His Leu Gln Asp Pro Ile His Tyr Asp
    50                  55                  60

Lys Ile Thr Glu Glu Ile Asn Lys Ala Ile Asp Asp Ala Ile Ala Ala
65                  70                  75                  80

Ile Glu Gln Ser Glu Thr Ile Asp Asp Pro Ile His Tyr Asp Lys Ile
                85                  90                  95

Thr Glu Glu Ile Asn Lys Ala Ile Asp Asp Ala Ile Ala Ala Ile Glu
            100                 105                 110

Gln Ser Glu Thr Ile Asp Glu Arg Tyr Asn Val Glu Ile Ala Leu Lys
    115                 120                 125

Ser Asn Glu Ile Leu Glu Arg Asp Leu Lys Lys Glu Gln Arg Val
130                 135                 140

Lys Lys Ile Glu Val Glu Arg Tyr Asn Val Glu Ile Ala Leu Lys Ser
145                 150                 155                 160

Asn Glu Ile Leu Glu Arg Asp Leu Lys Lys Glu Gln Arg Val Lys
                165                 170                 175

Lys Ile Glu Val
            180

<210> SEQ ID NO 26
<211> LENGTH: 173
<212> TYPE: PRT
<213> ORGANISM: Artificial Sequence
<220> FEATURE:
<223> OTHER INFORMATION: PreS carrier protein

<400> SEQUENCE: 26

Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
                20                  25                  30

Phe Gly Ala Asn Ser Asn Asn Pro Asp Trp Asp Phe Asn Pro Ile Lys
            35                  40                  45

Asp His Trp Pro Ala Ala Asn Gln Val Gly Val Gly Ala Phe Gly Pro
    50                  55                  60

Gly Leu Thr Pro Pro His Gly Gly Ile Leu Gly Trp Ser Pro Gln Ala
65                  70                  75                  80

Gln Gly Ile Leu Thr Thr Val Ser Thr Ile Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
    115                 120                 125

Ala Leu Gln Asp Pro Arg Val Arg Gly Leu Tyr Phe Pro Ala Gly Gly
130                 135                 140
```

```
Ser Ser Ser Gly Thr Val Asn Pro Ala Pro Asn Ile Ala Ser His Ile
145                 150                 155                 160

Ser Ser Ile Ser Ala Arg Thr Gly Asp Pro Val Thr Asn
                165                 170

<210> SEQ ID NO 27
<211> LENGTH: 615
<212> TYPE: PRT
<213> ORGANISM: Artificial Sequence
<220> FEATURE:
<223> OTHER INFORMATION: fusion protein

<400> SEQUENCE: 27

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
                20                  25                  30

Val Ile Leu His Asn Gly Val Val Gln Glu Ser Tyr Tyr Arg Tyr Val
            35                  40                  45

Ala Arg Glu Gln Ser Ser Arg Arg Pro Asn Ala Gln Arg Phe Gly Ile
    50                  55                  60

Ser Asn His Gly Ser Glu Pro Ser Ile Ile His Arg Gly Lys Pro Phe
65                  70                  75                  80

Gln Leu Glu Ala Val Phe Glu Ala Asn Gln Asn Ser Lys Thr Ala Lys
                85                  90                  95

His Gly Ser Glu Pro Ser Ile Ile His Arg Gly Lys Pro Phe Gln Leu
            100                 105                 110

Glu Ala Val Phe Glu Ala Asn Gln Asn Ser Lys Thr Ala Lys Val Arg
        115                 120                 125

Asn Ser Trp Asp Thr Asn Trp Gly Asp Asn Gly Tyr Gly Tyr Phe Ala
130                 135                 140

Ala Asn Ile Asp Leu Met Met Ile Glu Glu Tyr Pro Tyr Val Val Ile
145                 150                 155                 160

Leu His Asn Gly Val Val Gln Glu Ser Tyr Tyr Arg Tyr Val Ala Arg
                165                 170                 175

Glu Gln Ser Ser Arg Arg Pro Asn Ala Gln Arg Phe Gly Ile Ser Asn
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Ala Ser Thr
        275                 280                 285

Asn Arg Gln Ser Gly Arg Gln Pro Thr Pro Ile Ser Pro Pro Leu Arg
290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335
```

```
Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Glu Val Asp
            355                 360                 365

Val Pro Gly Ile Asp Pro Asn Ala Ser His Tyr Met Lys Ser Pro Leu
370                 375                 380

Val Lys Gly Gln Gln Tyr Asp Ile Lys Tyr Thr Trp Ile Val Pro Lys
385                 390                 395                 400

Ile Ala Pro Lys Ser Glu Asn Glu Val Asp Val Pro Gly Ile Asp Pro
                405                 410                 415

Asn Ala Ser His Tyr Met Lys Ser Pro Leu Val Lys Gly Gln Gln Tyr
                420                 425                 430

Asp Ile Lys Tyr Thr Trp Ile Val Pro Lys Ile Ala Pro Lys Ser Glu
            435                 440                 445

Asn Ala Thr Glu Ser Ala Tyr Leu Ala Tyr Arg Asn Gln Ser Leu Asp
        450                 455                 460

Leu Ala Glu Gln Glu Leu Val Asp Ser Ala Ser Gln His Gly Ser His
465                 470                 475                 480

Gly Asp Thr Ile Pro Arg Gly Ile Glu Tyr Ile Gln Thr Asn Ala Ser
                485                 490                 495

Ser Ile Asn Gly Asn Ala Pro Ala Glu Ile Asp Leu Arg Gln Met Arg
            500                 505                 510

Thr Val Thr Pro Ile Arg Met Gln Gly Gly Ser Gly Ser Ser Trp Ala
            515                 520                 525

Phe Ser Gly Val Ala Ala Thr Glu Ser Ala Tyr Leu Ala Tyr Arg Asn
530                 535                 540

Gln Ser Leu Asp Leu Ala Glu Gln Glu Leu Val Asp Ser Ala Ser Gln
545                 550                 555                 560

His Gly Ser His Gly Asp Thr Ile Pro Arg Gly Ile Glu Tyr Ile Gln
                565                 570                 575

Thr Asn Ala Ser Ser Ile Asn Gly Asn Ala Pro Ala Glu Ile Asp Leu
            580                 585                 590

Arg Gln Met Arg Thr Val Thr Pro Ile Arg Met Gln Gly Gly Ser Gly
            595                 600                 605

Ser Ser Trp Ala Phe Ser Gly
            610                 615

<210> SEQ ID NO 28
<211> LENGTH: 569
<212> TYPE: PRT
<213> ORGANISM: Artificial Sequence
<220> FEATURE:
<223> OTHER INFORMATION: fusion protein

<400> SEQUENCE: 28

Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr Tyr Asn Tyr Glu Phe Ala Leu Glu Ser Ile Lys Leu Leu Ile Lys
        35                  40                  45

Lys Leu Asp Glu Leu Ala Lys Lys Val Lys Ala Val Asn Pro Asp Glu
    50                  55                  60

Tyr Tyr Tyr Asn Tyr Glu Phe Ala Leu Glu Ser Ile Lys Leu Leu Ile
65                  70                  75                  80
```

-continued

```
Lys Lys Leu Asp Glu Leu Ala Lys Lys Val Lys Ala Val Asn Pro Asp
                85                  90                  95
Glu Tyr Tyr Gly Tyr Phe Ala Asp Pro Lys Asp Pro His Lys Phe Tyr
            100                 105                 110
Ile Ser Ser Asn Trp Glu Ala Val His Lys Asp Ser Pro Gly Asn Thr
        115                 120                 125
Arg Trp Asn Glu Asp Glu Glu Thr Ser Thr Gly Tyr Phe Ala Asp Pro
    130                 135                 140
Lys Asp Pro His Lys Phe Tyr Ile Ser Ser Asn Trp Glu Ala Val His
145                 150                 155                 160
Lys Asp Ser Pro Gly Asn Thr Arg Trp Asn Glu Asp Glu Glu Thr Ser
                165                 170                 175
Thr Gly Tyr Phe Ala Asp Pro Lys Asp Pro His Lys Phe Tyr Ile Ser
            180                 185                 190
Ser Asn Trp Glu Ala Val His Lys Asp Ser Pro Gly Asn Thr Arg Trp
        195                 200                 205
Asn Glu Asp Glu Glu Thr Ser Thr Gly Gly Trp Ser Ser Lys Pro Arg
    210                 215                 220
Lys Gly Met Gly Thr Asn Leu Ser Val Pro Asn Pro Leu Gly Phe Phe
225                 230                 235                 240
Pro Asp His Gln Leu Asp Pro Ala Phe Gly Ala Asn Ser Asn Asn Pro
                245                 250                 255
Asp Trp Asp Phe Asn Pro Ile Lys Asp His Trp Pro Ala Ala Asn Gln
            260                 265                 270
Val Gly Val Gly Ala Phe Gly Pro Gly Leu Thr Pro Pro His Gly Gly
        275                 280                 285
Ile Leu Gly Trp Ser Pro Gln Ala Gln Gly Ile Leu Thr Thr Val Ser
    290                 295                 300
Thr Ile Pro Pro Pro Ala Ser Thr Asn Arg Gln Ser Gly Arg Gln Pro
305                 310                 315                 320
Thr Pro Ile Ser Pro Pro Leu Arg Asp Ser His Pro Gln Ala Met Gln
                325                 330                 335
Trp Asn Ser Thr Ala Phe His Gln Ala Leu Gln Asp Pro Arg Val Arg
            340                 345                 350
Gly Leu Tyr Phe Pro Ala Gly Gly Ser Ser Ser Gly Thr Val Asn Pro
        355                 360                 365
Ala Pro Asn Ile Ala Ser His Ile Ser Ser Ile Ser Ala Arg Thr Gly
    370                 375                 380
Asp Pro Val Thr Asn Asp Tyr Gln Asn Glu Phe Asp Phe Leu Leu Met
385                 390                 395                 400
Glu Arg Ile His Glu Gln Ile Lys Lys Gly Glu Leu Ala Leu Phe Tyr
                405                 410                 415
Leu Gln Asp Tyr Gln Asn Glu Phe Asp Phe Leu Leu Met Glu Arg Ile
            420                 425                 430
His Glu Gln Ile Lys Lys Gly Glu Leu Ala Leu Phe Tyr Leu Gln Asp
        435                 440                 445
Pro Ile His Tyr Asp Lys Ile Thr Glu Glu Ile Asn Lys Ala Val Asp
    450                 455                 460
Glu Ala Val Ala Ala Ile Glu Lys Ser Glu Thr Phe Asp Asp Pro Ile
465                 470                 475                 480
His Tyr Asp Lys Ile Thr Glu Glu Ile Asn Lys Ala Val Asp Glu Ala
                485                 490                 495
```

Val Ala Ala Ile Glu Lys Ser Glu Thr Phe Asp Glu Gln Tyr Asn Leu
                500                 505                 510

Glu Met Ala Lys Lys Ser Gly Asp Ile Leu Glu Arg Asp Leu Lys Lys
            515                 520                 525

Glu Glu Ala Arg Val Lys Lys Ile Glu Val Glu Gln Tyr Asn Leu Glu
        530                 535                 540

Met Ala Lys Lys Ser Gly Asp Ile Leu Glu Arg Asp Leu Lys Lys Glu
545                 550                 555                 560

Glu Ala Arg Val Lys Lys Ile Glu Val
                565

<210> SEQ ID NO 29
<211> LENGTH: 615
<212> TYPE: PRT
<213> ORGANISM: Artificial Sequence
<220> FEATURE:
<223> OTHER INFORMATION: fusion protein

<400> SEQUENCE: 29

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
            20                  25                  30

Val Ile Leu His Asn Gly Val Val Gln Glu Ser Tyr Tyr Arg Tyr Val
        35                  40                  45

Ala Arg Glu Gln Ser Ser Arg Arg Pro Asn Ala Gln Arg Phe Gly Ile
    50                  55                  60

Ser Asn Val Arg Asn Ser Trp Asp Thr Asn Trp Gly Asp Asn Gly Tyr
65                  70                  75                  80

Gly Tyr Phe Ala Ala Asn Ile Asp Leu Met Met Ile Glu Glu Tyr Pro
                85                  90                  95

Tyr Val Val Ile Leu His Asn Gly Val Val Gln Glu Ser Tyr Tyr Arg
            100                 105                 110

Tyr Val Ala Arg Glu Gln Ser Ser Arg Arg Pro Asn Ala Gln Arg Phe
        115                 120                 125

Gly Ile Ser Asn His Gly Ser Glu Pro Ser Ile Ile His Arg Gly Lys
    130                 135                 140

Pro Phe Gln Leu Glu Ala Val Phe Glu Ala Asn Gln Asn Ser Lys Thr
145                 150                 155                 160

Ala Lys His Gly Ser Glu Pro Ser Ile Ile His Arg Gly Lys Pro Phe
                165                 170                 175

Gln Leu Glu Ala Val Phe Glu Ala Asn Gln Asn Ser Lys Thr Ala Lys
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
    210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Pro Ala Ser Thr
        275                 280                 285

Asn Arg Gln Ser Gly Arg Gln Pro Thr Pro Ile Ser Pro Pro Leu Arg
    290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Glu Val Asp
        355                 360                 365

Val Pro Gly Ile Asp Pro Asn Ala Ser His Tyr Met Lys Ser Pro Leu
370                 375                 380

Val Lys Gly Gln Gln Tyr Asp Ile Lys Tyr Thr Trp Ile Val Pro Lys
385                 390                 395                 400

Ile Ala Pro Lys Ser Glu Asn Glu Val Asp Val Pro Gly Ile Asp Pro
                405                 410                 415

Asn Ala Ser His Tyr Met Lys Ser Pro Leu Val Lys Gly Gln Gln Tyr
            420                 425                 430

Asp Ile Lys Tyr Thr Trp Ile Val Pro Lys Ile Ala Pro Lys Ser Glu
        435                 440                 445

Asn Ala Thr Glu Ser Ala Tyr Leu Ala Tyr Arg Asn Gln Ser Leu Asp
450                 455                 460

Leu Ala Glu Gln Glu Leu Val Asp Ser Ala Ser Gln His Gly Ser His
465                 470                 475                 480

Gly Asp Thr Ile Pro Arg Gly Ile Glu Tyr Ile Gln Thr Asn Ala Ser
                485                 490                 495

Ser Ile Asn Gly Asn Ala Pro Ala Glu Ile Asp Leu Arg Gln Met Arg
            500                 505                 510

Thr Val Thr Pro Ile Arg Met Gln Gly Gly Ser Gly Ser Ser Trp Ala
        515                 520                 525

Phe Ser Gly Val Ala Ala Thr Glu Ser Ala Tyr Leu Ala Tyr Arg Asn
530                 535                 540

Gln Ser Leu Asp Leu Ala Glu Gln Glu Leu Val Asp Ser Ala Ser Gln
545                 550                 555                 560

His Gly Ser His Gly Asp Thr Ile Pro Arg Gly Ile Glu Tyr Ile Gln
                565                 570                 575

Thr Asn Ala Ser Ser Ile Asn Gly Asn Ala Pro Ala Glu Ile Asp Leu
            580                 585                 590

Arg Gln Met Arg Thr Val Thr Pro Ile Arg Met Gln Gly Gly Ser Gly
        595                 600                 605

Ser Ser Trp Ala Phe Ser Gly
    610                 615

<210> SEQ ID NO 30
<211> LENGTH: 615
<212> TYPE: PRT
<213> ORGANISM: Artificial Sequence
<220> FEATURE:
<223> OTHER INFORMATION: fusion protein

<400> SEQUENCE: 30

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
            20                  25                  30

```
Val Ile Leu His Asn Gly Val Gln Glu Ser Tyr Tyr Arg Tyr Val
             35                  40                  45

Ala Arg Glu Gln Ser Ser Arg Pro Asn Ala Gln Arg Phe Gly Ile
 50                  55                  60

Ser Asn Val Arg Asn Ser Trp Asp Thr Asn Trp Gly Asp Asn Gly Tyr
 65                  70                  75                  80

Gly Tyr Phe Ala Ala Asn Ile Asp Leu Met Met Ile Glu Glu Tyr Pro
                 85                  90                  95

Tyr Val Val Ile Leu His Asn Gly Val Val Gln Glu Ser Tyr Tyr Arg
                100                 105                 110

Tyr Val Ala Arg Glu Gln Ser Ser Arg Arg Pro Asn Ala Gln Arg Phe
            115                 120                 125

Gly Ile Ser Asn His Gly Ser Glu Pro Ser Ile Ile His Arg Gly Lys
            130                 135                 140

Pro Phe Gln Leu Glu Ala Val Phe Glu Ala Asn Gln Asn Ser Lys Thr
145                 150                 155                 160

Ala Lys His Gly Ser Glu Pro Ser Ile Ile His Arg Gly Lys Pro Phe
                165                 170                 175

Gln Leu Glu Ala Val Phe Glu Ala Asn Gln Asn Ser Lys Thr Ala Lys
            180                 185                 190

Gly Gly Trp Ser Ser Lys Pro Arg Lys Gly Met Gly Thr Asn Leu Ser
            195                 200                 205

Val Pro Asn Pro Leu Gly Phe Phe Asp His Gln Leu Asp Pro Ala
210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Ala Ser Thr
            275                 280                 285

Asn Arg Gln Ser Gly Arg Gln Pro Thr Pro Ile Ser Pro Pro Leu Arg
290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Ala Thr Glu
            355                 360                 365

Ser Ala Tyr Leu Ala Tyr Arg Asn Gln Ser Leu Asp Leu Ala Glu Gln
            370                 375                 380

Glu Leu Val Asp Ser Ala Ser Gln His Gly Ser His Gly Asp Thr Ile
385                 390                 395                 400

Pro Arg Gly Ile Glu Tyr Ile Gln Thr Asn Ala Ser Ser Ile Asn Gly
                405                 410                 415

Asn Ala Pro Ala Glu Ile Asp Leu Arg Gln Met Arg Thr Val Thr Pro
                420                 425                 430

Ile Arg Met Gln Gly Gly Ser Gly Ser Ser Trp Ala Phe Ser Gly Val
            435                 440                 445

Ala Glu Val Asp Val Pro Gly Ile Asp Pro Asn Ala Ser His Tyr Met
```

```
            450                 455                 460
Lys Ser Pro Leu Val Lys Gly Gln Gln Tyr Asp Ile Lys Tyr Thr Trp
465                 470                 475                 480

Ile Val Pro Lys Ile Ala Pro Lys Ser Glu Asn Glu Val Asp Val Pro
                485                 490                 495

Gly Ile Asp Pro Asn Ala Ser His Tyr Met Lys Ser Pro Leu Val Lys
            500                 505                 510

Gly Gln Gln Tyr Asp Ile Lys Tyr Thr Trp Ile Val Pro Lys Ile Ala
                515                 520                 525

Pro Lys Ser Glu Asn Ala Thr Glu Ser Ala Tyr Leu Ala Tyr Arg Asn
            530                 535                 540

Gln Ser Leu Asp Leu Ala Glu Gln Glu Leu Val Asp Ser Ala Ser Gln
545                 550                 555                 560

His Gly Ser His Gly Asp Thr Ile Pro Arg Gly Ile Glu Tyr Ile Gln
                565                 570                 575

Thr Asn Ala Ser Ser Ile Asn Gly Asn Ala Pro Ala Glu Ile Asp Leu
            580                 585                 590

Arg Gln Met Arg Thr Val Thr Pro Ile Arg Met Gln Gly Gly Ser Gly
                595                 600                 605

Ser Ser Trp Ala Phe Ser Gly
            610                 615
```

<210> SEQ ID NO 31
<211> LENGTH: 568
<212> TYPE: PRT
<213> ORGANISM: Artificial Sequence
<220> FEATURE:
<223> OTHER INFORMATION: fusion protein

<400> SEQUENCE: 31

```
Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr Tyr Asn Tyr Glu Phe Ala Leu Glu Ser Ile Lys Leu Leu Ile Lys
                35                  40                  45

Lys Leu Asp Glu Leu Ala Lys Lys Val Lys Ala Val Asn Pro Asp Glu
        50                  55                  60

Tyr Tyr Tyr Asn Tyr Glu Phe Ala Leu Glu Ser Ile Lys Leu Leu Ile
65                  70                  75                  80

Lys Lys Leu Asp Glu Leu Ala Lys Lys Val Lys Ala Val Asn Pro Asp
                85                  90                  95

Glu Tyr Tyr Gly Tyr Phe Ala Asp Pro Lys Asp Pro His Lys Phe Tyr
            100                 105                 110

Ile Cys Ser Asn Trp Glu Ala Val His Lys Asp Cys Pro Gly Asn Thr
        115                 120                 125

Gly Tyr Phe Ala Asp Pro Lys Asp Pro His Lys Phe Tyr Ile Cys Ser
    130                 135                 140

Asn Trp Glu Ala Val His Lys Asp Cys Pro Gly Asn Thr Gly Gly Trp
145                 150                 155                 160

Ser Ser Lys Pro Arg Lys Gly Met Gly Thr Asn Leu Ser Val Pro Asn
                165                 170                 175

Pro Leu Gly Phe Phe Pro Asp His Gln Leu Asp Pro Ala Phe Gly Ala
            180                 185                 190

Asn Ser Asn Asn Pro Asp Trp Asp Phe Asn Pro Ile Lys Asp His Trp
```

```
                    195                 200                 205
Pro Ala Asn Gln Val Gly Val Gly Ala Phe Gly Pro Gly Leu Thr
    210                 215                 220
Pro Pro His Gly Gly Ile Leu Gly Trp Ser Pro Gln Ala Gln Gly Ile
225                 230                 235                 240
Leu Thr Thr Val Ser Thr Ile Pro Pro Ala Ser Thr Asn Arg Gln
            245                 250                 255
Ser Gly Arg Gln Pro Thr Pro Ile Ser Pro Leu Arg Asp Ser His
        260                 265                 270
Pro Gln Ala Met Gln Trp Asn Ser Thr Ala Phe His Gln Ala Leu Gln
    275                 280                 285
Asp Pro Arg Val Arg Gly Leu Tyr Phe Pro Ala Gly Gly Ser Ser Ser
        290                 295                 300
Gly Thr Val Asn Pro Ala Pro Asn Ile Ala Ser His Ile Ser Ser Ile
305                 310                 315                 320
Ser Ala Arg Thr Gly Asp Pro Val Thr Asn Lys Phe Tyr Ile Cys Ser
                325                 330                 335
Asn Trp Glu Ala Val His Lys Asp Cys Pro Gly Asn Thr Arg Trp Asn
            340                 345                 350
Glu Asp Glu Glu Thr Cys Thr Lys Phe Tyr Ile Cys Ser Asn Trp Glu
        355                 360                 365
Ala Val His Lys Asp Cys Pro Gly Asn Thr Arg Trp Asn Glu Asp Glu
370                 375                 380
Glu Thr Cys Thr Asp Tyr Gln Asn Glu Phe Asp Phe Leu Leu Met Glu
385                 390                 395                 400
Arg Ile His Glu Gln Ile Lys Lys Gly Glu Leu Ala Leu Phe Tyr Leu
                405                 410                 415
Gln Asp Tyr Gln Asn Glu Phe Asp Phe Leu Leu Met Glu Arg Ile His
            420                 425                 430
Glu Gln Ile Lys Lys Gly Glu Leu Ala Leu Phe Tyr Leu Gln Asp Pro
        435                 440                 445
Ile His Tyr Asp Lys Ile Thr Glu Glu Ile Asn Lys Ala Val Asp Glu
    450                 455                 460
Ala Val Ala Ala Ile Glu Lys Ser Glu Thr Phe Asp Asp Pro Ile His
465                 470                 475                 480
Tyr Asp Lys Ile Thr Glu Glu Ile Asn Lys Ala Val Asp Glu Ala Val
                485                 490                 495
Ala Ala Ile Glu Lys Ser Glu Thr Phe Asp Glu Gln Tyr Asn Leu Glu
            500                 505                 510
Met Ala Lys Lys Ser Gly Asp Ile Leu Glu Arg Asp Leu Lys Lys Glu
        515                 520                 525
Glu Ala Arg Val Lys Lys Ile Glu Val Glu Gln Tyr Asn Leu Glu Met
    530                 535                 540
Ala Lys Lys Ser Gly Asp Ile Leu Glu Arg Asp Leu Lys Lys Glu Glu
545                 550                 555                 560
Ala Arg Val Lys Lys Ile Glu Val
                565
```

<210> SEQ ID NO 32
<211> LENGTH: 545
<212> TYPE: PRT
<213> ORGANISM: Artificial Sequence
<220> FEATURE:
<223> OTHER INFORMATION: fusion protein

<400> SEQUENCE: 32

```
Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr Tyr Asn Tyr Glu Phe Ala Leu Glu Ser Ile Lys Leu Leu Ile Lys
        35                  40                  45

Lys Leu Asp Glu Leu Ala Lys Lys Val Lys Ala Val Asn Pro Asp Glu
    50                  55                  60

Tyr Tyr Tyr Asn Tyr Glu Phe Ala Leu Glu Ser Ile Lys Leu Leu Ile
65                  70                  75                  80

Lys Lys Leu Asp Glu Leu Ala Lys Lys Val Lys Ala Val Asn Pro Asp
                85                  90                  95

Glu Tyr Tyr Tyr Asn Tyr Glu Phe Ala Leu Glu Ser Ile Lys Leu Leu
            100                 105                 110

Ile Lys Lys Leu Asp Glu Leu Ala Lys Lys Val Lys Ala Val Asn Pro
        115                 120                 125

Asp Glu Tyr Tyr Asp Pro Ile His Tyr Asp Lys Ile Thr Glu Glu Ile
    130                 135                 140

Asn Lys Ala Val Asp Glu Ala Val Ala Ile Glu Lys Ser Glu Thr
145                 150                 155                 160

Phe Asp Asp Pro Ile His Tyr Asp Lys Ile Thr Glu Glu Ile Asn Lys
                165                 170                 175

Ala Val Asp Glu Ala Val Ala Ile Glu Lys Ser Glu Thr Phe Asp
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
    210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Pro Ala Ser Thr
        275                 280                 285

Asn Arg Gln Ser Gly Arg Gln Pro Thr Pro Ile Ser Pro Pro Leu Arg
    290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Asp Tyr Gln
        355                 360                 365

Asn Glu Phe Asp Phe Leu Leu Met Glu Arg Ile His Glu Gln Ile Lys
    370                 375                 380

Lys Gly Glu Leu Ala Leu Phe Tyr Leu Gln Asp Tyr Gln Asn Glu Phe
385                 390                 395                 400

Asp Phe Leu Leu Met Glu Arg Ile His Glu Gln Ile Lys Lys Gly Glu
                405                 410                 415
```

```
Leu Ala Leu Phe Tyr Leu Gln Asp Pro Ile His Tyr Asp Lys Ile Thr
            420                 425                 430

Glu Glu Ile Asn Lys Ala Val Asp Glu Ala Val Ala Ile Glu Lys
            435                 440                 445

Ser Glu Thr Phe Asp Asp Pro Ile His Tyr Asp Lys Ile Thr Glu Glu
        450                 455                 460

Ile Asn Lys Ala Val Asp Glu Ala Val Ala Ile Glu Lys Ser Glu
465                 470                 475                 480

Thr Phe Asp Glu Gln Tyr Asn Leu Glu Met Ala Lys Lys Ser Gly Asp
                485                 490                 495

Ile Leu Glu Arg Asp Leu Lys Lys Glu Ala Arg Val Lys Lys Ile
            500                 505                 510

Glu Val Glu Gln Tyr Asn Leu Glu Met Ala Lys Lys Ser Gly Asp Ile
                515                 520                 525

Leu Glu Arg Asp Leu Lys Lys Glu Ala Arg Val Lys Lys Ile Glu
            530                 535                 540

Val
545

<210> SEQ ID NO 33
<211> LENGTH: 545
<212> TYPE: PRT
<213> ORGANISM: Artificial Sequence
<220> FEATURE:
<223> OTHER INFORMATION: fusion protein

<400> SEQUENCE: 33

Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr Tyr Asn Tyr Glu Phe Ala Leu Glu Ser Ile Lys Leu Leu Ile Lys
        35                  40                  45

Lys Leu Asp Glu Leu Ala Lys Lys Val Lys Ala Val Asn Pro Asp Glu
50                  55                  60

Tyr Tyr Tyr Asn Tyr Glu Phe Ala Leu Glu Ser Ile Lys Leu Leu Ile
65                  70                  75                  80

Lys Lys Leu Asp Glu Leu Ala Lys Lys Val Lys Ala Val Asn Pro Asp
                85                  90                  95

Glu Tyr Tyr Tyr Asn Tyr Glu Phe Ala Leu Glu Ser Ile Lys Leu Leu
            100                 105                 110

Ile Lys Lys Leu Asp Glu Leu Ala Lys Lys Val Lys Ala Val Asn Pro
        115                 120                 125

Asp Glu Tyr Tyr Asp Tyr Gln Asn Glu Phe Asp Phe Leu Leu Met Glu
130                 135                 140

Arg Ile His Glu Gln Ile Lys Lys Gly Glu Leu Ala Leu Phe Tyr Leu
145                 150                 155                 160

Gln Asp Tyr Gln Asn Glu Phe Asp Phe Leu Leu Met Glu Arg Ile His
                165                 170                 175

Glu Gln Ile Lys Lys Gly Glu Leu Ala Leu Phe Tyr Leu Gln Gly Gly
            180                 185                 190

Trp Ser Ser Lys Pro Arg Lys Gly Met Gly Thr Asn Leu Ser Val Pro
        195                 200                 205

Asn Pro Leu Gly Phe Phe Pro Asp His Gln Leu Asp Pro Ala Phe Gly
210                 215                 220
```

```
Ala Asn Ser Asn Asn Pro Asp Trp Asp Phe Asn Pro Ile Lys Asp His
225                 230                 235                 240

Trp Pro Ala Ala Asn Gln Val Gly Val Gly Ala Phe Gly Pro Gly Leu
            245                 250                 255

Thr Pro Pro His Gly Gly Ile Leu Gly Trp Ser Pro Gln Ala Gln Gly
        260                 265                 270

Ile Leu Thr Thr Val Ser Thr Ile Pro Pro Ala Ser Thr Asn Arg
    275                 280                 285

Gln Ser Gly Arg Gln Pro Thr Pro Ile Ser Pro Pro Leu Arg Asp Ser
    290                 295                 300

His Pro Gln Ala Met Gln Trp Asn Ser Thr Ala Phe His Gln Ala Leu
305                 310                 315                 320

Gln Asp Pro Arg Val Arg Gly Leu Tyr Phe Pro Ala Gly Gly Ser Ser
            325                 330                 335

Ser Gly Thr Val Asn Pro Ala Pro Asn Ile Ala Ser His Ile Ser Ser
        340                 345                 350

Ile Ser Ala Arg Thr Gly Asp Pro Val Thr Asn Asp Pro Ile His Tyr
    355                 360                 365

Asp Lys Ile Thr Glu Glu Ile Asn Lys Ala Val Asp Glu Ala Val Ala
370                 375                 380

Ala Ile Glu Lys Ser Glu Thr Phe Asp Asp Pro Ile His Tyr Asp Lys
385                 390                 395                 400

Ile Thr Glu Glu Ile Asn Lys Ala Val Asp Glu Ala Val Ala Ala Ile
            405                 410                 415

Glu Lys Ser Glu Thr Phe Asp Asp Pro Ile His Tyr Asp Lys Ile Thr
        420                 425                 430

Glu Glu Ile Asn Lys Ala Val Asp Glu Ala Val Ala Ala Ile Glu Lys
    435                 440                 445

Ser Glu Thr Phe Asp Asp Pro Ile His Tyr Asp Lys Ile Thr Glu Glu
    450                 455                 460

Ile Asn Lys Ala Val Asp Glu Ala Val Ala Ala Ile Glu Lys Ser Glu
465                 470                 475                 480

Thr Phe Asp Glu Gln Tyr Asn Leu Glu Met Ala Lys Lys Ser Gly Asp
            485                 490                 495

Ile Leu Glu Arg Asp Leu Lys Lys Glu Glu Ala Arg Val Lys Lys Ile
        500                 505                 510

Glu Val Glu Gln Tyr Asn Leu Glu Met Ala Lys Lys Ser Gly Asp Ile
    515                 520                 525

Leu Glu Arg Asp Leu Lys Lys Glu Glu Ala Arg Val Lys Lys Ile Glu
530                 535                 540

Val
545

<210> SEQ ID NO 34
<211> LENGTH: 222
<212> TYPE: PRT
<213> ORGANISM: Artificial Sequence
<220> FEATURE:
<223> OTHER INFORMATION: fusion protein

<400> SEQUENCE: 34

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30
```

-continued

```
Ser Cys Trp Ala Phe Ser Gly Val Ala Ala Thr Glu Ser Ala Tyr Leu
        35                  40                  45

Ala Tyr Arg Asn Gln Ser Leu Asp Leu Ala Glu Gln Glu Leu Val Asp
 50                  55                  60

Cys Ala Ser Gln His Gly Cys His Gly Asp Thr Ile Pro Arg Gly Ile
 65                  70                  75                  80

Glu Tyr Ile Gln His Asn Gly Val Val Gln Glu Ser Tyr Tyr Arg Tyr
                 85                  90                  95

Val Ala Arg Glu Gln Ser Cys Arg Arg Pro Asn Ala Gln Arg Phe Gly
                100                 105                 110

Ile Ser Asn Tyr Cys Gln Ile Tyr Pro Pro Asn Val Asn Lys Ile Arg
            115                 120                 125

Glu Ala Leu Ala Gln Thr His Ser Ala Ile Ala Val Ile Ile Gly Ile
130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
            195                 200                 205

Asp Leu Met Met Ile Glu Glu Tyr Pro Tyr Val Val Ile Leu
210                 215                 220

<210> SEQ ID NO 35
<211> LENGTH: 131
<212> TYPE: PRT
<213> ORGANISM: Artificial Sequence
<220> FEATURE:
<223> OTHER INFORMATION: fusion protein

<400> SEQUENCE: 35

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Glu Gly Leu Glu Val Asp
 50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Ile Val Pro Lys
                85                  90                  95

Ile Ala Pro Lys Ser Glu Asn Val Val Thr Val Lys Val Met Glu
            100                 105                 110

Thr Gly Asp Asn Gly Val Leu Ala Cys Ala Ile Ala Thr His Ala Lys
        115                 120                 125

Ile Arg Asp
    130

<210> SEQ ID NO 36
<211> LENGTH: 617
<212> TYPE: PRT
<213> ORGANISM: Artificial Sequence
```

```
<220> FEATURE:
<223> OTHER INFORMATION: fusion protein

<400> SEQUENCE: 36

Val Arg Asn Ser Trp Asp Thr Thr Trp Gly Asp Ser Gly Tyr Gly Tyr
1               5                   10                  15

Phe Gln Ala Gly Asn Asn Leu Met Met Ile Glu Gln Tyr Pro Tyr Val
            20                  25                  30

Val Ile Met Gln Asn Gly Val Val Glu Glu Arg Ser Tyr Pro Tyr Val
        35                  40                  45

Ala Arg Glu Gln Gln Ser Arg Arg Pro Asn Ser Gln His Tyr Gly Ile
    50                  55                  60

Ser Asn His Gly Ser Asp Pro Ser Ile Ile His Arg Gly Lys Pro Phe
65                  70                  75                  80

Asn Leu Glu Ala Ile Phe Asp Ala Asn Gln Asn Thr Lys Thr Ala Lys
                85                  90                  95

His Gly Ser Asp Pro Ser Ile Ile His Arg Gly Lys Pro Phe Asn Leu
            100                 105                 110

Glu Ala Ile Phe Asp Ala Asn Gln Asn Thr Lys Thr Ala Lys Val Arg
        115                 120                 125

Asn Ser Trp Asp Thr Thr Trp Gly Asp Ser Gly Tyr Gly Tyr Phe Gln
    130                 135                 140

Ala Gly Asn Asn Leu Met Met Ile Glu Gln Tyr Pro Tyr Val Val Ile
145                 150                 155                 160

Met Gln Asn Gly Val Val Glu Glu Arg Ser Tyr Pro Tyr Val Ala Arg
                165                 170                 175

Glu Gln Gln Ser Arg Arg Pro Asn Ser Gln His Tyr Gly Ile Ser Asn
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
    210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Pro Ala Ser Thr
        275                 280                 285

Asn Arg Gln Ser Gly Arg Gln Pro Thr Pro Ile Ser Pro Pro Leu Arg
    290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Glu Val Asp
        355                 360                 365

Val Pro Gly Ile Asp Thr Asn Ala Ser His Tyr Ile Lys Ser Pro Leu
    370                 375                 380

Val Lys Gly Gln Gln Tyr Asp Ala Lys Tyr Thr Trp Asn Val Pro Lys
385                 390                 395                 400
```

Ile Ala Pro Lys Ser Glu Asn Glu Val Asp Val Pro Gly Ile Asp Thr
                405                 410                 415

Asn Ala Ser His Tyr Ile Lys Ser Pro Leu Val Lys Gly Gln Gln Tyr
            420                 425                 430

Asp Ala Lys Tyr Thr Trp Asn Val Pro Lys Ile Ala Pro Lys Ser Glu
        435                 440                 445

Asn Ala Thr Glu Ser Ala Tyr Leu Ala Tyr Arg Asn Thr Ser Leu Asp
450                 455                 460

Leu Ser Glu Gln Glu Leu Val Asp Ser Ala Ser Gln His Gly Ser His
465                 470                 475                 480

Gly Asp Thr Ile Pro Arg Gly Ile Glu Tyr Ile Gln Ser Ala Ser
                485                 490                 495

Arg Ile Asn Ser Val Asn Val Pro Ser Glu Leu Asp Leu Arg Ser Leu
                500                 505                 510

Arg Thr Val Thr Pro Ile Arg Met Gln Gly Gly Ser Gly Ser Ser Trp
                515                 520                 525

Ala Phe Ser Gly Val Ala Ala Thr Glu Ser Ala Tyr Leu Ala Tyr Arg
        530                 535                 540

Asn Thr Ser Leu Asp Leu Ser Glu Gln Glu Leu Val Asp Ser Ala Ser
545                 550                 555                 560

Gln His Gly Ser His Gly Asp Thr Ile Pro Arg Gly Ile Glu Tyr Ile
                565                 570                 575

Gln Thr Ser Ala Ser Arg Ile Asn Ser Val Asn Val Pro Ser Glu Leu
                580                 585                 590

Asp Leu Arg Ser Leu Arg Thr Val Thr Pro Ile Arg Met Gln Gly Gly
                595                 600                 605

Ser Gly Ser Ser Trp Ala Phe Ser Gly
        610                 615

<210> SEQ ID NO 37
<211> LENGTH: 563
<212> TYPE: PRT
<213> ORGANISM: Artificial Sequence
<220> FEATURE:
<223> OTHER INFORMATION: fusion protein

<400> SEQUENCE: 37

Tyr Asn Phe Glu Thr Ala Val Ser Thr Ile Glu Ile Leu Val Lys Asp
1               5                   10                  15

Leu Ala Glu Leu Ala Lys Lys Val Lys Ala Val Lys Ser Asp Asp Tyr
            20                  25                  30

Asn Phe Glu Thr Ala Val Ser Thr Ile Glu Ile Leu Val Lys Asp Leu
        35                  40                  45

Ala Glu Leu Ala Lys Lys Val Lys Ala Val Lys Ser Asp Asp Tyr Asn
50                  55                  60

Phe Glu Thr Ala Val Ser Thr Ile Glu Ile Leu Val Lys Asp Leu Ala
65                  70                  75                  80

Glu Leu Ala Lys Lys Val Lys Ala Val Lys Ser Asp Asp Gly Tyr Phe
                85                  90                  95

Ala Asp Pro Lys Asp Pro Ser Lys Phe Tyr Ile Ser Ser Asn Trp Glu
            100                 105                 110

Ala Ile His Lys Ser Ser Pro Gly Asn Thr Arg Trp Asn Glu Lys Glu
        115                 120                 125

Leu Thr Ser Thr Gly Tyr Phe Ala Asp Pro Lys Asp Pro Ser Lys Phe
130                 135                 140

```
Tyr Ile Ser Ser Asn Trp Glu Ala Ile His Lys Ser Pro Gly Asn
145                 150                 155                 160

Thr Arg Trp Asn Glu Lys Glu Leu Thr Ser Thr Gly Tyr Phe Ala Asp
            165                 170                 175

Pro Lys Asp Pro Ser Lys Phe Tyr Ile Ser Ser Asn Trp Glu Ala Ile
            180                 185                 190

His Lys Ser Ser Pro Gly Asn Thr Arg Trp Asn Glu Lys Glu Leu Thr
            195                 200                 205

Ser Thr Gly Gly Trp Ser Ser Lys Pro Arg Lys Gly Met Gly Thr Asn
        210                 215                 220

Leu Ser Val Pro Asn Pro Leu Gly Phe Phe Pro Asp His Gln Leu Asp
225                 230                 235                 240

Pro Ala Phe Gly Ala Asn Ser Asn Asn Pro Asp Trp Asp Phe Asn Pro
                245                 250                 255

Ile Lys Asp His Trp Pro Ala Ala Asn Gln Val Gly Val Gly Ala Phe
                260                 265                 270

Gly Pro Gly Leu Thr Pro Pro His Gly Gly Ile Leu Gly Trp Ser Pro
            275                 280                 285

Gln Ala Gln Gly Ile Leu Thr Thr Val Ser Thr Ile Pro Pro Pro Ala
290                 295                 300

Ser Thr Asn Arg Gln Ser Gly Arg Gln Pro Thr Pro Ile Ser Pro Pro
305                 310                 315                 320

Leu Arg Asp Ser His Pro Gln Ala Met Gln Trp Asn Ser Thr Ala Phe
                325                 330                 335

His Gln Ala Leu Gln Asp Pro Arg Val Arg Gly Leu Tyr Phe Pro Ala
                340                 345                 350

Gly Gly Ser Ser Ser Gly Thr Val Asn Pro Ala Pro Asn Ile Ala Ser
            355                 360                 365

His Ile Ser Ser Ile Ser Ala Arg Thr Gly Asp Pro Val Thr Asn Asp
        370                 375                 380

Tyr Gln Asn Glu Phe Asp Phe Leu Leu Met Gln Arg Ile His Glu Gln
385                 390                 395                 400

Met Arg Lys Gly Glu Glu Ala Leu Leu His Leu Gln Asp Tyr Gln Asn
                405                 410                 415

Glu Phe Asp Phe Leu Leu Met Gln Arg Ile His Glu Gln Met Arg Lys
                420                 425                 430

Gly Glu Glu Ala Leu Leu His Leu Gln Asp Pro Ile His Tyr Asp Lys
            435                 440                 445

Ile Thr Glu Glu Ile Asn Lys Ala Ile Asp Asp Ala Ile Ala Ala Ile
        450                 455                 460

Glu Gln Ser Glu Thr Ile Asp Asp Pro Ile His Tyr Asp Lys Ile Thr
465                 470                 475                 480

Glu Glu Ile Asn Lys Ala Ile Asp Asp Ala Ile Ala Ala Ile Glu Gln
                485                 490                 495

Ser Glu Thr Ile Asp Glu Arg Tyr Asn Val Glu Ile Ala Leu Lys Ser
            500                 505                 510

Asn Glu Ile Leu Glu Arg Asp Leu Lys Lys Glu Glu Gln Arg Val Lys
            515                 520                 525

Lys Ile Glu Val Glu Arg Tyr Asn Val Glu Ile Ala Leu Lys Ser Asn
        530                 535                 540

Glu Ile Leu Glu Arg Asp Leu Lys Lys Glu Glu Gln Arg Val Lys Lys
545                 550                 555                 560
```

Ile Glu Val

<210> SEQ ID NO 38
<211> LENGTH: 42
<212> TYPE: PRT
<213> ORGANISM: Artificial Sequence
<220> FEATURE:
<223> OTHER INFORMATION: allergen fragment

<400> SEQUENCE: 38

Thr Ser Ala Cys Arg Ile Asn Ser Val Asn Val Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala
        35                  40

<210> SEQ ID NO 39
<211> LENGTH: 43
<212> TYPE: PRT
<213> ORGANISM: Artificial Sequence
<220> FEATURE:
<223> OTHER INFORMATION: allergen fragment

<400> SEQUENCE: 39

Ala Thr Glu Ser Ala Tyr Leu Ala Tyr Arg Asn Thr Ser Leu Asp Leu
1               5                   10                  15

Ser Glu Gln Glu Leu Val Asp Cys Ala Ser Gln His Gly Cys His Gly
            20                  25                  30

Asp Thr Ile Pro Arg Gly Ile Glu Tyr Ile Gln
        35                  40

<210> SEQ ID NO 40
<211> LENGTH: 31
<212> TYPE: PRT
<213> ORGANISM: Artificial Sequence
<220> FEATURE:
<223> OTHER INFORMATION: allergen fragment

<400> SEQUENCE: 40

Gln Asn Gly Val Val Glu Glu Arg Ser Tyr Pro Tyr Val Ala Arg Glu
1               5                   10                  15

Gln Gln Cys Arg Arg Pro Asn Ser Gln His Tyr Gly Ile Ser Asn
            20                  25                  30

<210> SEQ ID NO 41
<211> LENGTH: 35
<212> TYPE: PRT
<213> ORGANISM: Artificial Sequence
<220> FEATURE:
<223> OTHER INFORMATION: allergen fragment

<400> SEQUENCE: 41

Val Arg Asn Ser Trp Asp Thr Thr Trp Gly Asp Ser Gly Tyr Gly Tyr
1               5                   10                  15

Phe Gln Ala Gly Asn Asn Leu Met Met Ile Glu Gln Tyr Pro Tyr Val
            20                  25                  30

Val Ile Met
        35

<210> SEQ ID NO 42
<211> LENGTH: 30
<212> TYPE: PRT

```
<213> ORGANISM: Artificial Sequence
<220> FEATURE:
<223> OTHER INFORMATION: allergen fragment

<400> SEQUENCE: 42

His Gly Ser Asp Pro Cys Ile Ile His Arg Gly Lys Pro Phe Asn Leu
1               5                   10                  15

Glu Ala Ile Phe Asp Ala Asn Gln Asn Thr Lys Thr Ala Lys
            20                  25                  30

<210> SEQ ID NO 43
<211> LENGTH: 42
<212> TYPE: PRT
<213> ORGANISM: Artificial Sequence
<220> FEATURE:
<223> OTHER INFORMATION: allergen fragment

<400> SEQUENCE: 43

Glu Val Asp Val Pro Gly Ile Asp Thr Asn Ala Cys His Tyr Ile Lys
1               5                   10                  15

Cys Pro Leu Val Lys Gly Gln Gln Tyr Asp Ala Lys Tyr Thr Trp Asn
            20                  25                  30

Val Pro Lys Ile Ala Pro Lys Ser Glu Asn
        35                  40

<210> SEQ ID NO 44
<211> LENGTH: 29
<212> TYPE: PRT
<213> ORGANISM: Artificial Sequence
<220> FEATURE:
<223> OTHER INFORMATION: allergen fragment

<400> SEQUENCE: 44

Asp Tyr Gln Asn Glu Phe Asp Phe Leu Leu Met Gln Arg Ile His Glu
1               5                   10                  15

Gln Met Arg Lys Gly Glu Glu Ala Leu Leu His Leu Gln
            20                  25

<210> SEQ ID NO 45
<211> LENGTH: 31
<212> TYPE: PRT
<213> ORGANISM: Artificial Sequence
<220> FEATURE:
<223> OTHER INFORMATION: allergen fragment

<400> SEQUENCE: 45

Glu Arg Tyr Asn Val Glu Ile Ala Leu Lys Ser Asn Glu Ile Leu Glu
1               5                   10                  15

Arg Asp Leu Lys Lys Glu Glu Gln Arg Val Lys Lys Ile Glu Val
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: allergen fragment

<400> SEQUENCE: 46

Asp Pro Ile His Tyr Asp Lys Ile Thr Glu Glu Ile Asn Lys Ala Ile
1               5                   10                  15

Asp Asp Ala Ile Ala Ala Ile Glu Gln Ser Glu Thr Ile Asp
            20                  25                  30
```

<210> SEQ ID NO 47
<211> LENGTH: 31
<212> TYPE: PRT
<213> ORGANISM: Artificial Sequence
<220> FEATURE:
<223> OTHER INFORMATION: allergen fragment

<400> SEQUENCE: 47

Tyr Asn Phe Glu Thr Ala Val Ser Thr Ile Glu Ile Leu Val Lys Asp
1               5                   10                  15

Leu Ala Glu Leu Ala Lys Lys Val Lys Ala Val Lys Ser Asp Asp
            20                  25                  30

<210> SEQ ID NO 48
<211> LENGTH: 39
<212> TYPE: PRT
<213> ORGANISM: Artificial Sequence
<220> FEATURE:
<223> OTHER INFORMATION: allergen fragment

<400> SEQUENCE: 48

Gly Tyr Phe Ala Asp Pro Lys Asp Pro Cys Lys Phe Tyr Ile Cys Ser
1               5                   10                  15

Asn Trp Glu Ala Ile His Lys Ser Cys Pro Gly Asn Thr Arg Trp Asn
            20                  25                  30

Glu Lys Glu Leu Thr Cys Thr
        35

<210> SEQ ID NO 49
<211> LENGTH: 37
<212> TYPE: PRT
<213> ORGANISM: Artificial Sequence
<220> FEATURE:
<223> OTHER INFORMATION: allergen fragment

<400> SEQUENCE: 49

Arg Glu Gln Ser Cys Arg Arg Pro Asn Ala Gln Arg Phe Gly Ile Ser
1               5                   10                  15

Asn Tyr Cys Gln Ile Tyr Pro Pro Asn Val Asn Lys Ile Arg Glu Ala
            20                  25                  30

Leu Ala Gln Thr His
        35

<210> SEQ ID NO 50
<211> LENGTH: 31
<212> TYPE: PRT
<213> ORGANISM: Artificial Sequence
<220> FEATURE:
<223> OTHER INFORMATION: allergen fragment

<400> SEQUENCE: 50

Lys Asp Leu Asp Ala Phe Arg His Tyr Asp Gly Arg Thr Ile Ile Gln
1               5                   10                  15

Arg Asp Asn Gly Tyr Gln Pro Asn Tyr His Ala Val Asn Ile Val
            20                  25                  30

<210> SEQ ID NO 51
<211> LENGTH: 33
<212> TYPE: PRT
<213> ORGANISM: Artificial Sequence
<220> FEATURE:
<223> OTHER INFORMATION: allergen fragment

<400> SEQUENCE: 51

```
Gly Arg Thr Ile Ile Gln Arg Asp Asn Gly Tyr Gln Pro Asn Tyr His
1               5                   10                  15

Ala Val Asn Ile Val Gly Tyr Ser Asn Ala Gln Gly Val Asp Tyr Trp
            20                  25                  30

Ile
```

<210> SEQ ID NO 52
<211> LENGTH: 34
<212> TYPE: PRT
<213> ORGANISM: Artificial Sequence
<220> FEATURE:
<223> OTHER INFORMATION: allergen fragment

<400> SEQUENCE: 52

```
Val Gly Tyr Ser Asn Ala Gln Gly Val Asp Tyr Trp Ile Val Arg Asn
1               5                   10                  15

Ser Trp Asp Thr Asn Trp Gly Asp Asn Gly Tyr Gly Tyr Phe Ala Ala
            20                  25                  30

Asn Ile
```

<210> SEQ ID NO 53
<211> LENGTH: 33
<212> TYPE: PRT
<213> ORGANISM: Artificial Sequence
<220> FEATURE:
<223> OTHER INFORMATION: allergen fragment

<400> SEQUENCE: 53

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys
```

<210> SEQ ID NO 54
<211> LENGTH: 32
<212> TYPE: PRT
<213> ORGANISM: Artificial Sequence
<220> FEATURE:
<223> OTHER INFORMATION: allergen fragment

<400> SEQUENCE: 54

```
Glu Ala Asn Gln Asn Ser Lys Thr Ala Lys Ile Glu Ile Lys Ala Ser
1               5                   10                  15

Ile Glu Gly Leu Glu Val Asp Val Pro Gly Ile Asp Pro Asn Ala Cys
            20                  25                  30
```

<210> SEQ ID NO 55
<211> LENGTH: 32
<212> TYPE: PRT
<213> ORGANISM: Artificial Sequence
<220> FEATURE:
<223> OTHER INFORMATION: allergen fragment

<400> SEQUENCE: 55

```
Ala Pro Lys Ser Glu Asn Val Val Val Thr Val Lys Val Met Gly Asp
1               5                   10                  15

Asn Gly Val Leu Ala Cys Ala Ile Ala Thr His Ala Lys Ile Arg Asp
            20                  25                  30
```

<210> SEQ ID NO 56

<211> LENGTH: 34
<212> TYPE: PRT
<213> ORGANISM: Artificial Sequence
<220> FEATURE:
<223> OTHER INFORMATION: allergen fragment

<400> SEQUENCE: 56

Glu Asp Lys Lys His Asp Tyr Gln Asn Glu Phe Asp Phe Leu Leu Met
1               5                   10                  15

Glu Arg Ile His Glu Gln Ile Lys Lys Gly Glu Leu Ala Leu Phe Tyr
            20                  25                  30

Leu Gln

<210> SEQ ID NO 57
<211> LENGTH: 36
<212> TYPE: PRT
<213> ORGANISM: Artificial Sequence
<220> FEATURE:
<223> OTHER INFORMATION: allergen fragment

<400> SEQUENCE: 57

Lys Lys Gly Glu Leu Ala Leu Phe Tyr Leu Gln Glu Gln Ile Asn His
1               5                   10                  15

Phe Glu Glu Lys Pro Thr Lys Glu Met Lys Asp Lys Ile Val Ala Glu
            20                  25                  30

Met Asp Thr Ile
        35

<210> SEQ ID NO 58
<211> LENGTH: 31
<212> TYPE: PRT
<213> ORGANISM: Artificial Sequence
<220> FEATURE:
<223> OTHER INFORMATION: allergen fragment

<400> SEQUENCE: 58

Asp Gly Val Arg Gly Val Leu Asp Arg Leu Met Gln Arg Lys Asp Leu
1               5                   10                  15

Asp Ile Phe Glu Gln Tyr Asn Leu Glu Met Ala Lys Lys Ser Gly
            20                  25                  30

<210> SEQ ID NO 59
<211> LENGTH: 36
<212> TYPE: PRT
<213> ORGANISM: Artificial Sequence
<220> FEATURE:
<223> OTHER INFORMATION: allergen fragment

<400> SEQUENCE: 59

Asp Leu Asp Ile Phe Glu Gln Tyr Asn Leu Glu Met Ala Lys Lys Ser
1               5                   10                  15

Gly Asp Ile Leu Glu Arg Asp Leu Lys Lys Glu Glu Ala Arg Val Lys
            20                  25                  30

Lys Ile Glu Val
        35

<210> SEQ ID NO 60
<211> LENGTH: 29
<212> TYPE: PRT
<213> ORGANISM: Artificial Sequence
<220> FEATURE:
<223> OTHER INFORMATION: allergen fragment

<400> SEQUENCE: 60

```
Glu Asp Lys Lys His Asp Tyr Gln Asn Glu Phe Asp Phe Leu Leu Met
1               5                   10                  15

Glu Arg Ile His Glu Gln Ile Lys Lys Gly Glu Leu Ala
            20                  25

<210> SEQ ID NO 61
<211> LENGTH: 31
<212> TYPE: PRT
<213> ORGANISM: Artificial Sequence
<220> FEATURE:
<223> OTHER INFORMATION: allergen fragment

<400> SEQUENCE: 61

Asp Leu Asp Ile Phe Glu Gln Tyr Asn Leu Glu Met Ala Lys Lys Ser
1               5                   10                  15

Gly Asp Ile Leu Glu Arg Asp Leu Lys Lys Glu Ala Arg Val
            20                  25                  30

<210> SEQ ID NO 62
<211> LENGTH: 34
<212> TYPE: PRT
<213> ORGANISM: Artificial Sequence
<220> FEATURE:
<223> OTHER INFORMATION: allergen fragment

<400> SEQUENCE: 62

Phe Ile Val Gly Asp Lys Lys Glu Asp Glu Trp Arg Met Ala Phe Asp
1               5                   10                  15

Arg Leu Met Met Glu Glu Leu Glu Thr Lys Ile Asp Gln Val Glu Lys
            20                  25                  30

Gly Leu

<210> SEQ ID NO 63
<211> LENGTH: 37
<212> TYPE: PRT
<213> ORGANISM: Artificial Sequence
<220> FEATURE:
<223> OTHER INFORMATION: allergen fragment

<400> SEQUENCE: 63

Leu His Leu Ser Glu Gln Tyr Lys Glu Leu Glu Lys Thr Lys Ser Lys
1               5                   10                  15

Glu Leu Lys Glu Gln Ile Leu Arg Glu Leu Thr Ile Gly Glu Asn Phe
            20                  25                  30

Met Lys Gly Ala Leu
        35

<210> SEQ ID NO 64
<211> LENGTH: 29
<212> TYPE: PRT
<213> ORGANISM: Artificial Sequence
<220> FEATURE:
<223> OTHER INFORMATION: allergen fragment

<400> SEQUENCE: 64

Met Lys Gly Ala Leu Lys Phe Phe Glu Met Glu Ala Lys Arg Thr Asp
1               5                   10                  15

Leu Asn Met Phe Glu Arg Tyr Asn Tyr Glu Phe Ala Leu
            20                  25

<210> SEQ ID NO 65
<211> LENGTH: 31
```

```
<212> TYPE: PRT
<213> ORGANISM: Artificial Sequence
<220> FEATURE:
<223> OTHER INFORMATION: allergen fragment

<400> SEQUENCE: 65

Val Ala Ala Ile Glu Lys Ser Glu Thr Phe Asp Pro Met Lys Val Pro
1               5                   10                  15

Asp His Ser Asp Lys Phe Glu Arg His Ile Gly Ile Ile Asp Leu
                20                  25                  30

<210> SEQ ID NO 66
<211> LENGTH: 31
<212> TYPE: PRT
<213> ORGANISM: Artificial Sequence
<220> FEATURE:
<223> OTHER INFORMATION: allergen fragment

<400> SEQUENCE: 66

Leu Lys Gly Glu Leu Asp Met Arg Asn Ile Gln Val Arg Gly Leu Lys
1               5                   10                  15

Gln Met Lys Arg Val Gly Asp Ala Asn Val Lys Ser Glu Asp Gly
                20                  25                  30

<210> SEQ ID NO 67
<211> LENGTH: 36
<212> TYPE: PRT
<213> ORGANISM: Artificial Sequence
<220> FEATURE:
<223> OTHER INFORMATION: allergen fragment

<400> SEQUENCE: 67

Val His Asp Asp Val Val Ser Met Glu Tyr Asp Leu Ala Tyr Lys Leu
1               5                   10                  15

Gly Asp Leu His Pro Asn Thr His Val Ile Ser Asp Ile Gln Asp Phe
                20                  25                  30

Val Val Glu Leu
        35

<210> SEQ ID NO 68
<211> LENGTH: 26
<212> TYPE: PRT
<213> ORGANISM: Artificial Sequence
<220> FEATURE:
<223> OTHER INFORMATION: allergen fragment

<400> SEQUENCE: 68

Val Glu Leu Ser Leu Glu Val Ser Glu Glu Gly Asn Met Thr Leu Thr
1               5                   10                  15

Ser Phe Glu Val Arg Gln Phe Ala Asn Val
                20                  25

<210> SEQ ID NO 69
<211> LENGTH: 28
<212> TYPE: PRT
<213> ORGANISM: Artificial Sequence
<220> FEATURE:
<223> OTHER INFORMATION: allergen fragment

<400> SEQUENCE: 69

Val Asn His Ile Gly Gly Leu Ser Ile Leu Asp Pro Ile Phe Ala Val
1               5                   10                  15

Leu Ser Asp Val Leu Thr Ala Ile Phe Gln Asp Thr
                20                  25
```

```
<210> SEQ ID NO 70
<211> LENGTH: 29
<212> TYPE: PRT
<213> ORGANISM: Artificial Sequence
<220> FEATURE:
<223> OTHER INFORMATION: allergen fragment

<400> SEQUENCE: 70

Thr Ala Ile Phe Gln Asp Thr Val Arg Ala Glu Met Thr Lys Val Leu
1               5                   10                  15

Ala Pro Ala Phe Lys Lys Glu Leu Glu Arg Asn Asn Gln
            20                  25

<210> SEQ ID NO 71
<211> LENGTH: 32
<212> TYPE: PRT
<213> ORGANISM: Artificial Sequence
<220> FEATURE:
<223> OTHER INFORMATION: allergen fragment

<400> SEQUENCE: 71

Met Ala Asn Asp Asn Asp Asp Pro Thr Thr Thr Val His Pro Thr
1               5                   10                  15

Thr Thr Glu Gln Pro Asp Asp Lys Phe Glu Cys Pro Ser Arg Phe Gly
            20                  25                  30

<210> SEQ ID NO 72
<211> LENGTH: 34
<212> TYPE: PRT
<213> ORGANISM: Artificial Sequence
<220> FEATURE:
<223> OTHER INFORMATION: allergen fragment

<400> SEQUENCE: 72

Pro Thr Thr Thr Glu Gln Pro Asp Asp Lys Phe Glu Cys Pro Ser Arg
1               5                   10                  15

Phe Gly Tyr Phe Ala Asp Pro Lys Asp Pro His Lys Phe Tyr Ile Cys
            20                  25                  30

Ser Asn

<210> SEQ ID NO 73
<211> LENGTH: 39
<212> TYPE: PRT
<213> ORGANISM: Artificial Sequence
<220> FEATURE:
<223> OTHER INFORMATION: allergen fragment

<400> SEQUENCE: 73

Gly Tyr Phe Ala Asp Pro Lys Asp Pro His Lys Phe Ala Ile Cys Ser
1               5                   10                  15

Asn Trp Ala Ala Val His Lys Ala Cys Pro Gly Asn Thr Arg Trp Asn
            20                  25                  30

Ala Ala Ala Ala Thr Cys Thr
        35

<210> SEQ ID NO 74
<211> LENGTH: 39
<212> TYPE: PRT
<213> ORGANISM: Artificial Sequence
<220> FEATURE:
<223> OTHER INFORMATION: allergen fragment

<400> SEQUENCE: 74
```

Gly Tyr Phe Ala Asp Pro Lys Asp Pro His Ala Phe Tyr Ile Cys Ser
1               5                   10                  15

Asn Trp Glu Ala Val Ala Ala Asp Cys Pro Gly Asn Thr Arg Trp Asn
            20                  25                  30

Glu Asp Glu Glu Thr Cys Thr
        35

<210> SEQ ID NO 75
<211> LENGTH: 29
<212> TYPE: PRT
<213> ORGANISM: Artificial Sequence
<220> FEATURE:
<223> OTHER INFORMATION: allergen fragment

<400> SEQUENCE: 75

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr
            20                  25

<210> SEQ ID NO 76
<211> LENGTH: 29
<212> TYPE: PRT
<213> ORGANISM: Artificial Sequence
<220> FEATURE:
<223> OTHER INFORMATION: allergen fragment

<400> SEQUENCE: 76

Gly Tyr Phe Ala Asp Pro Lys Asp Pro His Lys Phe Tyr Ile Ser Ser
1               5                   10                  15

Asn Trp Glu Ala Val His Lys Asp Ser Pro Gly Asn Thr
            20                  25

<210> SEQ ID NO 77
<211> LENGTH: 29
<212> TYPE: PRT
<213> ORGANISM: Artificial Sequence
<220> FEATURE:
<223> OTHER INFORMATION: allergen fragment

<400> SEQUENCE: 77

Lys Phe Tyr Ile Cys Ser Asn Trp Glu Ala Val His Lys Asp Cys Pro
1               5                   10                  15

Gly Asn Thr Arg Trp Asn Glu Asp Glu Glu Thr Cys Thr
            20                  25

<210> SEQ ID NO 78
<211> LENGTH: 29
<212> TYPE: PRT
<213> ORGANISM: Artificial Sequence
<220> FEATURE:
<223> OTHER INFORMATION: allergen fragment

<400> SEQUENCE: 78

Lys Phe Tyr Ile Ser Ser Asn Trp Glu Ala Val His Lys Asp Ser Pro
1               5                   10                  15

Gly Asn Thr Arg Trp Asn Glu Asp Glu Glu Thr Ser Thr
            20                  25

<210> SEQ ID NO 79
<211> LENGTH: 24
<212> TYPE: PRT
<213> ORGANISM: Artificial Sequence

```
<220> FEATURE:
<223> OTHER INFORMATION: allergen fragment

<400> SEQUENCE: 79

Ser Asn Trp Glu Ala Val His Lys Asp Cys Pro Gly Asn Thr Arg Trp
1               5                   10                  15

Asn Glu Asp Glu Glu Thr Cys Thr
            20

<210> SEQ ID NO 80
<211> LENGTH: 33
<212> TYPE: PRT
<213> ORGANISM: Artificial Sequence
<220> FEATURE:
<223> OTHER INFORMATION: allergen fragment

<400> SEQUENCE: 80

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Arg Trp Asn
            20                  25                  30

Glu

<210> SEQ ID NO 81
<211> LENGTH: 37
<212> TYPE: PRT
<213> ORGANISM: Artificial Sequence
<220> FEATURE:
<223> OTHER INFORMATION: allergen fragment

<400> SEQUENCE: 81

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Arg Trp Asn
            20                  25                  30

Glu Asp Glu Glu Thr
            35
```

TREATMENT AND PREVENTION OF HOUSE DUST MITE ALLERGIES

TECHNICAL FIELD

The present invention relates to the field of immunotherapy of patients suffering from an allergy, in particular of house dust mite allergy.

BACKGROUND ART

More than 25% of the population in industrialised countries suffer from IgE-mediated allergies. Allergic patients are characterized by the increased production of IgE antibodies against per se harmless antigens (i.e., allergens). The immediate symptoms of Type I allergy (allergic rhinoconjunctivitis, asthma, dermatitis, anaphylactic shock) are caused by allergen-induced cross-linking of mast cell-bound IgE antibodies and the release of biologically active mediators (e.g., histamine, leukotriens)

WO 2012/168487 describes the use of a surface polypeptide of a virus of the hepadnaviridae family (e.g. Hepatitis B virus) as a carrier protein for allergen fragments.

In Banerjee S et al. (J Immunol 192(2014):4867-4875) proteins comprising two or four identical allergen fragments of Der p 23 fused to the N- and C-terminus of PreS are disclosed. According to Banerjee S et al. the fusion protein comprising two identical Der p 23 fragments on the C-terminus of PreS and other two identical Der p 23 fragments on the N-terminus of PreS induced the formation of Der p 23 specific antibodies showing a significant IgE inhibition compared to fusion proteins comprising the same Der p 23 fragments on both termini of PreS.

Curin M et al. (Allergy 73(2018):1653-1661) discloses fragments of Der p 5 and Der p 21 which can be used for the further development of vaccines.

In EP 2 727 934 allergen fragments of several Der p allergens lacking IgE reactivity and exhibiting T cell reactivity were tested.

Huey-Jy H et al. (J Immunol 196(2016): Suppl 1 192, 5) describes polypeptides comprising inter alia fragments of Der p 1, Der p 2, Der p 7 and Der p 8.

Bussières L et al. (Int Arch Allergy Immunol 153(2010): 141-151) as well as EP 1 908 776 describe fusion proteins comprising mature Der p 1 and Der p 2.

WO 2009/118642 discloses fusion polypeptides which comprise fragments of Der p 1 and Der p 2 having a length of at least 50 amino acid residues.

Chen A et al. (Mol Immunol 45(2008):2486-2498), Casset A et al. (Int Arch Allergy Immunol 159(253-262), WO 2015/070925 and Chen K-W et al. (Allergy 67(2012):609-621) disclose fragments of Der p allergens. Some of these fragments may be bound to carrier proteins.

House-dust mites (HDMs) represent one of the most important allergen sources worldwide. Almost 10% of the population and more than 50% of allergic patients are sensitized to mite allergens. The HDM *Dermatophagoides pteronyssinus* (Der p) and *Dermatophagoides farina* (Der f) are prevalent worldwide. The allergens of Der p and Der f comprise more than 30 proteins or glycoproteins of which most have been characterized so far. Group 1, 2 and 23 allergens (Der p 1, Der p 2 and Der p 23 as well as Der f 1 and Der f 2 and Der f 23) represent very important allergens from HDM, to which more than 80% of HDM allergic patients are sensitized. However, it has been shown recently that other HDM allergens (e.g., Der p 5, Der p 7 and Der p 21 as well as Der f 5, Der f 7 and Der f 21) represent important HDM allergens and cause sensitization and allergic symptoms in 15 to >40% of HDM allergic patients (Posa et al.,J Allergy Clin Immunol. 2017 Feb;139(2):541-549.e8). In this context it was found that current allergen extract-based HDM vaccines fail to induce sufficient protective IgG antibodies against Der p 5, Der p 7, Der p 21 and Der p 23 and leave many HDM allergic patients untreated (Selection of house dust mite-allergic patients by molecular diagnosis may enhance success of specific immunotherapy. Chen K W, Zieglmayer P, Zieglmayer R, Lemell P, Horak F, Bunu CP, Valenta R, Vrtala S. J Allergy Clin Immunol. 2019 Mar;143 (3):1248-1252. e12. doi: 10.1016/j.jaci.2018.10.048. Epub 2018 Nov. 14) Therefore, it was recognized as an important task to discover and develop a vaccine for allergy immunotherapy of house dust mite allergy, which provides complete protection of HDM allergic patients by inducing blocking antibodies against Der p 1, Der p 2, Der p 5, Der p 7, Der p 21 and Der p 23 as well as the corresponding Der f allergens.

SUMMARY OF THE INVENTION

Currently approved immunotherapy products for house dust mite allergies are based on extracts from HDM bodies and fecal particles. These pro-ducts contain variable concentrations of Der p 1, Der p 2, Der f 1 and Der f 2. They do not contain all relevant HDM allergens and especially concentrations of Der p 23 and Der f 23 are very low. Therefore they provide only an incomplete solution for the treatment or prevention of patients with house dust mite allergies (Casset et al., Int Arch Allergy Immunol. 2013; 161(3): 287-288). For instance, sublingual tablets marketed by ALK Abelló achieve only a mean reduction of allergy symptoms by 18% compared to placebo (Demoly et al., J. Allergy Clin. Immunol. 2016; 137: 444-451). Due to the relatively high number of different house dust mite allergens a potential immunotherapy would require the administration of many different proteins and polypeptides in order to cover at least the most important house dust mite allergens.

Hence, it is an object of the present invention to provide a vaccine and respective components comprised therein which can be used in the treatment and/or prevention of house dust mite allergies caused by all six major allergens.

This object is solved by one or more fusion protein(s) having formula (I)

$$X_1-Y-X_2 \qquad (I),$$

wherein $X_1$ and $X_2$ comprise each four to eight allergen fragments or variants thereof fused to each other, wherein said allergen fragments are derived from at least two allergens of the genus *Dermatophagoides*, and wherein Y is a carrier protein.

Another aspect of the present invention relates to a pharmaceutical preparation comprising at least one fusion protein as described above.

A further aspect of the present invention relates to a fusion protein or a pharmaceutical preparation of the present invention for the use in the treatment or the prevention of an allergy caused by an allergen of a house dust mite.

Another aspect of the present invention relates to a nucleic acid molecule encoding a fusion protein according to the present invention.

A further aspect of the present invention relates to a vector comprising a nucleic acid molecule according to the present invention.

Yet another aspect of the present invention relates to a host cell comprising a nucleic acid molecule or a vector according to the present invention.

BRIEF DESCRIPTION OF THE FIGURES

FIG. 6 shows the inhibition of patients' IgE binding to Der p 1 and Der p 2 with anti-sera specific for Der p 1-2 C3.

FIG. 7 shows the inhibition of patients' IgE binding to Der p 5, Der p 7, Der p 21 and Der p 23 with anti-sera specific for Der p 5 7 21 23_P6.

FIGS. 8A to 8F show serum levels of IgGs specifically binding to house dust mite allergens Der p 1 (FIG. 8A), Der p 2 (FIG. 8B), Der p 5 (FIG. 8C), Der p 7 (FIG. 8D), Der p 21 (FIG. 8E) and Der p 23 (FIG. 8F) determined by ELISA from rabbit sera immunized with 20 μg BM35 ("BM35 20"), 40 μg BM35 ("BM35 40"), 80 μg BM35 ("BM35 80"), Tyro-SIT ("Bencard"), Alutard SQ 503 ("ALK D.pter"), Alutard SQ 510 ("ALK Dp/Df"), ACAROID ("Allergoph."), PURETHAL Milbenmischung ("HAL"), CLUSTOID Milben Injektionssuspension ("Roxal") and nDer p1, rDer p 2, rDer p 5, rDer p 7, rDer p 21 and rDer p 23. The samples were retrieved at days 38 and 66 after the first injection.

DESCRIPTION OF EMBODIMENTS

Figure 1:
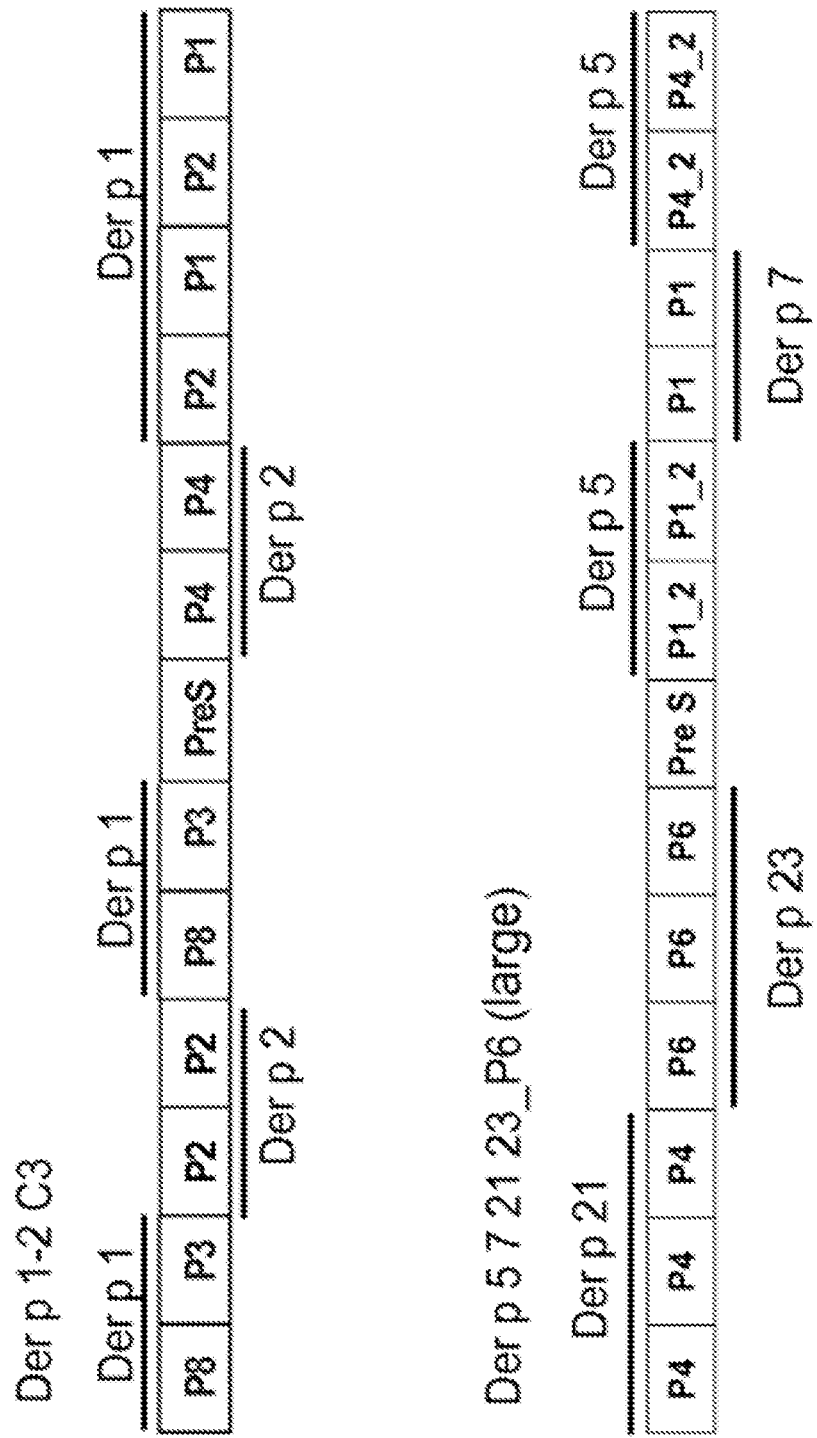
FIG. 1 shows a schematic representation of constructs Der p 1-2 C3 and Der p 5 7 21 23_P6 (large). PreS stands for the surface antigen PreS of the hepatitis B virus. "P" indicates the peptides derived from house dust mite allergen Der p 1, Der p 2, Der p 5, Der p 7, Der p 21 and Der p 23 as mentioned in Table I.

The present invention relates to one or more fusion protein(s) having formula (I)

$$X_1-Y-X_2 \quad (I),$$

wherein $X_1$ and $X_2$ comprise each four to eight allergen fragments or variants thereof fused to each other, wherein said allergen fragments are derived from at least two allergens of the genus *Dermatophagoides*, and wherein Y is a carrier protein.

It turned surprisingly out that a fusion protein having an "architecture" as defined by formula (I) induces the in vivo formation of antibodies directed to the at least two allergens of the genus *Dermatophagoides*. In particular the presence of four to eight allergen fragments at the C- and N-terminus of a carrier protein has advantageous effect in regard to the induction of antibodies inhibiting the interaction of allergen specific IgEs to their respective allergen. The formation of such antibodies allows to reduce or even to prevent allergic reactions resulting in the treatment of allergies caused by allergens of the genus *Dermatophagoides*.

"Fusion protein", as used herein, refers to a protein or polypeptide created by attaching two or more polypeptides and/or peptides to each other. Fusion proteins can be produced by recombinant DNA technology or through chemical covalent conjugation.

"Allergen fragment", as used herein, refers to a peptide or polypeptide stretch derived from an allergen by fragmentation.

The four to eight, preferably the four to six allergen fragments, which are fused to each other, are derived from at least two, preferably at least three, more preferably at least four, in particular from one, two, three or four, allergens of one or more house dust mites of the genus *Dermatophagoides*. These allergen fragments consist of 8 to 100, preferably 8 to 80, more preferably 8 to 60, more preferably 10 to 60, more preferably 10 to 50, more preferably 15 to 50, more preferably 20 to 50, more preferably 25 to 50, consecutive amino acid residues of said allergen.

The fusion protein of the present invention may comprise more than one fragment derived from the same allergen. In such a case the fragments may be derived from different (i.e. non-adjacent) regions or from adjacent regions of the same allergen. In the latter case the order of the fragments may be different than in the allergen from which the fragments are derived from.

The fusion protein of the present invention may also comprise one or more allergen fragments having the same or substantially the same amino acid sequence. "Substantially the same", as used herein, means that two or more sequences derived from the same allergen show at least 80%, preferably at least 85%, more preferably at least 90%, more preferably at least 95%, sequence identity.

The degree of identity of a first amino acid sequence to a second amino acid sequence can be determined by a direct comparison between both amino acid sequences using certain algorithms. Such algorithms are, for instance, incorporated in various computer programs or websites (e.g. https://www.ncbi.nlm.nih.gov/) (e.g. "BLAST 2 SEQUENCES (blastp)" (Tatusova et al. (1999) FEMS Microbiol. Lett. 174:247-25; Corpet F, Nucl. Acids Res. (1988) 16:10881-10890) with the following parameters: Matrix BLOSUM62; Open gap 11 and extension gap 1 penalties; gap x_dropoff50; expect 10.0 word size 3; Filter: none.

The fusion protein of the present invention may also comprise variants of allergen fragments. Particular preferred variants of allergen fragments comprise at least one, preferably at least two, more preferably at least three, amino acid exchanges compared to the allergen fragment. Particularly preferred is the exchange of at least one, preferably of at least two, more preferably of at least three, in particular of all, cysteine residues naturally occurring in the allergen fragment with other amino acid residues, preferably with serine, threonine, glycine, alanine, or leucine residues. Thus, a variant of the allergen fragment of the present invention preferably does not contain any cysteine residues.

The allergen fragments within the fusion protein of the present invention may be fused directly to each other or may be separated by a single amino acid residue or a linker peptide consisting of two to 30, preferably two to 20, more preferably two to ten, more preferably two to five, amino acid residues. Also $X_1/X_2$ and the carrier protein Y may be separated by a single amino acid residue or a linker peptide as defined above.

The fusion protein of the present invention can be recombinantly produced in any expression system known in the art. Particularly preferred expression systems include bacteria (e.g. *E. coli*), yeast cells (e.g. *Pichia pastoris*) or insect cells like S2 cells from *Drosophila melanogaster*, Sf9 or Sf21 cells from *Spodoptera frugiperda*, or TNi cells from *Trichoplusia ni*.

The allergen fragments of the fusion protein of the present invention may be derived from any house dust mite. However, it is particularly preferred to use allergens from house dust mites which cause allergic reactions in most people. Therefore, it is preferred that the allergen fragments are derived from allergens of *Dermatophagoides pteronyssinus* and/or *Dermatophagoides farinae*.

According to another preferred embodiment of the present invention the at least two allergens are of *Dermatophagoides pteronyssinus* and selected from the group consisting of Der p 1, Der p 2, Der p 5, Der p 7, Der p 21 and Der p 23.

According to another preferred embodiment of the present invention the at least two allergens are of *Dermatophagoides farinae* and selected from the group consisting of Der f 1, Der f 2, Der f 5, Der f 7, Der f 21 and Der f 23.

Allergic people react differently to allergens derived from the same source. People suffering from house dust mite allergies caused by *Dermatophagoides pteronyssinus* and/or *Dermatophagoides farinae* react to allergens Der p 1 and Der p 2 as well as to Der p 5, Der p 7, Der p 21 and Der p 23 and to allergens Der f 1 and Der f 2 as well as to Der f 5, Der f 7, Der f 21 and Der f 23, respectively. Therefore, it is particularly preferred to provide a fusion protein comprising allergen fragments of one or more of these allergens.

According to a further preferred embodiment of the present invention the allergen fragments of the at least two allergens consist of 25 to 50 amino acid residues, preferably 28 to 48 amino acid residues, more preferably 30 to 45 amino acid residues.

According to a preferred embodiment of the present invention at least one, preferably at least two, more preferably at least three, in particular all, of the cysteine residues of the allergen fragments are substituted with serine, threonine, glycine, alanine, or leucine.

Some or all cysteine residues of the allergen fragments used in the fusion protein of the present invention may be substituted with other amino acid residues. The substitution of one or more cysteine residues may reduce the number of disulphide bonds potentially formed during the recombinant expression of the fusion proteins of the present invention or during its processing (e.g. purification of the fusion protein from inclusion bodies, manufacturing of a vaccine formulation). Furthermore, the substitution of cysteine residues within the allergen fragments results in the reduction or complete removal of free sulphur groups in the fusion protein preventing that such groups are able to react with other compounds.

According to a further preferred embodiment of the present invention the allergen fragment of Der p 1 consists of an amino acid sequence being at least 90%, preferably at least 92%, more preferably at least 95%, more preferably at least 97%, in particular 100%, identical to an amino acid sequence selected from the group consisting of TNACSINGNAPAEIDLRQMRTVTPIRMQGGCGSCWAFSGVA (SEQ ID No. 1), ATESAYLAYRNQSLDLAEQELVDCASQHGCHGDTIPRGIEYIQ (SEQ ID No. 2), HNGVVQESYYRYVAREQSCRRPNAQRFGISN (SEQ ID No. 3), VRNSWDTNWGDNGYGYFAANIDLMMIEEYPYVVIL (SEQ ID No. 4), TNASSINGNAPAEIDLRQMRTVTPIRMQGGSGSSWAFSGVA (SEQ ID No. 5), ATESAYLAYRNQSLDLAEQELVDSASQHGSHGDTIPRGIEYIQ (SEQ ID No. 6) and HNGVVQESYYRYVAREQSSRRPNAQRFGISN (SEQ ID No. 7).

According to another preferred embodiment of the present invention the allergen fragment of Der p 2 consists of an amino acid sequence being at least 90%, preferably at least 92%, more preferably at least 95%, more preferably at least 97%, in particular 100%, identical to an amino acid sequence selected from the group consisting of CHGSEPCIIHRGKPFQLEAVFEANQNSKTAK (SEQ ID No. 8), EVDVPGIDPNACHYMKCPLVKGQQYDIKYTWIVPKIAPKSEN (SEQ ID No. 9), HGSEPSIIHRGKPFQLEAVFEANQNSKTAK (SEQ ID No. 10) and EVDVPGIDPNASHYMKSPLVKGQQYDIKYTWIVPKIAPKSEN (SEQ ID No. 11).

According to a preferred embodiment of the present invention the allergen fragment of Der p 5 consists of an amino acid sequence being at least 90%, preferably at least 92%, more preferably at least 95%, more preferably at least 97%, in particular 100%, identical to an amino acid sequence selected from the group consisting of DYQNEFDFLLMERIHEQIKKGELALFYLQ (SEQ ID No. 12) and EQYNLEMAKKSGDILERDLKKEEARVKKIEV (SEQ ID No. 13).

According to another preferred embodiment of the present invention the fragments of Der p 7 consists of amino acid sequence being at least 90%, preferably at least 92%, more preferably at least 95%, more preferably at least 97%, in particular 100%, identical to amino acid sequence DPIHYDKITEEINKAVDEAVAAIEKSETFD (SEQ ID No. 14).

According to a further preferred embodiment of the present invention the fragments of Der p 21 consists of amino acid sequence being at least 90%, preferably at least 92%, more preferably at least 95%, more preferably at least 97%, in particular 100%, identical to amino acid sequence YNYEFALESIKLLIKKLDELAKKVKAVNPDEYY (SEQ ID No. 15).

According to a preferred embodiment of the present invention the fragments of Der p 23 consists of an amino acid sequence being at least 90%, preferably at least 92%, more preferably at least 95%, more preferably at least 97%, in particular 100%, identical to an amino acid sequence selected from the group consisting of GYFADPKDPHKFYICSNWEAVHKDCPGNTRWNEDEETCT (SEQ ID No. 16) and GYFADPKDPHKFYISSNWEAVHKDSPGNTRWNEDEETST (SEQ ID No. 17).

According to a further preferred embodiment of the present invention the allergen fragment of Der f 1 consists of an amino acid sequence being at least 90%, preferably at least 92%, more preferably at least 95%, more preferably at least 97%, in particular 100%, identical to an amino acid sequence selected from the group consisting of TSACRINSVNVPSELDLRSLRTVTPIRMQGGCGSCWAFSGVA (SEQ ID No. 38), ATESAYLAYRNTSLDLSEQELVDCASQHGCHGDTIPRGIEYIQ (SEQ ID No. 39), QNGVVEERSYPYVAREQQCRRPNSQHYGISN (SEQ ID No. 40) and VRNSWDTTWGDSGYGYFQAGNNLMMIEQYPYVVIM (SEQ ID No. 41).

According to another preferred embodiment of the present invention the allergen fragment of Der f 2 consists of an amino acid sequence being at least 90%, preferably at least 92%, more preferably at least 95%, more preferably at least 97%, in particular 100%, identical to an amino acid sequence selected from the group consisting of HGSDPCI-IHRGKPFNLEAIFDANQNTKTAK (SEQ ID No. 42) and EVDVPGIDTNACHYIKCPLVKGQQYDAKYTWNVP-KIAPKSEN (SEQ ID No. 43)

According to a preferred embodiment of the present invention the allergen fragment of Der f 5 consists of an amino acid sequence being at least 90%, preferably at least 92%, more preferably at least 95%, more preferably at least 97%, in particular 100%, identical to an amino acid sequence selected from the group consisting of DYQNEFD-FLLMQRIHEQMRKGEEALLHLQ (SEQ ID No. 44) and ERYNVEIALKSNEILERDLKKEEQRVKKIEV (SEQ ID No. 45).

According to another preferred embodiment of the present invention the fragments of Der f 7 consists of amino acid sequence being at least 90%, preferably at least 92%, more preferably at least 95%, more preferably at least 97%, in particular 100%, identical to amino acid sequence DPIHYD-KITEEINKAIDDAIAAIEQSETID (SEQ ID No. 46).

According to a further preferred embodiment of the present invention the fragments of Der f 21 consists of amino acid sequence being at least 90%, preferably at least 92%, more preferably at least 95%, more preferably at least 97%, in particular 100%, identical to amino acid sequence YNFETAVSTIEILVKDLAELAKKVKAVKSDD (SEQ ID No. 47).

According to a preferred embodiment of the present invention the fragments of Der f 23 consists of an amino acid sequence being at least 90%, preferably at least 92%, more preferably at least 95%, more preferably at least 97%, in particular 100%, identical to an amino acid sequence selected from the group consisting of GYFADPKDPCKFYICSNWEAIHKSCPGN-TRWNEKELTCT (SEQ ID No. 48).

According to another preferred embodiment of the present invention $X_1$ comprises four allergen fragments of Der p 1 and two fragments of Der p 2 or three fragments of Der p 21 and three fragments of Der p23.

It turned surprisingly out that $X_1$ comprising or consisting of these allergen fragments in any order being fused to the N-terminal end of the carrier protein results in the formation of antibodies being able to inhibit the binding of the respective naturally occurring allergen to allergen specific IgE. This allows to use such a fusion protein as a vaccine to treat or prevent allergic reactions caused by the respective allergens.

According to a further preferred embodiment of the present invention $X_2$ comprises two to four allergen fragments of Der p 1 and two fragments of Der p 2 or four fragments of Der p 5, two fragments of Der p 7.

$X_2$ fused to the C-terminal end of the carrier protein may comprise or consist of the aforementioned allergen fragments in any order. It turned out that such allergen fragments on the C-terminal end of the carrier protein result in a fusion protein inducing the formation of antibodies being able to inhibit the binding of the respective naturally occurring allergen to allergen specific IgE. This allows to use such a fusion protein as a vaccine to treat or prevent allergic reactions caused by the respective allergens.

According to another preferred embodiment of the present invention the fusion protein comprises at least one polypeptide having amino acid sequence selected from the group consisting of SEQ ID No. 18, SEQ ID No. 19, SEQ ID No. 20, SEQ ID No. 21, SEQ ID No. 22, SEQ ID No. 23, SEQ ID No. 24 and/or SEQ ID No. 25.

The polypeptides consisting of amino acid sequences SEQ ID No. 18 and 19 comprise fragments of the allergens Der p 1 and Der p 2:

```
SEQ ID No. 18:
VRNSWDTNWGDNGYGYFAANIDLMMIEEYPYVVILHNGVVQESYYRYVAR

EQSSRRPNAQRFGISNHGSEPSIIHRGKPFQLEAVFEANQNSKTAKHGSE

PSIIHRGKPFQLEAVFEANQNSKTAKVRNSWDTNWGDNGYGYFAANIDLM

MIEEYPYVVILHNGVVQESYYRYVAREQSSRRPNAQRFGISN

SEQ ID No. 19:
EVDVPGIDPNASHYMKSPLVKGQQYDIKYTWIVPKIAPKSENEVDVPGID

PNASHYMKSPLVKGQQYDIKYTWIVPKIAPKSENATESAYLAYRNQSLDL

AEQELVDSASQHGSHGDTIPRGIEYIQTNASSINGNAPAEIDLRQMRTVT

PIRMQGGSGSSWAFSGVAATESAYLAYRNQSLDLAEQELVDSASQHGSHG

DTIPRGIEYIQTNASSINGNAPAEIDLRQMRTVTPIRMQGGSGSSWAFSG
```

The polypeptide consisting of SEQ ID No. 18 may be $X_1$ or $X_2$ in formula (I), whereby in the most preferred embodiment of the present invention said polypeptide is $X_1$ in formula (I).

The polypeptide consisting of SEQ ID No. 19 may be $X_1$ or $X_2$ in formula (I), whereby in the most preferred embodiment of the present invention said polypeptide is $X_2$ in formula (I).

The polypeptides consisting of amino acid sequences SEQ ID No. 20 and 21 comprise fragments of the allergens Der p 5, Der p 7, Der p 21 and Der p 23:

```
SEQ ID No. 20:
YNYEFALESIKLLIKKLDELAKKVKAVNPDEYYYNYEFALESIKLLIKKL

DELAKKVKAVNPDEYYYNYEFALESIKLLIKKLDELAKKVKAVNPDEYYG

YFADPKDPHKFYISSNWEAVHKDSPGNTRWNEDEETSTGYFADPKDPHKF

YISSNWEAVHKDSPGNTRWNEDEETSTGYFADPKDPHKFYISSNWEAVHK

DSPGNTRWNEDEETST

SEQ ID No. 21:
DYQNEFDFLLMERIHEQIKKGELALFYLQDYQNEFDFLLMERIHEQIKKG

ELALFYLQDPIHYDKITEEINKAVDEAVAAIEKSETFDDPIHYDKITEEI

NKAVDEAVAAIEKSETFDEQYNLEMAKKSGDILERDLKKEEARVKKIEVE

QYNLEMAKKSGDILERDLKKEEARVKKIEV
```

The polypeptide consisting of SEQ ID No. 20 may be $X_1$ or $X_2$ in formula (I), whereby in the most preferred embodiment of the present invention said polypeptide is $X_1$ in formula (I).

The polypeptide consisting of SEQ ID No. 21 may be $X_1$ or $X_2$ in formula (I), whereby in the most preferred embodiment of the present invention said polypeptide is $X_2$ in formula (I).

The polypeptides consisting of amino acid sequences SEQ ID No. 22 and 23 comprise fragments of the allergens Der f 1 and Der f 2:

```
SEQ ID No. 22:
VRNSWDTTWGDSGYGYFQAGNNLMMIEQYPYVVIMQNGVVEERSYPYVAR

EQQCRRPNSQHYGISNHGSDPCIIHRGKPFNLEAIFDANQNTKTAKHGSD
```

-continued

PCIIHRGKPFNLEAIFDANQNTKTAKVRNSWDTTWGDSGYGYFQAGNNLM

MIEQYPYVVIMQNGVVEERSYPYVAREQQCRRPNSQHYGISN

SEQ ID No. 23:
EVDVPGIDTNACHYIKCPLVKGQQYDAKYTWNVPKIAPKSENEVDVPGID

TNACHYIKCPLVKGQQYDAKYTWNVPKIAPKSENATESAYLAYRNTSLDL

SEQELVDCASQHGCHGDTIPRGIEYIQTSACRINSVNVPSELDLRSLRTV

TPIRMQGGCGSCWAFSGVAATESAYLAYRNTSLDLSEQELVDCASQHGCH

GDTIPRGIEYIQTSACRINSVNVPSELDLRSLRTVTPIRMQGGCGSCWAF

SGVA

The polypeptide consisting of SEQ ID No. 22 may be $X_1$ or $X_2$ in formula (I), whereby in the most preferred embodiment of the present invention said polypeptide is $X_1$ in formula (I).

The polypeptide consisting of SEQ ID No. 23 may be $X_1$ or $X_2$ in formula (I), whereby in the most preferred embodiment of the present invention said polypeptide is $X_2$ in formula (I).

The polypeptides consisting of amino acid sequences SEQ ID No. 24 and 25 comprise fragments of the allergens Der p 5, Der p 7, Der p 21 and Der p 23:

SEQ ID No. 24:
YNFETAVSTIEILVKDLAELAKKVKAVKSDDYNFETAVSTIEILVKDLAE

LAKKVKAVKSDDYNFETAVSTIEILVKDLAELAKKVKAVKSDDGYFADPK

DPCKFYICSNWEAIHKSCPGNTRWNEKELTCTGYFADPKDPCKFYICSNW

EAIHKSCPGNTRWNEKELTCTGYFADPKDPCKFYICSNWEAIHKSCPGNT

RWNEKELTCT

SEQ ID No. 25:
DYQNEFDFLLMQRIHEQMRKGEEALLHLQDYQNEFDFLLMQRIHEQMRKG

EEALLHLQDPIHYDKITEEINKAIDDAIAAIEQSETIDDPIHYDKITEEI

NKAIDDAIAAIEQSETIDERYNVEIALKSNEILERDLKKEEQRVKKIEVE

RYNVEIALKSNEILERDLKKEEQRVKKIEV

The polypeptide consisting of SEQ ID No. 24 may be $X_1$ or $X_2$ in formula (I), whereby in the most preferred embodiment of the present invention said polypeptide is $X_1$ in formula (I).

The polypeptide consisting of SEQ ID No. 25 may be $X_1$ or $X_2$ in formula (I), whereby in the most preferred embodiment of the present invention said polypeptide is $X_2$ in formula (I).

According to a further preferred embodiment of the present invention the carrier protein is a surface polypeptide of a virus of a hepadnaviridae family or a fragment of the surface polypeptide.

According to a preferred embodiment of the present invention the virus of the hepadnaviridae family is Hepatitis B virus.

According to another preferred embodiment of the present invention the surface polypeptide of the virus of the hepadnaviridae family is PreS.

According to a further preferred embodiment of the present invention the fragment of the surface polypeptide is Hepatitis B PreS1 or Hepatitis B PreS2.

According to a preferred embodiment of the present invention the carrier protein comprises an amino acid sequence which is at least 90%, preferably at least 92%, more preferably at least 95%, more preferably at least 97%, in particular 100%, identical to SEQ ID No. 26.

The carrier protein used in the present invention may comprise or consist of the amino acid sequence SEQ ID No. 26 (GenBank Acc. No. AAT28678.1):

GGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQS

GRQPTPISPPLRDSHPQAMQWNSTAFHQALQDPRVRGLYFPAGGSSSGTV

NPAPNIASHISSISARTGDPVTN

According to another preferred embodiment of the present invention the fusion protein comprises or consists of an amino acid sequence which is at least 90%, preferably at least 92%, more preferably at least 95%, more preferably at least 97%, in particular 100%, identical to SEQ ID No. 27, SEQ ID No. 28, SEQ ID No. 29, SEQ ID No. 30, SEQ ID No. 31, SEQ ID No. 32 or SEQ ID No. 33.

The fusion proteins of the present invention may comprise PreS as carrier protein Y and fragments of various allergens forming two polypeptides $X_1$ and $X_2$, respectively, being located adjacent to the carrier protein (see formula (I)). Particularly preferred fusion proteins comprise fragments of the allergens Der p 1, Der p 2, Der p 5, Der p 7, Der p 21 and Der p 23. Such fusion proteins may comprise of consist of the following amino acid sequences.

SEQ ID No. 27
("Der p 1-2 C3")
VRNSWDTNWGDNGYGYFAANIDLMMIEEYPYVVILHNGVVQESYYRYVAREQSSRRP

NAQRFGISNHGSEPSIIHRGKPFQLEAVFEANQNSKTAKHGSEPSIIHRGKPFQLEA

VFEANQNSKTAKVRNSWDTNWGDNGYGYFAANIDLMMIEEYPYVVILHNGVVQESYY

RYVAREQSSRRPNAQRFGISNGGWSSKPRKGMGTNLSVPNPLGFFPDHQLDPAFGAN

SNNPDWDFNPIKDHWPAANQVGVGAFGPGLTPPHGGILGWSPQAQGILTTVSTIPPP

ASTNRQSGRQPTPISPPLRDSHPQAMQWNSTAFHQALQDPRVRGLYFPAGGSSSGTV

NPAPNIASHISSISARTGDPVTNEVDVPGIDPNASHYMKSPLVKGQQYDIKYTWIVP

KIAPKSENEVDVPGIDPNASHYMKSPLVKGQQYDIKYTWIVPKIAPKSENATESAYL

AYRNQSLDLAEQELVDSASQHGSHGDTIPRGIEYIQTNASSINGNAPAEIDLRQMRT

-continued

VTPIRMQGGSGSSWAFSGVAATESAYLAYRNQSLDLAEQELVDSASQHGSHGDTIPR

GIEYIQTNASSINGNAPAEIDLRQMRTVTPIRMQGGSGSSWAFSG

SEQ ID No. 28
("Der p 572123_P6 (large)")
YNYEFALESIKLLIKKLDELAKKVKAVNPDEYYYNYEFALESIKLLIKKLDELAKKVK

AVNPDEYYYNYEFALESIKLLIKKLDELAKKVKAVNPDEYYGYFADPKDPHKFYISSN

WEAVHKDSPGNTRWNEDEETSTGYFADPKDPHKFYISSNWEAVHKDSPGNTRWNEDEE

TSTGYFADPKDPHKFYISSNWEAVHKDSPGNTRWNEDEETSTGGWSSKPRKGMGTNLS

VPNPLGFFPDHQLDPAFGANSNNPDWDFNPIKDHWPAANQVGVGAFGPGLTPPHGGIL

GWSPQAQGILTTVSTIPPPASTNRQSGRQPTPISPPLRDSHPQAMQWNSTAFHQALQD

PRVRGLYFPAGGSSSGTVNPAPNIASHISSISARTGDPVTNDYQNEFDFLLMERIHEQ

IKKGELALFYLQDYQNEFDFLLMERIHEQIKKGELALFYLQDPIHYDKITEEINKAVD

EAVAAIEKSETFDDPIHYDKITEEINKAVDEAVAAIEKSETFDEQYNLEMAKKSGDIL

ERDLKKEEARVKKIEVEQYNLEMAKKSGDILERDLKKEEARVKKIEV

SEQ ID No. 29
("Der p 1-2 C1")
VRNSWDTNWGDNGYGYFAANIDLMMIEEYPYVVILHNGVVQESYYRYVAREQSSRRP

NAQRFGISNVRNSWDTNWGDNGYGYFAANIDLMMIEEYPYVVILHNGVVQESYYRYV

AREQSSRRPNAQRFGISNHGSEPSIIHRGKPFQLEAVFEANQNSKTAKHGSEPSIIH

RGKPFQLEAVFEANQNSKTAKGGWSSKPRKGMGTNLSVPNPLGFFPDHQLDPAFGAN

SNNPDWDFNPIKDHWPAANQVGVGAFGPGLTPPHGGILGWSPQAQGILTTVSTIPPP

ASTNRQSGRQPTPISPPLRDSHPQAMQWNSTAFHQALQDPRVRGLYFPAGGSSSGTV

NPAPNIASHISSISARTGDPVTNEVDVPGIDPNASHYMKSPLVKGQQYDIKYTWIVP

KIAPKSENEVDVPGIDPNASHYMKSPLVKGQQYDIKYTWIVPKIAPKSENATESAYL

AYRNQSLDLAEQELVDSASQHGSHGDTIPRGIEYIQTNASSINGNAPAEIDLRQMRT

VTPIRMQGGSGSSWAFSGVAATESAYLAYRNQSLDLAEQELVDSASQHGSHGDTIPR

GIEYIQTNASSINGNAPAEIDLRQMRTVTPIRMQGGSGSSWAFSG

SEQ ID No. 30
("Der p 1-2 C2")
VRNSWDTNWGDNGYGYFAANIDLMMIEEYPYVVILHNGVVQESYYRYVAREQSSRRP

NAQRFGISNVRNSWDTNWGDNGYGYFAANIDLMMIEEYPYVVILHNGVVQESYYRYV

AREQSSRRPNAQRFGISNHGSEPSIIHRGKPFQLEAVFEANQNSKTAKHGSEPSIIH

RGKPFQLEAVFEANQNSKTAKGGWSSKPRKGMGTNLSVPNPLGFFPDHQLDPAFGAN

SNNPDWDFNPIKDHWPAANQVGVGAFGPGLTPPHGGILGWSPQAQGILTTVSTIPPP

ASTNRQSGRQPTPISPPLRDSHPQAMQWNSTAFHQALQDPRVRGLYFPAGGSSSGTV

NPAPNIASHISSISARTGDPVTNATESAYLAYRNQSLDLAEQELVDSASQHGSHGDT

IPRGIEYIQTNASSINGNAPAEIDLRQMRTVTPIRMQGGSGSSWAFSGVAEVDVPGI

DPNASHYMKSPLVKGQQYDIKYTWIVPKIAPKSENEVDVPGIDPNASHYMKSPLVKG

QQYDIKYTWIVPKIAPKSENATESAYLAYRNQSLDLAEQELVDSASQHGSHGDTIPR

GIEYIQTNASSINGNAPAEIDLRQMRTVTPIRMQGGSGSSWAFSG

SEQ ID No. 31
("Der p 5.7.21.23_P4P5")
YNYEFALESIKLLIKKLDELAKKVKAVNPDEYYYNYEFALESIKLLIKKLDELAKKV

KAVNPDEYYYNYEFALESIKLLIKKLDELAKKVKAVNPDEYYGYFADPKDPHKFYIC

SNWEAVHKDCPGNTGYFADPKDPHKFYICSNWEAVHKDCPGNTGGWSSKPRKGMGTN

-continued

LSVPNPLGFFPDHQLDPAFGANSNNPDWDFNPIKDHWPAANQVGVGAFGPGLTPPHG

GILGWSPQAQGILTTVSTIPPPASTNRQSGRQPTPISPPLRDSHPQAMQWNSTAFHQ

ALQDPRVRGLYFPAGGSSSGTVNPAPNIASHISSISARTGDPVTNKFYICSNWEAVH

KDCPGNTRWNEDEETCTKFYICSNWEAVHKDCPGNTRWNEDEETCTDYQNEFDFLLM

ERIHEQIKKGELALFYLQDYQNEFDFLLMERIHEQIKKGELALFYLQDPIHYDKITE

EINKAVDEAVAAIEKSETFDDPIHYDKITEEINKAVDEAVAAIEKSETFDEQYNLEM

AKKSGDILERDLKKEEARVKKIEVEQYNLEMAKKSGDILERDLKKEEARVKKIEV

SEQ ID No. 32
("Der p 5_7_21 C1")
YNYEFALESIKLLIKKLDELAKKVKAVNPDEYYYNYEFALESIKLLIKKLDELAKKV

KAVNPDEYYYNYEFALESIKLLIKKLDELAKKVKAVNPDEYYYNYEFALESIKLLIK

KLDELAKKVKAVNPDEYYDPIHYDKITEEINKAVDEAVAAIEKSETFDDPIHYDKIT

EEINKAVDEAVAAIEKSETFDGGWSSKPRKGMGTNLSVPNPLGFFPDHQLDPAFGAN

SNNPDWDFNPIKDHWPAANQVGVGAFGPGLTPPHGGILGWSPQAQGILTTVSTIPPP

ASTNRQSGRQPTPISPPLRDSHPQAMQWNSTAFHQALQDPRVRGLYFPAGGSSSGTV

NPAPNIASHISSISARTGDPVTNDYQNEFDFLLMERIHEQIKKGELALFYLQDYQNE

FDFLLMERIHEQIKKGELALFYLQDPIHYDKITEEINKAVDEAVAAIEKSETFDDPI

HYDKITEEINKAVDEAVAAIEKSETFDEQYNLEMAKKSGDILERDLKKEEARVKKIE

VEQYNLEMAKKSGDILERDLKKEEARVKKIEV

SEQ ID No. 33
("Der p 5_7_21 C2")
YNYEFALESIKLLIKKLDELAKKVKAVNPDEYYYNYEFALESIKLLIKKLDELAKKV

KAVNPDEYYYNYEFALESIKLLIKKLDELAKKVKAVNPDEYYYNYEFALESIKLLIK

KLDELAKKVKAVNPDEYYDYQNEFDFLLMERIHEQIKKGELALFYLQDYQNEFDFLL

MERIHEQIKKGELALFYLQGGWSSKPRKGMGTNLSVPNPLGFFPDHQLDPAFGANSN

NPDWDFNPIKDHWPAANQVGVGAFGPGLTPPHGGILGWSPQAQGILTTVSTIPPPAS

TNRQSGRQPTPISPPLRDSHPQAMQWNSTAFHQALQDPRVRGLYFPAGGSSSGTVNP

APNIASHISSISARTGDPVTNDPIHYDKITEEINKAVDEAVAAIEKSETFDDPIHYD

KITEEINKAVDEAVAAIEKSETFDDPIHYDKITEEINKAVDEAVAAIEKSETFDDPI

HYDKITEEINKAVDEAVAAIEKSETFDEQYNLEMAKKSGDILERDLKKEEARVKKIE

VEQYNLEMAKKSGDILERDLKKEEARVKKIEV

SEQ ID No. 36
("Der f 1/2 C3")
VRNSWDTTWGDSGYGYFQAGNNLMMIEQYPYVVIMQNGVVEERSYPYVAREQQSRRP

NSQHYGISNHGSDPSIIHRGKPFNLEAIFDANQNTKTAKHGSDPSIIHRGKPFNLEA

IFDANQNTKTAKVRNSWDTTWGDSGYGYFQAGNNLMMIEQYPYVVIMQNGVVEERSY

PYVAREQQSRRPNSQHYGISNGGWSSKPRKGMGTNLSVPNPLGFFPDHQLDPAFGAN

SNNPDWDFNPIKDHWPAANQVGVGAFGPGLTPPHGGILGWSPQAQGILTTVSTIPPP

ASTNRQSGRQPTPISPPLRDSHPQAMQWNSTAFHQALQDPRVRGLYFPAGGSSSGTV

NPAPNIASHISSISARTGDPVTNEVDVPGIDTNASHYIKSPLVKGQQYDAKYTWNVP

KIAPKSENEVDVPGIDTNASHYIKSPLVKGQQYDAKYTWNVPKIAPKSENATESAYL

-continued

```
AYRNTSLDLSEQELVDSASQHGSHGDTIPRGIEYIQTSASRINSVNVPSELDLRSLR

TVTPIRMQGGSGSSWAFSGVAATESAYLAYRNTSLDLSEQELVDSASQHGSHGDTIP

RGIEYIQTSASRINSVNVPSELDLRSLRTVTPIRMQGGSGSSWAFSG
```

SEQ ID No. 37
("Der f 5 7 21 23_P6")
```
YNFETAVSTIEILVKDLAELAKKVKAVKSDDYNFETAVSTIEILVKDLAELAKKVKA

VKSDDYNFETAVSTIEILVKDLAELAKKVKAVKSDDGYFADPKDPSKFYISSNWEAI

HKSSPGNTRWNEKELTSTGYFADPKDPSKFYISSNWEAIHKSSPGNTRWNEKELTST

GYFADPKDPSKFYISSNWEAIHKSSPGNTRWNEKELTSTGGWSSKPRKGMGTNLSVP

NPLGFFPDHQLDPAFGANSNNPDWDFNPIKDHWPAANQVGVGAFGPGLTPPHGGILG

WSPQAQGILTTVSTIPPPASTNRQSGRQPTPISPPLRDSHPQAMQWNSTAFHQALQD

PRVRGLYFPAGGSSSGTVNPAPNIASHISSISARTGDPVTNDYQNEFDFLLMQRIHE

QMRKGEEALLHLQDYQNEFDFLLMQRIHEQMRKGEEALLHLQDPIHYDKITEEINKA

IDDAIAAIEQSETIDDPIHYDKITEEINKAIDDAIAAIEQSETIDERYNVEIALKSN

EILERDLKKEEQRVKKIEVERYNVEIALKSNEILERDLKKEEQRVKKIEV
```

Another aspect of the present invention relates to a pharmaceutical preparation (i.e. vaccine formulation) comprising at least one fusion protein according to the present invention.

According to a preferred embodiment of the present invention the preparation comprises a fusion protein comprising amino acid sequence SEQ ID No. 27 and a fusion protein comprising amino acid sequence SEQ ID No. 28.

According to a further preferred embodiment of the present invention said preparation comprises 10 ng to 1 g, preferably 100 ng to 10 mg, especially 0.5 µg to 200 µg of the fusion protein of the present invention or a nucleic acid molecule encoding said fusion protein or a vector comprising said nucleic acid molecule.

According to a particularly preferred embodiment of the present invention the fusion protein of the present invention is administered to an individual at least once in an amount of 0.01 pg/kg body weight to 5 mg/kg body weight, preferably 0.1 pg/kg body weight to 2 mg/kg body weight.

According to further preferred embodiment of the present invention the fusion protein is administered to a patient in an amount of 5 to 100 µg, preferably 10 to 80 µg, more preferably 10 to 40 µg, either independent from the body weight (i.e. a dose may comprise 15, 20, 25, 30, or 80 µg) or per kg body weight.

The amount of fusion protein that may be combined with excipients to produce a single dosage form will vary depending upon the host treated and the particular mode of administration. The dose of the polypeptide construct may vary according to factors such as the disease state, age, sex and weight of the individual, and the ability to elicit the desired antibody response in the individual. The dosage regime may be adjusted to provide the optimum therapeutic response. For example, several divided doses may be administered daily or the dose may be proportionally reduced as indicated by the exigencies of the therapeutic situation. The dose of the polypeptide construct may also be varied to provide optimum preventative dose response depending upon the circumstances. For instance, the fusion protein of the present invention may be administered to an individual at intervals of several days, one or two weeks or even months depending always on the level of allergen specific IgG induction.

In a preferred embodiment of the present invention the fusion protein and the pharmaceutical preparation of the present invention are applied between 2 and 10, preferably between 2 and 7, even more preferably up to 5 times. In a further preferred embodiment of the present invention, single booster applications are given between 3 months and 5 years following the first dosing schedule. These booster application may be repeated between 2 and 10 times, preferably between 2 and 5 times and most preferably between 2 and 3 times. In a particularly preferred embodiment the time interval between the subsequent vaccinations is chosen to be between 2 weeks and 5 years, preferably between 3 weeks and up to 3 years, more preferably between 3 weeks and 1 year. The repeated administration of the fusion protein of the present invention may maximize the final effect of the treatment.

In a particularly preferred embodiment of the present invention the fusion protein and/or the pharmaceutical preparation of the present invention may be applied using 3 to 6, preferably 5, monthly injections followed by booster injections as mentioned above given every 1 to 6, preferably 3 to 4 months, for at least one, preferably at least two, more preferably from two to six, more preferably from three to five years.

According to another preferred embodiment of the present invention said preparation further comprises at least one adjuvant, pharmaceutical acceptable excipient and/or preservative.

The fusion protein and the pharmaceutical preparation of the present invention can be administrated subcutaneously, intramuscularly, intravenously, mucosally etc. Depending on the dosage form and administration route the polypeptide construct of the present invention may be combined with excipients, diluents, adjuvants and/or carriers. A preferred adjuvant is aluminum hydroxide. Suitable protocols for the production of vaccine formulations are known to the person skilled in the art and can be found e.g. in "Vaccine Protocols" (A. Robinson, M. P. Cranage, M. Hudson; Humana Press Inc., U. S.; 2nd edition 2003).

The fusion protein of the present invention may be formulated also with other adjuvants regularly used in vaccines. For instance, suitable adjuvants may be MF59, aluminum phosphate, calcium phosphate, cytokines (e.g. IL2, IL-12, GM-CSF), saponins (e.g. QS21), MDP derivatives, CpG oligonucleotides, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes. Suitable adjuvants are commercially available as, for example, ASO1B (MPL and QS21 in a liposome formulation), ASO2A, AS15, AS-2, AS-03 and derivatives thereof (GlaxoSmithKline, USA); CWS (cell-wall skeleton), TDM (trehalose-6,6'-dimycolate), LeIF (Leishmania elongation initiation factor), aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin -2, -7 or -12 may also be used as adjuvants. Preferred adjuvants for use in eliciting a predominantly Th1-type response include, for example, a combination of monophosphoryl lipid A, preferably 3-0-deacylated monophosphoryl lipid A (3D-MPL), optionally with an aluminum salt. Aqueous formulations comprising monophosphoryl lipid A and a surfactant have been described in WO 98/43670.

Another preferred adjuvant is a saponin or saponin mimetic] or derivatives, preferably QS21 (Aquila Biopharmaceuticals Inc.), which may be used alone or in combination with other adjuvants. For example, an enhanced system involves the combination of a monophosphoryl lipid A and saponin derivative, such as the combination of QS21 and 3D-MPL. Other preferred formulations comprise an oil-in-water emulsion and tocopherol. A particularly potent adjuvant formulation is QS21, 3D-MPL and tocopherol in an oil-in-water emulsion. Additional saponin adjuvants for use in the present invention include QS7 (described in WO 96/33739 and WO 96/11711) and QS17 (described in U.S. Pat. No. 5,057,540 and EP 0 362 279 B1).

The pharmaceutical preparation of the present invention comprises most preferably aluminum hydroxide as adjuvant.

Another aspect of the present invention relates to a nucleic acid molecule encoding a fusion protein according to the present invention. The nucleic acid molecule of the present invention can be an RNA or a DNA molecule. The nucleic acid molecule may be part of a vector (e.g. protein expression vector, integration vector, cloning vector) which can be transfected or introduced in any kind of biological cell. Preferred cells include bacterial cells such as *Escherichia coli*, yeast cells such as *Pichia pastoris* or *Saccharomyces cerevisiae*, plant cells, mammal cells and insect cells. Means and methods for obtaining such nucleic acid molecules, vectors and cells are well known to the person skilled in the art.

The nucleic acid molecule encoding a fusion protein according to the present invention can also be used directly for vaccinating subjects in need thereof. These nucleic acid molecules may be RNA and/or DNA molecules.

A further aspect of the present invention relates to a vector comprising a nucleic acid molecule according to the present invention.

According to a preferred embodiment of the present invention said vector is an expression or a cloning vector. The vector can be a bacterial, insect, viral or mammalian vector.

The vector of the present invention may preferably be employed for cloning and expression purposes in various hosts like bacteria, yeasts, filamentous fungi, mammalian cells, insect cells, plant cells or any other prokaryotic or eukaryotic cells. Therefore, said vector comprises besides a nucleic acid encoding for a fusion protein according to the present invention host specific regulatory sequences.

Yet another aspect of the present invention relates to a host cell comprising a nucleic acid molecule or a vector according to the present invention.

A further aspect of the present invention relates to a fusion protein according to or pharmaceutical preparation according to the present invention for the use in the treatment or the prevention of an allergy caused by an allergen of a house dust mite, in particular caused by Der p 1, Der p 2, Der p 5, Der p 7, Der p 21 or Der p 23.

The terms "preventing" and "prevention", as used herein, refer to the prevention or inhibition of the recurrence, onset and development of an allergy or a symptom thereof in a subject resulting from the administration of the fusion protein or pharmaceutical preparation according to the present invention. In some embodiments "preventing" and "prevention" refers to the reduction of the risk to develop an allergy against specific allergens. The term "preventing" covers measures not only to prevent the occurrence of an allergy, but also to arrest its progress and reduce its consequences once established.

The terms "treatment" and "treating", as used herein, refer to the reduction or inhibition of the progression and duration of an allergy, the reduction or amelioration of the severity of the allergy and the amelioration of one or more symptoms thereof. "Treatment" encompasses also the improvement and/or reversal of the symptoms of an allergy or allergic reactions. A fusion protein which causes an improvement in any parameter associated with allergy may be identified as a therapeutic fusion protein or conjugate. The term "treatment" refers to both therapeutic treatment and prophylactic measures. For example, those who may benefit from treatment with compositions and methods of the present invention include those already with an allergy as well as those in which the allergy is to be prevented.

The present invention is further illustrated by the following examples, however, without being restricted thereto.

EXAMPLES

Example 1: Design of Allergen Fragments to be Used in the Fusion Proteins of the Present Invention Peptides spanning the allergen sequence of interest were identified based on the prediction of surface exposure of amino acids as determined by ProtScale bioinformatics tool from the ExPASY server (http://web.expasy.org/protscale/). If peptides contained no cysteine residues in their sequence cysteines were added at their N- or C-terminus in order to allow them to couple to keyhole limpet hemocyanin (KLH). Peptides were synthesized using an Applied Biosystems peptide synthesizer Model 433A (Foster City, USA) and subsequently purified by preparative High-performance liquid chromatography (HPLC) (Dionex, Thermofischer Scientific, USA) (Focke et al., FASEB J. 2001; 15(11):2042-4). The size and identity of the peptides were confirmed by mass spectrometry (Bruker, Austria).

Table I lists allergen fragments derived from house dust mite allergens Der p 1 (TNACSINGNA-PAEIDLRQMRTVTPIRMQGGCGSCWAFSGVAATE- SAYLAYRNQSLD LAEQELVDCASQHGCHGDTIPR-GIEYIQHNGVVQESYYRYVAREQSCRRPNAQRFGISNYCQIYPPNVNKIREALAQTHSAI-AVIIGIKDLDAFRHYDGRTIIQRDNGYQPNYH AVNIVGYSNAQGVDYWIVRN-SWDTNWGDNGYGYFAANIDLMMIEEYPYVVIL; SEQ ID No. 34), Der p 2 (DQVDVKDCANHEIKKVLVPGCH-GSEPCIIHRGKPFQLEAVFEANQNSKTAKIEIKA SIEG-LEVDVPGIDPNACHYMKCPLVKGQQYDIKYTWIVP-KIAPKSENVVVTVKVMet GDNGVLACAIATHAKIRD; SEQ ID No. 35), Der p 5 (GenBank Acc. No.: X17699), Der p 7 (GenBank Acc. No.: U37044), Der p (GenBank Acc. No.: DQ354124) and Der p 23 (GenBank Acc. No.: EU414751.1) which were tested in regard to IgE reactivity, basophil activation, immunogenicity and blocking of allergen specific IgE molecules.

TABLE I

Allergen fragments

| peptides | Position on allergen | SEQ ID No. | Amino acid sequence |
|---|---|---|---|
| Der p 1 | | | |
| Der p 1 P1 | 1-41 | 1 | TNACSINGNAPAEIDLRQMRTVIPIRMQGGCGSCWAFSGVA |
| Der p 1 P1 | 1-41 | 5 | TNASSINGNAPAEIDLRQMRTVIPIRMQGGSGSSWAFSGVA |
| Der p 1 P2 | 42-84 | 2 | ATESAYLAYRNQSLDLAEQELVDCASQHGCHGDTIPRGIEYIQ |
| Der p 1 P2 | 42-84 | 6 | ATESAYLAYRNQSLDLAEQELVDSASQHGSHGDTIPRGIEYIQ |
| Der p 1 P3 | 85-115 | 3 | HNGVVQESYYRYVAREQSCRRPNAQRFGISN |
| Der p 1 P3 | 85-115 | 7 | HNGVVQESYYRYVAREQSSRRPNAQRFGISN |
| Der p 1 P4 | 99-135 | 49 | REQSCRRPNAQRFGISNYCQIYPPNVNKIREALAQTH |
| Der p 1 P5 | 145-175 | 50 | KDLDAFRHYDGRTIIQRDNGYQPNYHAVNIV |
| Der p 1 P6 | 155-187 | 51 | GRTIIQRDNGYQPNYHAVNIVGYSNAQGVDYWI |
| Der p 1 P7 | 175-208 | 52 | VGYSNAQGVDYWIVRNSWDTNWGDNGYGYFAANI |
| Der p 1 P8 | 188-222 | 4 | VRNSWDTNWGDNGYGYFAANIDLMMIEEYPYVVIL |
| Der p 2 | | | |
| Der p 2 P1 | 1-33 | 53 | DQVDVKDCANHEIKKVLVPGCHGSEPCIIHRGK |
| Der p 2 P2 | 21-51 | 8 | CHGSEPCIIHRGKPFQLEAVFEANQNSKTAK |
| Der p 2 P2a | 22-51 | 10 | HGSEPSIIHRGKPFQLEAVFEANQNSKTAK |
| Der p 2 P3 | 42-73 | 54 | EANQNSKTAKIEIKASIEGLEVDVPGIDPNAC |
| Der p 2 P4 | 62-103 | 9 | EVDVPGIDPNACHYMKCPLVKGQQYDIKYTWIVPKIAPKSEN |
| Der p 2 P4a | 62-103 | 11 | EVDVPGIDPNASHYMKSPLVKGQQYDIKYTWIVPKIAPKSEN |
| Der p 2 P5 | 98-129 | 55 | APKSENVVVTVKVMGDNGVLACAIATHAKIRD |
| Der p 5 | | | |
| Der p 5 P1 | 1-34 | 56 | EDKKHDYQNEFDFLLMERIHEQIKKGELALFYLQ |
| Der p 5 P2 | 24-59 | 57 | KKGELALFYLQEQINHFEEKPTKEMDKIVAEMDTI |
| Der p 5 P3 | 64-94 | 58 | DGVRGVLDRLMQRKDLDIFEQYNLEMAKKSG |
| Der p 5 P4 | 78-113 | 59 | DLDIFEQYNLEMAKKSGDILERDLKKEEARVKKIEV |
| Der p 5 P1-1 | 1-29 | 60 | EDKKHDYQNEFDFLLMERIHEQIKKGELA |
| Der p 5 P1-2 | 6-34 | 12 | DYQNEFDFLLMERIHEQIKKGELALFYLQ |
| Der p 5 P4-1 | 78-108 | 61 | DLDIFEQYNLEMAKKSGDILERDLKKEEARV |
| Der p 5 P4-2 | 83-113 | 13 | EQYNLEMAKKSGDILERDLKKEEARVKKIEV |
| Der p 21 | | | |
| Der p 21 P1 | 1-34 | 62 | FIVGDKKEDEWRMAFDRLMMEELETKIDQVEKGL |
| Der p 21 P2 | 35-71 | 63 | LHLSEQYKELEKTKSKELKEQILRELTIGENFMKGAL |
| Der p 21 P3 | 67-95 | 64 | MKGALKFFEMEAKRTDLNMFERYNYEFAL |
| Der p 21 P4 | 89-121 | 15 | YNYEFALESIKLLIKKLDELAKKVKAVNPDEYY |
| Der p 7 | | | |
| Der p 7 P1 | 1-30 | 14 | DPIHYDKITEEINKAVDEAVAAIEKSETFD |
| Der p 7 P2 | 20-50 | 65 | VAAIEKSETFDPMKVPDHSDKFERHIGIIDL |
| Der p 7 P3 | 50-80 | 66 | LKGELDMRNIQVRGLKQMKRVGDANVKSEDG |
| Der p 7 P4 | 90-125 | 67 | VHDDVVSMEYDLAYKLGDLHPNTHVISDIQDFVVEL |
| Der p 7 P5 | 123-148 | 68 | VELSLEVSEEGNMTLTSFEVRQFANV |
| Der p 7 P6 | 149-176 | 69 | VNHIGGLSILDPIFAVLSDVLTAIFQDT |
| Der p 7 P7 | 170-198 | 70 | TAIFQDTVRAEMTKVLAPAFKKELERNNQ |
| Der p 23 | | | |
| Der p 23 P1 | 1-32 | 71 | MANDNDDDPTTTVHPTTTEQPDDKFECPSRFG |
| Der p 23 P2 | 15-48 | 72 | PTTTEQPDDKFECPSRFGYFADPKDPHKFYICSN |
| Der p 23 P3 | 32-70 | 16 | GYFADPKDPHKFYICSNWEAVHKDCPGNTRWNEDEETCT |
| Der p 23 P3a | 32-70 | 73 | GYFADPKDPHKFAICSNWAAVHKACPGNTRWNAAAATCT |
| Der p 23 P3b | 32-37 | 74 | GYFADPKDPHAFYICSNWEAVAADCPGNTRWNEDEETCT |
| Der p 23 P4 | 32-60 | 75 | GYFADPKDPHKFYICSNWEAVHKDCPGNT |
| Der p 23 P4a | 32-60 | 76 | GYFADPKDPHKFYISSNWEAVHKDSPGNT |
| Der p 23 P5 | 42-70 | 77 | KFYICSNWEAVHKDCPGNTRWNEDEETCT |
| Der p 23 P5a | 42-70 | 78 | KFYISSNWEAVHKDSPGNTRWNEDEETST |

TABLE I-continued

Allergen fragments

| peptides | Position on allergen | SEQ ID No. | Amino acid sequence |
|---|---|---|---|
| Der p 23 P5b | 47-70 | 79 | SNWEAVHKDCPGNTRWNEDEETCT |
| Der p 23 P6 | 32-70 | 17 | GYFADPKDPHKFYISSNWEAVHKDSPGNTRWNEDEETST |
| Der p 23 P7 | 32-64 | 80 | GYFADPKDPHKFYICSNWEAVHKDCPGNTRWNE |
| Der p 23 P8 | 32-68 | 81 | GYFADPKDPHKFYICSNWEAVHKDCPGNTRWNEDEET |
| Der f 1 | | | |
| Der f 1 P1 | | 38 | TSACRINSVNVPSELDLRSLRTVTPIRMQGGCGSCWAFSGVA |
| Der f 1 P2 | | 39 | ATESAYLAYRNTSLDLSEQELVDCASQHGCHGDTIPRGIEYIQ |
| Der f 1 P3 | | 40 | QNGVVEERSYPYVAREQQCRRPNSQHYGISN |
| Der f 1 P8 | | 41 | VRNSWDTTWGDSGYGYFQAGNNLMMIEQYPYVVIM |
| Der f 2 | | | |
| Der f 2 P2a | | 42 | HGSDPCIIHRGKPFNLEAIFDANQNTKTAK |
| Der f 2 P4a | | 43 | EVDVPGIDTNACHYIKCPLVKGQQYDAKYTWNVPKIAPKSEN |
| Der f 5 | | | |
| Der f 5 P1-2 | | 44 | DYQNEFDFLLMQRIHEQMRKGEEALLHLQ |
| Der f 5 P4-2 | | 45 | ERYNVEIALKSNEILERDLKKEEQRVKKIEV |
| Der f 7 | | | |
| Der f 7 P1 | | 46 | DPIHYDKITEEINKAIDDATAAIEQSETID |
| Der f 21 | | | |
| Der f 21 P4 | | 47 | YNFETAVSTIEILVKDLAELAKKVKAVKSDD |
| Der f 23 | | | |
| Der f 23 P6 | | 48 | GYFADPKDPCKFYICSNWEAIHKSCPGNTRWNEKELTCT |

IgE reactivity of peptides was determined by dot blot analysis. For this purpose 0.5 µg aliquots of each peptide, of corresponding allergen and as a control human serum albumin (HSA) were dotted onto Whatman Protran nitrocellulose membrane (GE healthcare, Little Chalfont, UK). After blocking three times for 20 min with gold buffer (50 mM sodium phosphate [pH 7.4], 0.5% [v/v] Tween-20, 0.5% [w/v] BSA, and 0.05% [w/v] sodium azide), membranes were incubated with HDM-allergic patients' sera (1:10 in gold buffer) or with serum from a non-allergic person (1:10 in gold buffer) overnight at 4° C. Bound IgE antibodies were detected with 1:10 diluted I125-labeled antihuman IgE Abs (Demeditec Diagnostics, Kiel, Germany) and visualized by autoradiography (Kodak XOMAT film).

To determine the immunogenicity of the peptides rabbits were immunized three times (first booster injection after 4 weeks and a second booster injection after 7 weeks) with each of the KLH-conjugated peptides (200 µg/injection) and, for control purposes, with respective allergen (200 µg/injection) using once Freund's complete and twice Freund's incomplete adjuvant (Charles River, Chatillon sur Chalaronnne, France) and/or Al(OH)$_3$ (Serva). Rabbit immune responses were analyzed by ELISA titrations. For the measurement of specific rabbit IgG antibodies, ELISA plates were coated overnight with respective allergen. After blocking, the plates were incubated overnight with serial dilutions of the corresponding rabbit anti-sera, or serum from a non-immunized rabbit (1:500, 1:2.000, 1:10.000 and 1:20.000). Bound rabbit IgG antibodies were detected with a 1:1.000 diluted horseradish peroxidase-labelled donkey anti-rabbit IgG antiserum (Amersham Biosciences, Little Chalfont, UK).

To determine the blocking capacity of peptide IgGs ELISA plates (Nunc, Roskilde, Denmark) coated overnight with 1 µg/mL of respective allergen were pre-incubated for 24 hours with each of the anti-peptide antisera, antiallergen antiserum, or, for control purposes, with serum from a non-immunized rabbit (all in a dilution of 1:50) and then washed. After overnight incubation with sera from HDM allergic patients (diluted 1:10), bound IgE antibodies were detected with horseradish peroxidase-labelled goat anti-human IgE antibodies (KPL, Gaithersburg, Md.). The percentage reduction of IgE binding achieved by pre-incubation with rabbit antisera was calculated as follows: 100−(ODI/ODP)×100). ODI and ODP represent optical density values after pre-incubation with the rabbit immune serum or normal rabbit serum, respectively.

To test the allergenic activity of the peptides, rat basophil leukemia cells (RBL) expressing human high-affinity IgE receptor FcεRI (1×10$^5$/well) were loaded overnight with sera from the HDM-allergic patients and, for control purposes, with the serum from one non-allergic individual at a dilution of 1:10. Cells were washed three times with Tyrode's buffer (Sigma, Austria) and exposed to serial dilutions of allergen and peptides for 1 h. Supernatants were analysed for β-hexosaminidase activity as described previously(. Experiments were carried out in triplicates, and results are presented as mean percentages of total β-hexosaminidase released after addition of 1% Triton X-100+/− SE of the mean (SEM).

TABLE II

| peptides | IgE reactivity (dot blot) | basophil activation | immunogenicity | blocking of IgE |
|---|---|---|---|---|
| Der p 1 | | | | |
| Der p 1 P1 | − | − | yes | 52% CFA |
| Der p 1 P2 | − | − | yes | 51% CFA |
| Der p 1 P3 | − | − | yes | 19% CFA |
| Der p 1 P4 | − | − | yes | 25% CFA |

TABLE II-continued

| peptides | IgE reactivity (dot blot) | basophil activation | immuno-genicity | blocking of IgE |
|---|---|---|---|---|
| Der p 1 P5 | − | − | yes | 18% CFA |
| Der p 1 P6 | − | − | yes | 4% CFA |
| Der p 1 P7 | − | − | yes | 35% CFA |
| Der p 1 P8 | − | − | yes | 45% CFA |
| Der p 2 | | | | |
| Der p 2 P1 | − | − | yes | 41% CFA |
| Der p 2 P2 | − | − | yes | 70% CFA |
| Der p 2 P3 | − | − | yes | 78% CFA |
| Der p 2 P4 | − | − | yes | 73% CFA |
| Der p 2 P5 | − | − | poor | 3% CFA |
| Der p 5 | | | | |
| Der p 5 P1 | + | nd | yes | 35% AlOH, 53% CFA |
| Der p 5 P2 | − | − | yes | 23% AlOH, 37% CFA |
| Der p 5 P3 | + | − | yes | 31% AlOH, 69% CFA |
| Der p 5 P4 | + | nd | yes | 42% AlOH, 83% CFA |
| Der p 5 P1-1 | + | nd | nd | nd |
| Der p 5 P1-2 | − | − | yes | 45% AlOH, 69% CFA |
| Der p 5 P4-1 | + | nd | nd | nd |
| Der p 5 P4-2 | − | nd | yes | 45% AlOH, 78% CFA |
| Der p 21 | | | | |
| Der p 21 P1 | + | − | yes | 54% AlOH, 55% CFA |
| Der p 21 P2 | + | − | yes | 14% AlOH, 39% CFA |
| Der p 21 P3 | + | − | poor | <10% |
| Der p 21 P4 | − | − | yes | 64% AlOH, 81% CFA |
| Der p 7 | | | | |
| Der p 7 P1 | − | − | yes | 66% AlOH, 65% CFA |
| Der p 7 P2 | − | − | yes | 26% AlOH, 62% CFA |
| Der p 7 P3 | − | − | yes | 26% AlOH, 33% CFA |
| Der p 7 P4 | − | − | yes | 15% AlOH, 46% CFA |
| Der p 7 P5 | − | − | poor | 0% AlOH, 0% CFA |
| Der p 7 P6 | − | − | poor | 5% AlOH, 9% CFA |
| Der p 7 P7 | − | − | yes | 22% AlOH, 52% CFA |
| Der p 23 | | | | |
| Der p 23 P1 | − | − | poor | nd |
| Der p 23 P2 | − | − | yes | 19% |
| Der p 23 P3 | + | nd | yes | nd |
| Der p 23 P3a | + | nd | poor | nd |
| Der p 23 P3b | + | nd | no | nd |
| Der p 23 P4 | − | − | yes | 33% |
| Der p 23 P4a | * | * | * | * |
| Der p 23 P5 | + | − | yes | 39% |
| Der p 23 P5a | * | * | * | * |
| Der p 23 P5b | * | * | * | * |
| Der p 23 P6 | − | nd | yes | 70% |
| Der p 23 P7 | − | nd | yes | 5% |
| Der p 23 P8 | − | nd | yes | 6% | nd: not done; bold and underlined letters: cysteine residues replaced with serine or alanine residues; + indicates IgE reactivity; − indicates no IgE reactivity or no basophil activation.

Example 2: Recombinant Production of Proteins

Genes (codon-optimized for *Escherichia coli* expression) coding for fusion proteins Der p 1-2 C3 and Der p 5 7 21 23_P6 (large) were synthesized (ATG: biosynthetics, Merzhausen, Germany and GenScript, Piscataway, USA) and inserted into the NdeI/XhoI sites of pET-27b (Novagen, Germany). Recombinant proteins were expressed in *E.coli* strain BL21-Gold (DE3). Der p 1-2 C3 (see FIG. 1; SEQ ID No. 27) expression was induced at OD600 0.4 by adding 0.5 mM IPTG to bacterial cultures and incubating for 3 h at 37° C. Der p 5 7 21 23_P6 (large) (see FIG. 1; SEQ ID No. 28) was induced at OD600 0.6 by adding 1 mM IPTG and incubating cultures for 2.5 h at 37° C.

Upon harvesting and adding protease inhibitors, inclusion body preparation was performed to remove soluble bacterial proteins. Pellets containing partially purified Der p 1-2 C3 proteins were dissolved in 6M Urea, 10 mM Tris PH 8, 4% and isopropanol and purification was continued by anion exchange chromatography using a HiTrap DEAE Sepharose FF (GE healthcare) column. Elution of the protein from the column was achieved with linearly increasing NaCl concentration. Elution fractions of high purity were united and stepwise dialysis was performed to remove urea and salts and to enable proteins refolding without aggregation. Der p 1-2 C3 protein was incubated for a minimum of 4-5 h at 4° C. subsequently in the following solutions: 1) 6M Urea, 154 mM NaCl, 10 mM Tris PH 8, 4% isopropanol, 2)4M Urea, 103 mM NaCl, 2 mM Hepes, PH 8, 3) 2M Urea, 50.2 mM NaCl, 2 mM Hepes, PH 8, 4) 1M Urea, 25 mM NaCl, 2 mM Hepes, PH 8, 5) 0.5M Urea, 12.5 mM NaCl, 2 mM Hepes, PH 8, 6) 2 mM Hepes, PH 8.

Cell lysate containing Der p 5 7 21 23_P6 (large) was dissolved in in 6M Urea, 10 mM Tris PH 7.5, 4% isopropanol were applied to HiTrap DEAE Sepharose FF (GE healthcare) column and elution of the protein from the column was achieved with linearly increasing NaCl concentration. Pure fractions were united and dialyzed as follows. Stepwise dialysis conditions Der p 5 7 21 23_P6 (large): incubate protein for minimum of 4-5 h at 4° C. subsequently in the following solutions: 1) 6M Urea, 100 mM NaCl, 10 mM Tris PH 7.5, 4% isopropanol, 2)4M Urea, 100 mM NaCl, 2 mM Hepes, PH 7.5, 3) 2M Urea, 100 mM NaCl, 2 mM Hepes, PH 7.5, 4) 1M Urea, 100 mM NaCl, 2 mM Hepes, PH 7.5, 5) 0.5M Urea, 100 mM NaCl, 2 mM Hepes, PH 7.5, 6) 100 mM NaCl, 2 mM Hepes, PH 7.5, 7) 50 mM NaCl, 2 mM Hepes, PH 7.5, 8) 25 mM NaCl, 2 mM Hepes, PH 7.5, 9) 12.5 mM NaCl, 2 mM Hepes, PH 7.5, 10) 2 mM Hepes, PH 7.5.

Figure 2:
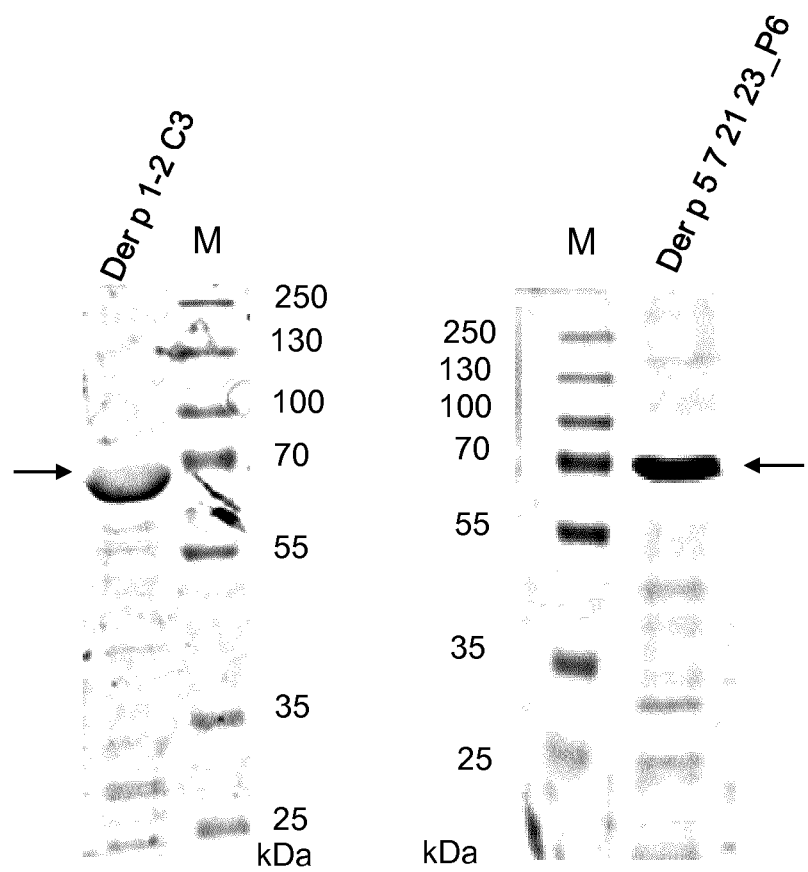
FIG. 2 shows the purified PreS fusion proteins analyzed by SDS-PAGE.

Purity of the proteins was checked by SDS-PAGE and Coomasie staining (see FIG. 2). Size exclusion chromatography was used to confirm that no oligomerization of the refolded proteins occurs.

Example 3: Determination of IgE Reactivity

IgE reactivity of the constructs of example 2 was determined by immunoblot (Curin M, et al. Sci Rep. 22(2017): 12135). Aliquots containing 0.5 µg of purified nDer p 1 (a natural isolate; Accession number: PDB: 3RVW_A; reference for methods: Hales, B.J. et al. Clin Exp Allergy. 30(2000): 934-943), rDer p 2 (a recombinantly produced Der p 2; sequence published in Chen KW et al, Allergy.67 (2012):609-21; reference for methods: Chen, K., et al. Mol Immunol. 45(2008): 2486-2498.), rDer p 5 (GeneBank: X17699; reference methods: Weghofer M, et al. Int Arch Allergy Immunol. 147(2008):101-9.), rDer p 7 (GeneBank: U37044; reference for methods: Resch Y, et al. Clin Exp Allergy. 41(2011):1468-77), rDer p 21(GeneBank: DQ354124; reference methods: Weghofer M, et al. Allergy. 63(2008):758-67.), rDer p 23(GeneBank: EU414751.1; reference methods: Weghofer M, et al. J Immunol. 190(2013): 3059-67), Der p 1-2 C3 (see example 2), Der p 5 7 21 23_P6 (large) (see example 2) and for control purpose BSA were dotted onto nitrocellulose membranes (Schleicher & Schuell, Germany). Membranes were blocked with gold buffer (50 mM sodium phosphate [pH 7.4], 0.5% [v/v] Tween-20, 0.5% [w/v] BSA, and 0.05% [w/v] sodium azide), three times for 20 min and then incubated with house dust mite-allergic patients' sera (diluted 1:10 in gold buffer) and with a serum from a non-allergic person (1:10 in gold buffer) overnight at 4° C. Bound IgE was detected with 1:10 diluted 125I-labeled anti-human IgE Abs (Demeditec Diagnostics, Kiel, Germany) and visualized by autoradiography (Kodak XOMAT film) as described previously (Curin et al Sci Rep. 22(2017):12135).

Figure 3:
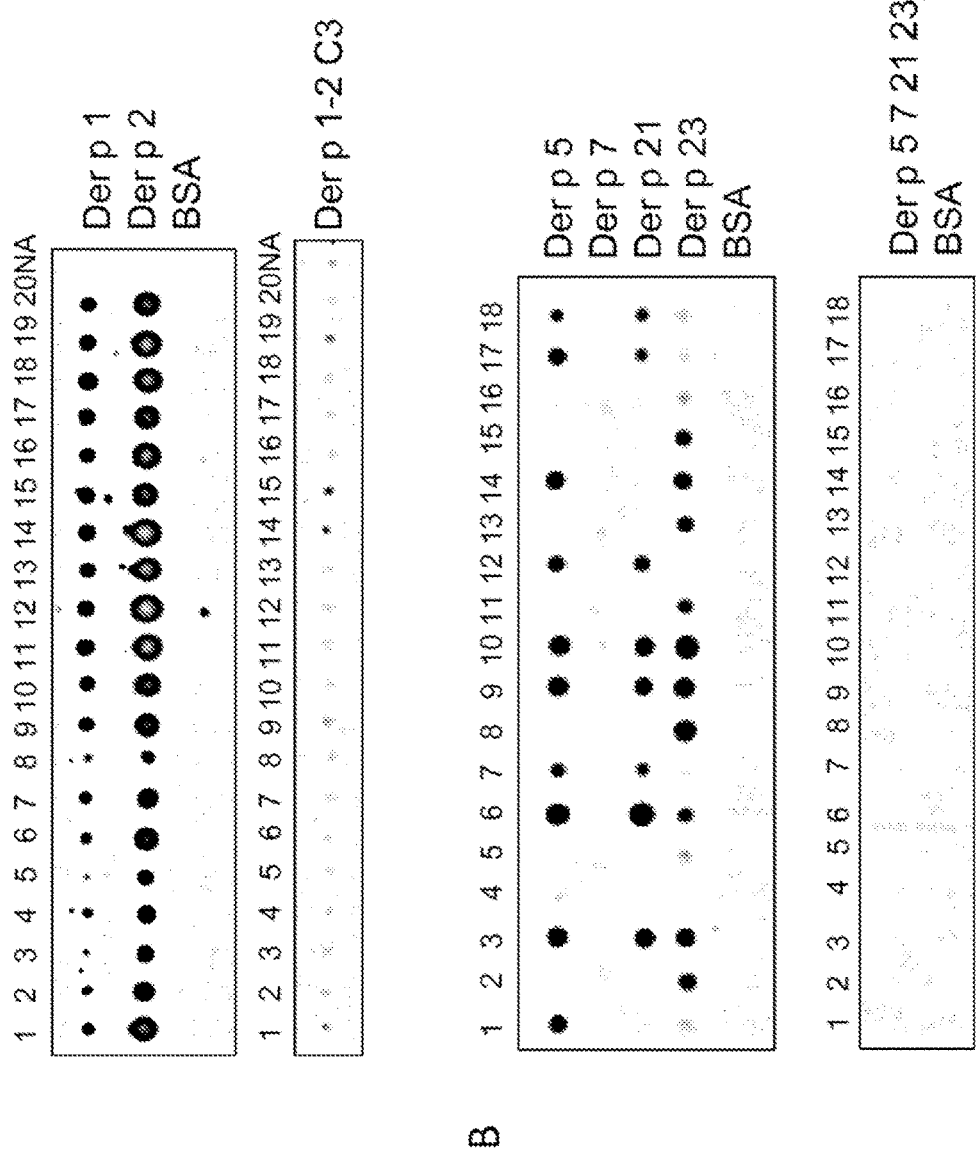
FIG. 3 shows the results of an IgE reactivity assay of Der p 1-2 C3 and Der p 5 7 21 23_P6 (large) as determined by immunoblots.

IgE reactivity of the Der p 1-2 C3 was compared with that of Der p 1 and Der p 2 in 20 HDM-sensitized patients by dot-blot assay (FIG. 3A). While allergic patients reacted with Der p 1 and Der p 2 no patient showed relevant IgE reactivity with Der p 1-2 C3. No reactivity was observed with serum from a non-allergic subject (NA), and the control protein BSA also showed no IgE reactivity (FIG. 3A). In the next experiments IgE reactivity of Der p 5 7 21 23_P6 (large) was compared with IgE reactivity to Der p 5, Der p 7, Der p21 and Der p 23. 18 HDM-sensitized patients reacted with Der p 5, Der p 7, Der p 21 and Der p 23 in a patient dependent manner but neither of tested patients reacted with Der p 5 7 21 23_P6 (large) or with control protein BSA (FIG. 3B).

Example 4: IgE Competition Assay

Information regarding the capacity of the peptides to induce blocking antibodies is important since blocking antibodies were shown to play a major role in immunotherapy of allergies.

In order to examine the ability of immunoglobulins (in particular IgGs) induced by the administration of Der p 1-2 C3 and Der p 5 7 21 23_P6 (large) to mammals to inhibit the binding of house dust mite allergic patients' IgE to house dust mite allergens ELISA competition experiment were performed.

IgE ELISA competition assays were done to analyse the inhibition of human IgE binding to nDer p 1, rDer p 2, rDer p 5, rDer p 7, rDer p 21, rDer p 23 by anti-Der p 1-2 C3 and anti-Der p 5 7 21 23_P6 (large)-specific rabbit IgG. Briefly, ELISA plates (Nunc, Denmark) coated overnight with 1 µg/mL of respective allergen were preincubated for 24 hours with anti-Der p 1-2 C3 antiserum, anti-Der p 5 7 21 23_P6 (large), respective anti-allergen antiserum for a comparison (anti-nDer p 1, anti-rDer p 2, anti-rDer p 5, anti-rDer p 7, anti-rDer p 21 or anti-rDer p 23 antiserum), or, for control purposes, with serum from a non-immunized rabbit (all diluted 1:3) and then washed. After overnight incubation with sera from HDM-allergic patients (diluted 1:10), bound IgE antibodies were detected with horseradish peroxidase-labelled goat anti-human IgE antibodies (KPL, Gaithersburg, Md.). The percentage reduction of IgE binding achieved by pre-incubation with rabbit antisera was calculated as follows: 100−(ODI/ODP)×100) (see FIGS. 6 and 7). ODI and ODP represent optical density values after pre-incubation with the rabbit immune serum or normal rabbit serum, respectively (see Curin M, et al. Sci Rep. 22(2017): 12135).

The anti-Der p 1-2 C3 and anti-Der p 5 7 21 23_P6 (large)-specific rabbit IgG used in this example were obtained as follows. Rabbits (Charles River, France) were immunized three times (first booster injection after 4 weeks and a second booster injection after 7 weeks) with Der p 1-2 C3 or with Der p 5 7 21 23_P6 (large) (200 µg/injection). Al(OH)$_3$ (Serva) was used as adjuvant. 2 rabbits per protein were immunized. Rabbit immune responses were analyzed by ELISA titrations.

The inhibition of patients IgE binding to nDer p 1 achieved with anti-Der p 1-2 C3 antibodies was somewhat lower but close (53% and 58% mean inhibition) to inhibition with anti-nDer p 1 (78% mean inhibition). The inhibition of IgE binding to rDer p 2 achieved with rabbit anti-Der p 1-2 C3 antibodies (89% and 85% mean) was comparable with that obtained with rabbit anti-Der p 2 (mean 84%) (FIG. 6). The inhibition of patients' IgE binding to Der p 5 achieved with anti-Der p 5 7 21 23_P6 (large) (mean inhibitions 76% and 85%) was comparable to inhibition with anti-Der p 5 (mean inhibition 88%) whereas inhibition to Der p 21 was somewhat lower by Der p 5 7 21 23_P6 (large) (mean inhibitions 58% and 58%) than with anti-Der p 21 (mean inhibition 87%). Inhibitions to Der p 7 and Der p 23 were higher by Der p 5 7 21 23_P6 (large) (74% both rabbits for Der p 1 and 47% and 42% for Der p 23) than with anti Der p 7 (58%) and anti-Der p 23 (7%) (FIG. 7).

Example 5: Allergenic Activity as Determined by a Basophil Activation Assay

To test the allergenic activity of the constructs of the present invention, in particular Der p 1-2 C3 and Der p 5 7 21 23_P6 (large), rat basophil leukemia cells (RBL) expressing human high-affinity IgE receptor FcɛRI (1×10$^5$/well) were loaded overnight with sera from the house dust mite-allergic patients at a dilution of 1:10. Cells were washed three times with Tyrode's buffer (Sigma, Austria) and exposed to serial dilutions of allergen (100 ng/mL, 10 ng/mL and 1 ng/mL of of nDer p 1, rDer p 2, rDer p 5, rDer p 7, rDer p 21, rDer p 23, Der p 1-2 C3 and Der p 5 7 21 23_P6 (large), respectively) for 1 h. Serum without allergen or allergen without serum were used as negative controls. Supernatants were analysed for β-hexosaminidase activity as described previously (Hartl et al Allergy 59(2004): 65-73). Experiments were carried out in triplicates, and results are presented as mean percentages of total β-hexosaminidase released after addition of 1% Triton X-100+/− SE of the mean (SEM) (see FIGS. 4 and 5).

Figure 4:
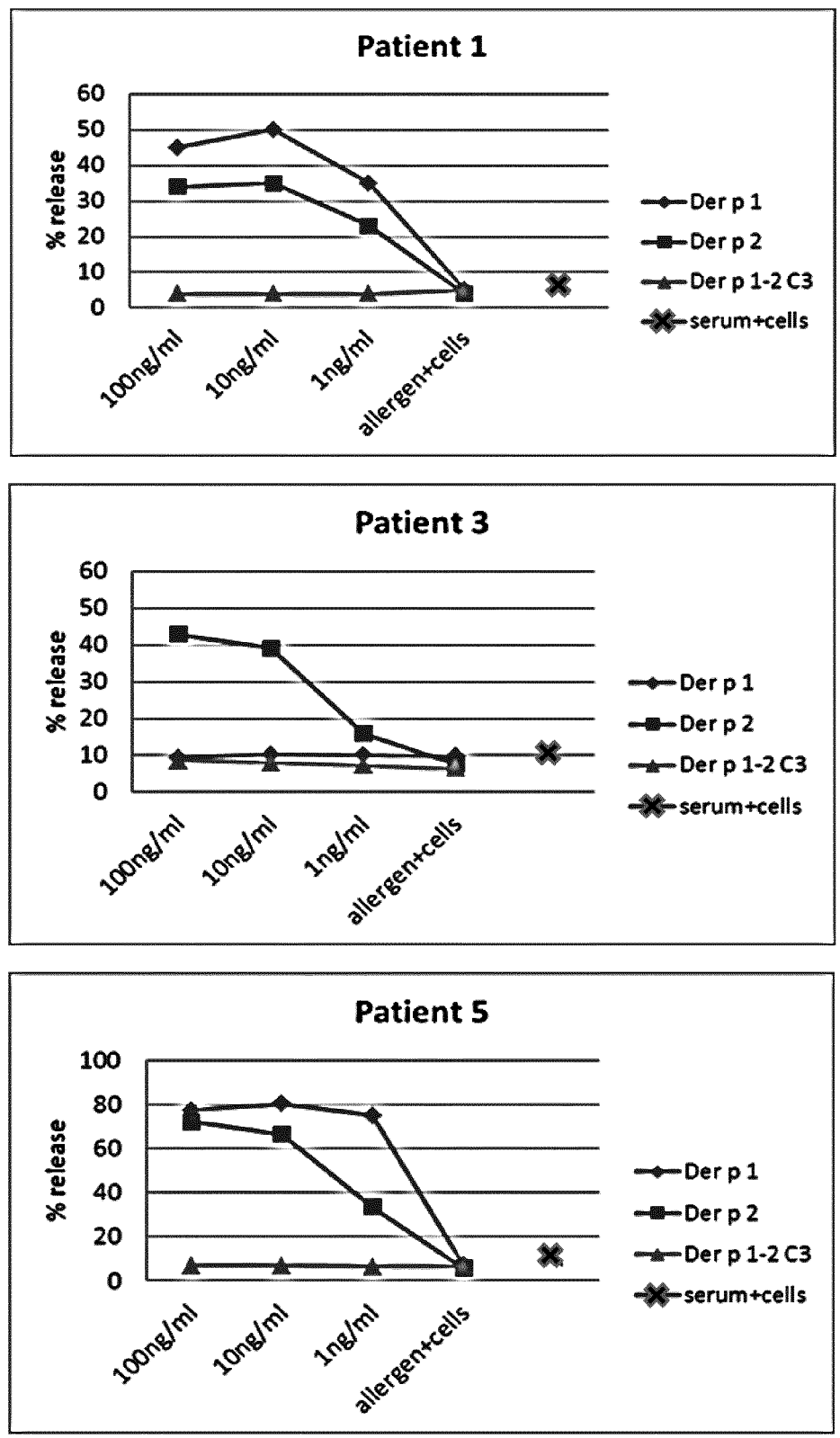
FIG. 4 shows the results of a basophil activation assay demonstrating that Der p 1-2 C3 lacks allergenic activity.
Figure 5:
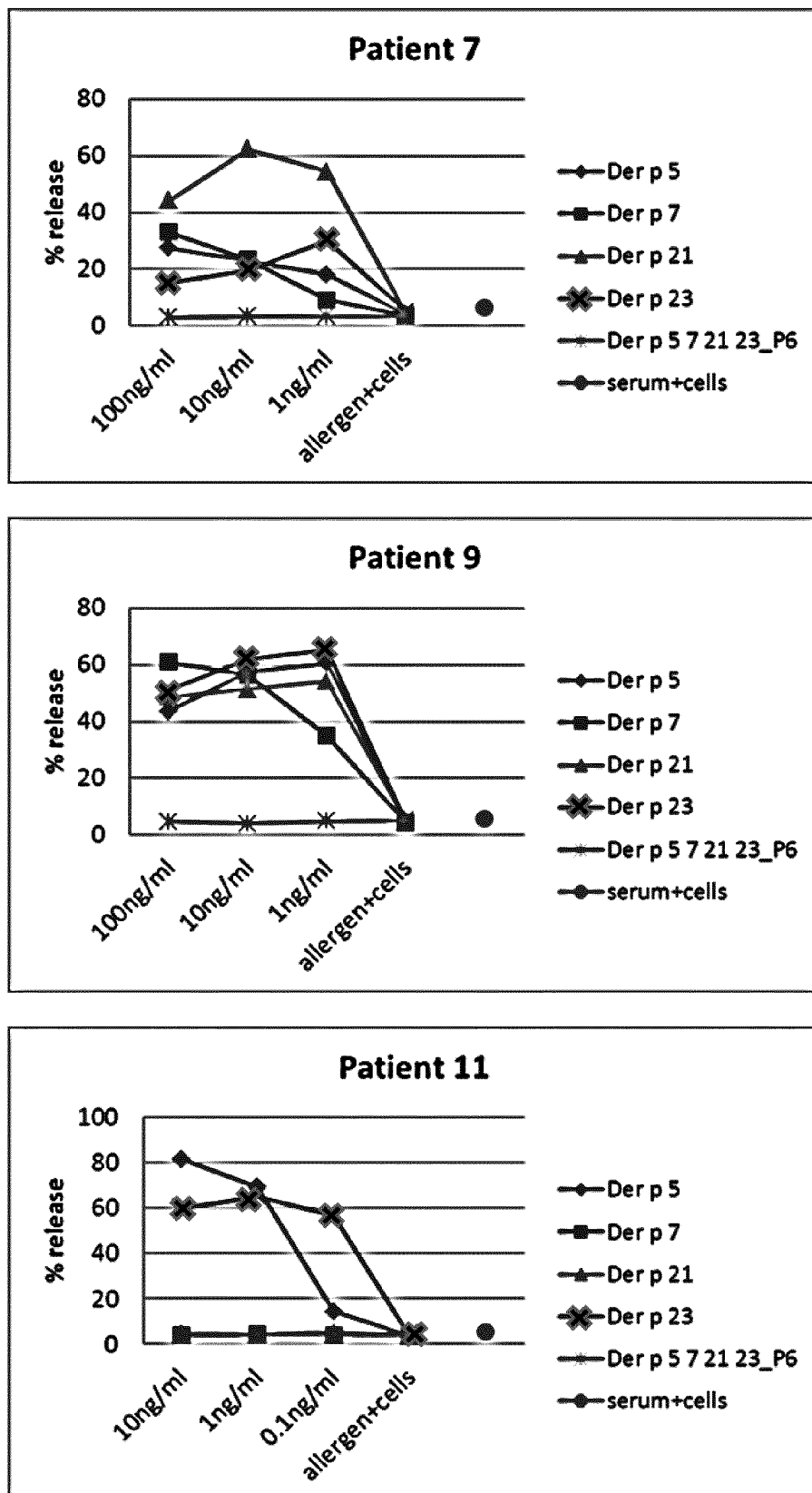
FIG. 5 shows the results of a basophil activation assay demonstrating that Der p 5 7 21 23_P6 lacks allergenic activity.
Figure 5:
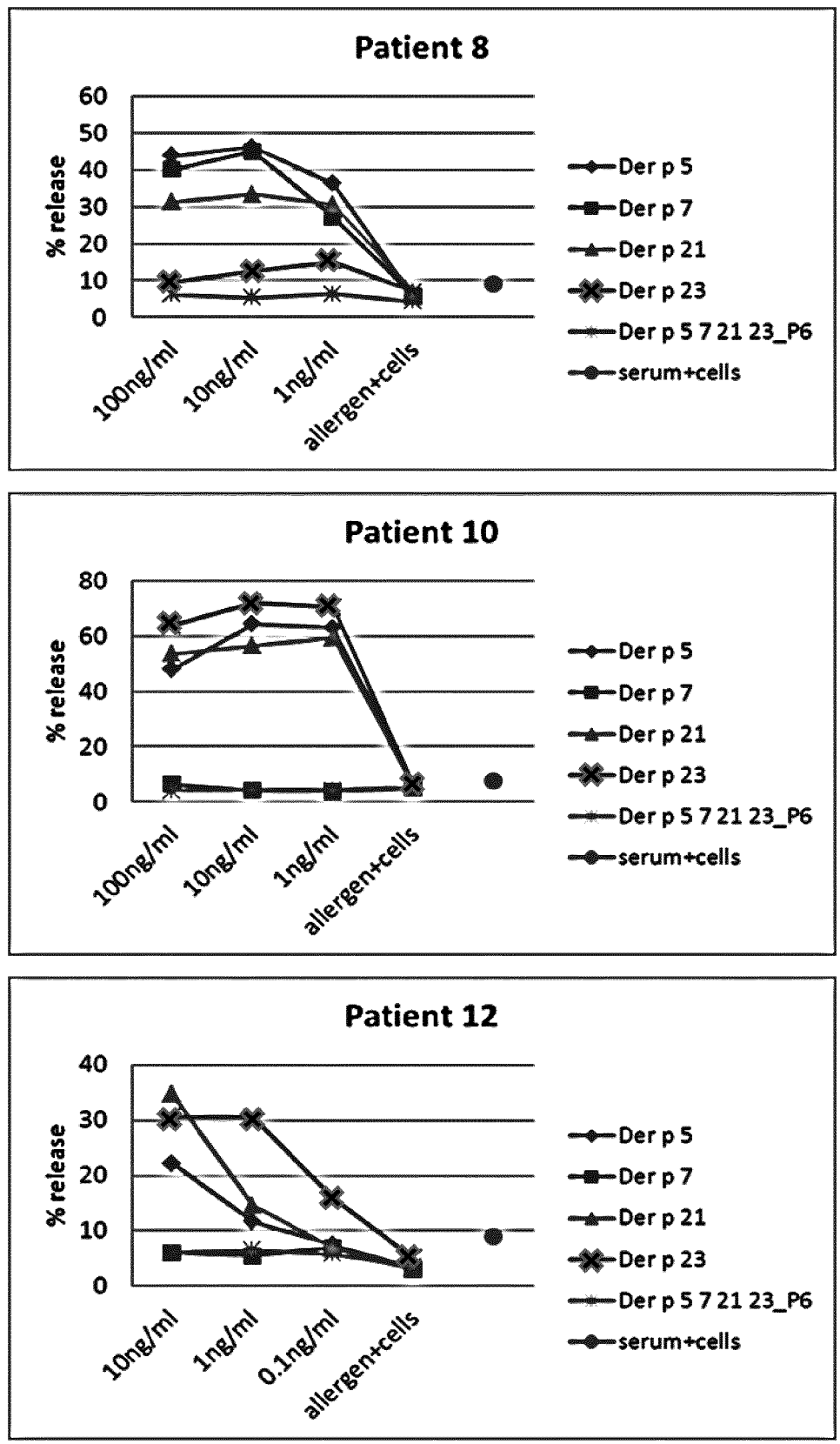

It was found that Der p 1 and Der p 2 induced release of β-hexosaminidase from basophils loaded with serum IgE from HDM-allergic patients whereas the Der p 1-2 C3 did not activate the basophils (FIG. 4). Next set of experiments showed that Der p 5, Der p 7, Der p 21 and Der p 23 induced release of β-hexosaminidase from basophils loaded with serum IgE in a patient dependent manner whereas Der p 5 7 21 23_P6 (large)did not induce basophil release for the same patients' sera (FIG. 5). These data indicate that the constructs Der p 1-2 C3 and Der p 5 7 21 23_P6 (large) do not exhibit allergenic activity.

Example 6: Formation of Allergen-Specific IgGs Induced by BM35 Compared to Commercial HDM Vaccines Groups of two New Zealand white rabbits were immunized each subcutaneously with various doses of BM35 (a preparation comprising the fusion proteins comprising amino acid sequence SEQ ID No. 27 and 28 in a weight ratio of 1:1) and with commercial preparations according to the manufacturers indications (see Table III). Control rabbits were immunized with allergens nDer p1, rDer p 2, rDer p 5, rDer p 7, rDer p 21 and rDer p 23.

TABLE III

| Product | Company | Administration scheme |
|---|---|---|
| Tyro-SIT | Bencard Allergie GmbH | Week 1: 0.1 ml<br>Week 2: 0.3 ml<br>Week 3: 0.5 ml<br>Week 4: 0.1 ml<br>Week 5: 0.3 ml |

TABLE III-continued

| Product | Company | Administration scheme |
|---|---|---|
| Alutard SQ 503 and 510 | ALK-Abelló | Week 6: 0.5 ml
Week 9: 0.5 ml
Week 13: 0.5 ml
Week 17: 0.5 ml
Week 1: 0.2 ml
Week 2: 0.4 ml
Week 3: 0.8 ml
Week 4: 0.2 ml
Week 5: 0.4 ml
Week 6: 0.8 ml
Week 7: 0.2 ml
Week 8: 0.4 ml
Week 9: 0.8 ml
Week 10: 0.2 ml
Week 11: 0.4 ml
Week 12: 0.6 ml
Week 13: 0.8 ml
Week 14: 1 ml
Week 18: 1 ml |
| ACAROID | Allergopharma | Week 1: 0.1 ml
Week 2: 0.2 ml
Week 3: 0.4 ml
Week 4: 0.6 ml
Week 5: 0.1 ml
Week 6: 0.2 ml
Week 7: 0.4 ml
Week 8: 0.6 ml
Week 10: 0.6 ml
Week 13: 0.6 ml
Week 17: 0.6 ml |
| PURETHAL Milbenmischung | HAL Allergy | Week 1: 0.05 ml
Week 2: 0.1 ml
Week 3: 0.2 ml
Week 4: 0.3 ml
Week 5: 0.4 ml
Week 6: 0.5 ml
Week 8: 0.5 ml
Week 10: 0.5 ml
Week 12: 0.5 ml |
| CLUSTOID Milben Injektionssuspension | Roxall Medizin GmbH | Week 15: 0.5 ml
Week 19: 0.5 ml
Week 1: 0.2 ml
(after 15 min 0.5 ml)
Week 4: 0.5 ml
Week 8: 0.5 ml
Week 12: 0.5 ml
Week 16: 0.5 ml |

Serum samples were taken from the rabbits on the day of first immunization and on days 38 and 66 after the first immunization in order to monitor the formation of IgGs specifically binding to house dust mite allergens nDer p 1, rDer p 2, rDer p 5, rDer p 7, rDer p 21 and rDer p 23 in order to determine house dust mite allergen-specific antibody responses. Allergen-specific rabbit IgG responses were measured by diluting sera 1:500 and by using ELISA. Bound rabbit IgG was detected with 1:2000 diluted donkey anti-rabbit horseradish peroxidase-coupled IgG antibodies (NA 934; GE Healthcare UK Limited, Chalfont St Giles, United Kingdom). Color development was done with 2,2'-azino-bis (3-ethylbenzothiazoline-6-sulphonic acid). Sera obtained after immunization with wild type house dust mite allergens served as positive controls.

Figure 9:
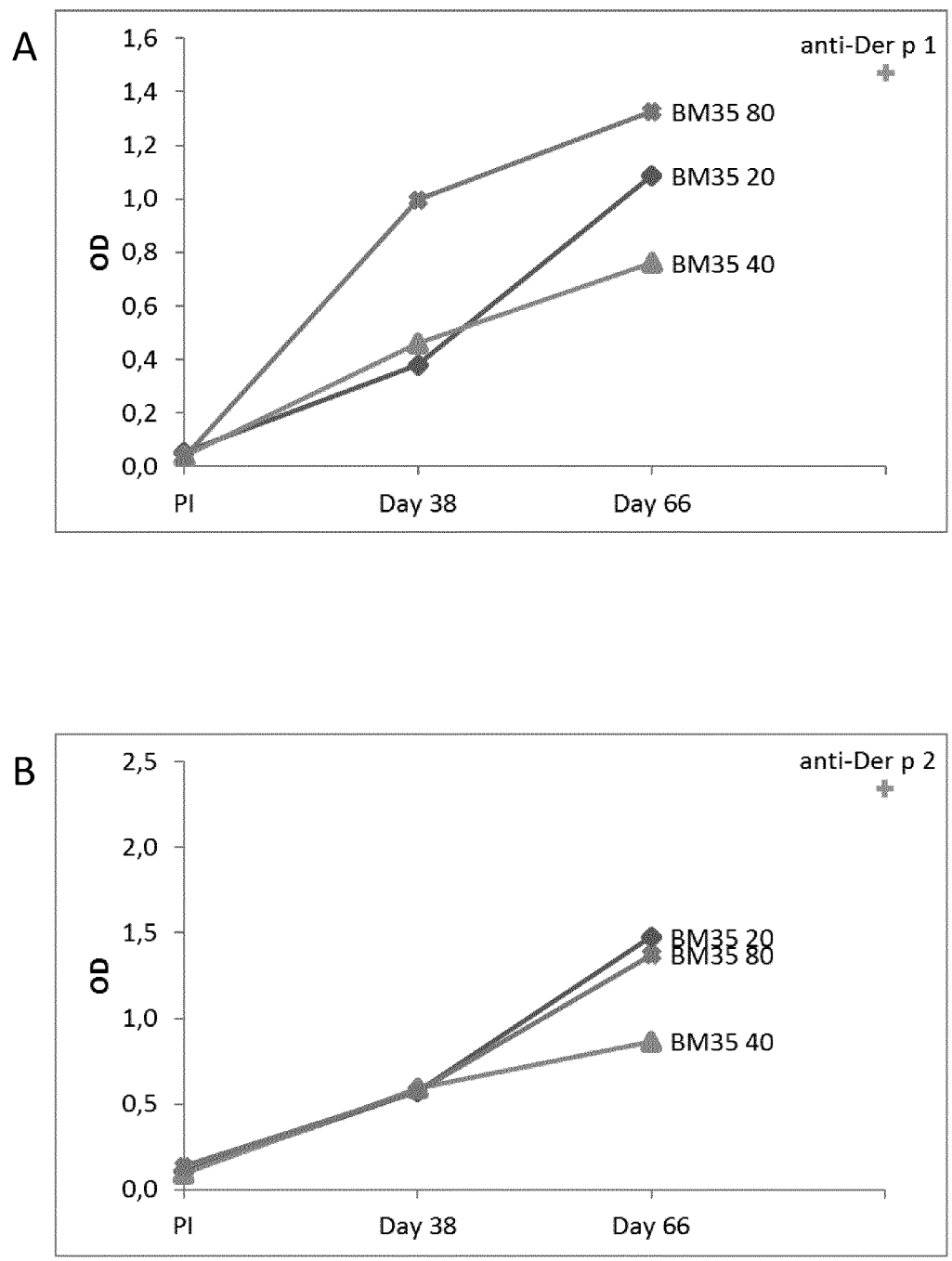
FIGS. 9A to 9F show serum titers of IgGs specifically binding to house dust mite allergens Der p 1 (FIG. 9A), Der p 2 (FIG. 9B), Der p 5 (FIG. 9C), Der p 7 (FIG. 9D), Der p 21 (FIG. 9E) and Der p 23 (FIG. 9F) determined by ELISA from rabbit sera immunized with 20 μg BM35 ("BM35 20"), 40 μg BM35 ("BM35 40") and 80 μg BM35 ("BM35 80") of sera retrieved before the first injection of said immunogens and at days 38 and 66 after the first injection. As controls serum titers of IgG of the respective allergens were determined in serum samples of rabbits vaccinated with allergens nDer p 1, rDer p 2, rDer p 5, rDer p 7, rDer p 21 and rDer p 23.

The results depicted in FIGS. 8 and 9 clearly show that BM35 is able to induce the formation of a much higher titer of allergen specific IgGs compared to the commercial products. It is particularly surprising that BM35 induced the formation of antibodies directed to all 6 house dust mite allergens whereas the commercial products resulted in a much lower allergen specific IgG titer and only for single allergens. Thus, all commercial products showed a weaker induction of IgGs specifically binding to a very limited number of allergens compared to BM35.

The invention claimed is:

1. A fusion protein having formula (I)

$$X_1-Y-X_2 \quad (I),$$

wherein $X_1$ and $X_2$ comprise each four to eight allergen fragments or variants thereof fused to each other, wherein said allergen fragments are derived from at least two allergens of the genus *Dermatophagoides*, and wherein Y is a carrier protein, wherein the at least two allergens are of *Dermatophagoides pteronyssinus* and/or *Dermatophagoides farina*, and selected from the group consisting of Der p 1, Der p 2, Der p 5, Der p 7, Der p 21 and Der p 23, wherein the fusion protein comprises at least one polypeptide having amino acid sequence selected from the group consisting of SEQ ID No. 18, SEQ ID No. 19, SEQ ID No. 20, SEQ ID No. 21, SEQ ID No. 22, SEQ ID No. 23, SEQ ID No. 24 and/or SEQ ID No. 25, wherein a) the allergen fragment of Der p 1 consists of an amino acid sequence being at least 90% identical to an amino acid sequence selected from the group consisting of TNACSINGNAPAEIDLRQMRTVT-PIRMQGGCGSCWAFSGVA (SEQ ID No. 1), ATESAYLAYRNQSLDLAEQELVDCASQHGCHGD-TIPRGIEYIQ (SEQ ID No. 2), HNGVVQESYYRYVAREQSCRRPNAQRFGISN (SEQ ID No. 3), VRNSWDTNWGDNGYGYFAA-NIDLMMIEEYPYVVIL (SEQ ID No. 4), TNASS-INGNAPAEIDLRQMRTVTPIRMQGGSGSS-WAFSGVA (SEQ ID No. 5), ATESAYLAYRNQSLDLAEQELVDSASQHGSHGD-TIPRGIEYIQ (SEQ ID No. 6) and HNGVVQE-SYYRYVAREQSSRRPNAQRFGISN (SEQ ID No. 7), and/or b) the allergen fragment of Der p 2 consists of an amino acid sequence being at least 90% identical to an amino acid sequence selected from the group consisting of CHGSEPCIIHRGKPFQLEAVFEANQNSKTAK (SEQ ID No. 8), EVDVPGIDPNA-CHYMKCPLVKGQQYDIKYTWIVPKIAPKSEN (SEQ ID No. 9), HGSEP-SIIHRGKPFQLEAVFEANQNSKTAK (SEQ ID No. 10) and EVDVPGIDPNASHYMK-SPLVKGQQYDIKYTWIVPKIAPKSEN (SEQ ID No. 11), and/or c) the allergen fragment of Der p 5 consists of an amino acid sequence being at least 90% identical to an amino acid sequence selected from the group consisting of DYQNEFDFLLMERIHEQIKKGELALFYLQ (SEQ ID No. 12) and EQYNLEMAKKSGDILERDLKKEE-ARVKKIEV (SEQ ID No. 13), and/or d) the allergen fragment of Der p 7 consists of amino acid sequence being at least 90% identical to amino acid sequence DPIHYDKITEEINKAVDEAVAAIEK-SETFD (SEQ ID No. 14), and/or e) the allergen fragment of Der p 21 consists of amino acid sequence being at least 90% identical to amino acid sequence YNYEFALESIKLLIK-KLDELAKKVKAVNPDEYY (SEQ ID No. 15), and/or f) the allergen fragment of Der p 23 consists of an amino acid sequence being at least 90% identical to an amino acid sequence selected from the group consisting of GYFADPKDPHKFYICSNWEAVHKDCPGN-TRWNEDEETCT (SEQ ID No. 16) and GYFADPKDPHKFYISSNWEAVHKDSPGN-TRWNEDEETST (SEQ ID No. 17), and/or g) the allergen fragment of Der f 1 consists of an amino acid sequence being at least 90% identical to an amino acid sequence selected from the group consisting of TSACRINSVNVPSELDLRSLRTVT-PIRMQGGCGSCWAFSGVA (SEQ ID No. 38), ATE-SAYLAYRNTSLDLSEQELVDCASQHGCHGD-TIPRGIEYIQ (SEQ ID No. 39), QNGVVEERSYPYVAREQQCRRPNSQHYGISN (SEQ ID No. 40) and VRN-SWDTTWGDSGYGYFQAGNNLMMIEQYPYV-VIM (SEQ ID No. 41), and/or h) the allergen fragment of Der f 2 consists of an amino acid sequence being at least 90% identical to an amino acid sequence selected from the group consisting of HGSDPCIIHRGKPFNLEAIFDANQNTKTAK (SEQ ID No. 42) and EVDVPGIDTNACHYIKCPLVKGQQYDAKYTWNVP-KIAPKSEN (SEQ ID No. 43), and/or i) the allergen fragment of Der f 5 consists of an amino acid sequence being at least 90% identical to an amino acid sequence selected from the group consisting of DYQNEFDFLLMQRIHEQMRKGEEALLHLQ (SEQ ID No. 44) and ERYNVEIALKSNEILERDLKKE-EQRVKKIEV (SEQ ID No. 45), and/or j) the allergen fragment of Der f 7 consists of an amino acid sequence being at least 90% identical to amino acid sequence DPIHYDKITEEINKAIDDAIAAIEQ-SETID (SEQ ID No. 46), and/or k) the allergen fragment of Der f 21 consists of an amino acid sequence being at least 90% identical to amino acid sequence YNFETA VSTIEILVKDLAEL-AKKVKAVKSDD (SEQ ID No. 47), and/or l) the allergen fragment of Der f 23 consists of an amino acid sequence being at least 90% identical to amino acid sequence GYFADPKDPCKFYICSNWEAIHKSCPGN-TRWNEKELTCT (SEQ ID No. 48).

2. The fusion protein according to claim 1, wherein the at least two allergens are of *Dermatophagoides pteronyssinus* and *Dermatophagoides farinae*.

3. The fusion protein according to claim 1, wherein the at least two allergens are of *Dermatophagoides pteronyssinus* and selected from the group consisting of Der p 1, Der p 2, Der p 5, Der p 7, Der p 21 and Der p 23.

4. The fusion protein according to claim 1, wherein the allergen fragments of the at least two allergens consist of 25 to 50 amino acid residues.

5. The fusion protein according to claim 1, wherein at least one, of the cysteine residues of the allergen fragments are substituted with serine, threonine, glycine, alanine, or leucine.

6. The fusion protein according to claim 1, wherein the carrier protein is a surface polypeptide of a virus of a hepadnaviridae family or a fragment of the surface polypeptide.

7. The fusion protein according to claim 1, wherein the fusion protein comprises amino acid sequence SEQ ID No. 27 or amino acid sequence SEQ ID No. 28.

8. A nucleic acid molecule encoding a fusion protein according to claim 1.

9. A vector comprising a nucleic acid molecule according to claim 8.

10. A host cell comprising a nucleic acid molecule according to claim 8.

11. A pharmaceutical preparation comprising at least one fusion protein according to claim 1.

12. The pharmaceutical preparation according to claim 11, wherein two fusion proteins or nucleic acid molecules comprised in the preparation have a weight ratio of 1:10 to 10:1.

13. The pharmaceutical preparation according to claim 11, wherein said preparation comprises a fusion protein comprising amino acid sequence SEQ ID No. 27 and/or a fusion protein comprising amino acid sequence SEQ ID No. 28 or a nucleic acid molecule encoding a fusion protein comprising amino acid sequence SEQ ID No. 27 and/or a fusion protein comprising amino acid sequence SEQ ID No. 28.

14. A method of treating or preventing an allergy in a subject caused by an allergen of a house dust mite, comprising administering to the subject the fusion protein according to claim 1.

15. The fusion protein according to claim 1, wherein the allergen fragments of the at least two allergens consist of 28 to 48 amino acid residues.

16. The fusion protein according to claim 1, wherein the allergen fragments of the at least two allergens consist of 30 to 45 amino acid residues.

17. The fusion protein according to claim 1, wherein at least two of the cysteine residues of the allergen fragments are substituted with serine, threonine, glycine, alanine, or leucine.

18. The fusion protein according to claim 1, wherein at least three of the cysteine residues of the allergen fragments are substituted with serine, threonine, glycine, alanine, or leucine.

19. The fusion protein according to claim 1, wherein all of the cysteine residues of the allergen fragments are substituted with serine, threonine, glycine, alanine, or leucine.

20. The pharmaceutical preparation according to claim 11, wherein two fusion proteins or nucleic acid molecules comprised in the preparation have a weight ratio of 1:5 to 5:1.

21. The pharmaceutical preparation according to claim 11, wherein two fusion proteins or nucleic acid molecules comprised in the preparation have a weight ratio of 2:1 to 1:2.

22. The pharmaceutical preparation according to claim 11, wherein two fusion proteins or nucleic acid molecules comprised in the preparation have a weight ratio of 1:1.

* * * * *